US011566014B2

(12) United States Patent
Nguyen et al.

(10) Patent No.: US 11,566,014 B2
(45) Date of Patent: Jan. 31, 2023

(54) DENSELY CHARGED CATENANES

(71) Applicants: Northwestern University, Evanston, IL (US); King Abdulaziz City for Science and Technology (KACST), Riyadh (SA)

(72) Inventors: Minh T. Nguyen, Evanston, IL (US); James Fraser Stoddart, Evanston, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 268 days.

(21) Appl. No.: 17/045,288

(22) PCT Filed: Apr. 5, 2019

(86) PCT No.: PCT/US2019/026095
§ 371 (c)(1),
(2) Date: Oct. 5, 2020

(87) PCT Pub. No.: WO2019/195754
PCT Pub. Date: Oct. 10, 2019

(65) Prior Publication Data
US 2021/0147384 A1 May 20, 2021

Related U.S. Application Data

(60) Provisional application No. 62/691,923, filed on Jun. 29, 2018, provisional application No. 62/653,301, filed on Apr. 5, 2018.

(51) Int. Cl.
*C07D 401/14* (2006.01)
*H01L 45/00* (2006.01)

(52) U.S. Cl.
CPC ........ *C07D 401/14* (2013.01); *C07B 2200/13* (2013.01); *H01L 45/085* (2013.01)

(58) Field of Classification Search
CPC .................................................. C07D 401/14
See application file for complete search history.

(56) References Cited

U.S. PATENT DOCUMENTS

| | | | |
|---|---|---|---|
| 9,120,799 B2 | 9/2015 | Fahrenbach | |
| 10,867,718 B2 * | 12/2020 | Liu | C07D 519/00 |
| 2014/0350242 A1 | 11/2014 | Chiu | |
| 2019/0016737 A1 * | 1/2019 | Liu | C07D 519/00 |

OTHER PUBLICATIONS

Lewis; J. Am. Chem. Soc. 2018, 140, 14, 4787-4791. https://doi.org/10.1021/jacs.8b01602 (Year: 2018).*
Lopez-Vidal; Dalton Trans., 2018,47, 2492-2496. https://doi.org/10.1039/C7DT04792D (Year: 2018).*
Hein; Pharm Res. 2008, 25, 2216-2230. doi: 10.1007/s11095-008-9616-1 (Year: 2008).*
Amabilino, D. B., et al. "Olympiadane." Angewandte Chemie International Edition in English 33.12 (1994): 1286-1290.
Armspach, D. et al. (1993). The Self-Assembly of Catenated Cyclodextrins. Angew. Chem., Int. Ed. Engl. 32, 854-858.
Asakawa, M. et al. (2000). Current/Voltage Characteristics of Monolayers of Redox-Switchable [2]Catenanes on Gold. Adv. Mater. 12, 1099-1102.
Ashton, P. R., et al. "A [2] catenane made to order." Angewandte Chemie International Edition in English 28.10 (1989): 1396-1399.
Au-Yeung, H. Y., et al. "Strategies to assemble catenanes with multiple interlocked macrocycles." Inorg. Chem. 2018, 57, 7, 3475-3485.
Barat, R. et al. (2015). A Mechanically Interlocked Molecular System Programmed for the Delivery of an Anticancer Drug. Chemical Science 6, 2608-2613.
Barnes, J. C., et al. "A radically configurable six-state compound." Science 339.6118 (2013): 429-433.
Bravo, J. A. et al. (1998). High yielding template-directed syntheses of [2]rotaxanes. Eur. J. Org. Chem. 1998, 2565-2571.
Burgess, M. et al. (2016). Impact of backbone tether length and structure on the electrochemical performance of viologen redox active polymers. Chem. Mater. 28, 7362-7374.
Collier, C. P. et al. (2000). A [2]catenane-based solid state electronically reconfigurable switch. Science 289, 1172-1175.
Coskun, A. et al. (2012). High hopes: can molecular electronics realise its potential? Chem. Soc. Rev. 41, 4827-4859.
Dietrich-Buch Ecker, C. O. et al. (1983). Une nouvelle famille de molecules : les metallo-catenanes. Tetrahedron Lett. 24, 5095-5098. With English abstract.
Dietrich-Buchecker, C. O. et al. (1984). Templated synthesis of interlocked macrocyclic ligands: the catenands. J. Am. Chem. Soc. 106, 3043-3045.
Dolomanov, O. V., et al. "OLEX2: a complete structure solution, refinement and analysis program." Journal of applied crystallography 42.2 (2009): 339-341.
Doris, S. E. et al. (2017). Macromolecular design strategies for preventing active-material crossover in non-aqueous all-organic redox-flow batteries. Angew. Chem. Int. Ed. 56, 1595-1599.
Erbas-Cakmak, S., et al. "Rotary and linear molecular motors driven by pulses of a chemical fuel." Science 358.6361 (2017): 340-343.
Evans, N. H. et al. (2014). Progress in the synthesis and exploitation of catenanes since the millennium. Chem. Soc. Rev. 43, 4658-4683.
Fahrenbach, A. C. et al. (2012). A semiconducting organic radical cationic host-guest complex. ACS Nano 6, 9964-9971.
Feringa, B. L. (2017). The art of building small: from molecular switches to motors (Nobel Lecture). Angew. Chem. Int. Ed. 56, 11060-11078.
Frisch, H. et al. (1953). Zur Struktur der Polysiloxene. I. Monatshefte für Chemie und verwandte Teile anderer Wissenschaften 84, 250-256. With translated summary.
Fu, N. et al. (2009). Squaraine rotaxanes with boat conformation macrocycles. J. Org. Chem. 74, 6462-6468.
Fujita, M. et al. (1994). Quantitative self-assembly of a [2]catenane from two preformed molecular rings. Nature 367, 720-723.

(Continued)

*Primary Examiner* — Daniel R Carcanague
(74) *Attorney, Agent, or Firm* — Quarles & Brady LLP

(57) ABSTRACT

Cationic radial catenane comprising a central cationic ring and two or more radial cationic rings mechanically interlocked central cationic ring and methods for making the same are disclosed herein.

20 Claims, 27 Drawing Sheets

(56) References Cited

OTHER PUBLICATIONS

Fuller, A.-M. L. et al. (2005). Selecting topology and connectivity through metal-directed macrocyclization reactions:? a square planar palladium [2]catenate and two noninterlocked isomers. J. Am. Chem. Soc. 127, 12612-12619.

Gibbs-Hall, I. C., et al. "Catenation through a combination of radical templation and ring-closing metathesis." Journal of the American Chemical Society 137.50 (2015): 15640-15643.

Gil-Ramírez, G. et al. (2015). Catenanes: fifty years of molecular links. Angew. Chem. Int. Ed. 54, 6110-6150.

Green, J. E. et al. (2007). A 160-kilobit molecular electronic memory patterned at 1011 bits per square centimetre. Nature 445, 414-417.

Hamilton, D., et al. (1997). Neutral [2] catenanes from oxidative coupling of p-stacked components. Chemical Communications, (9), 897-898.

Hendriks, K. H. et al. (2018). High-Performance Oligomeric Catholytes for Effective Macromolecular Separation in Nonaqueous Redox Flow Batteries. ACS Central Science 4, 189-196.

Hunter, C. A. (1992). Synthesis and structure elucidation of a new [2]-catenane. J. Am. Chem. Soc. 114, 5303-5311.

International Searching Authority. International Search Report and Written Opinion for application PCT/US2019/026095, dated Aug. 5, 2019. 11 pages.

Jia, C. et al. (2016). Covalently Bonded Single-Molecule Junctions with Stable and Reversible Photoswitched Conductivity. Science 352, 1443-1445.

Johnston, A. G. et al. (1995). Facile synthesis and solid-state structure of a benzylic amide [2]catenane. Angew. Chem., Int. Ed. Engl. 34, 1209-1212.

Li, H. et al. (2010). Mechanical bond formation by radical templation. Angew. Chem. Int. Ed. 49, 8260-8265.

Li, H. et al. (2013). Mechanical bond-induced radical stabilization. J. Am. Chem. Soc. 135, 456-467.

Li, Z. et al. (2012). Mesoporous silica nanoparticles in biomedical applications. Chem. Soc. Rev. 41, 2590-2605.

Megiatto, J. D. et al. (2008). General method for synthesis of functionalized macrocycles and catenanes utilizing "click" chemistry. J. Am. Chem. Soc. 130, 12872-12873.

Mobian, P. et al. (2003). A [2]Catenane constructed around a ru(diimine)32+ complex used as a template. J. Am. Chem. Soc. 125, 2016-2017.

Nguyen, M. T., et al. "Densely charged dodecacationic [3]-and tetracosacationic radial [5] catenanes." Chem 4.10 (2018): 2329-2344.

Niu, Z. et al. (2009). Polycatenanes. Chem. Rev. 109, 6024-6046.

Park, K.-M. et al. (2002). Designed Self-Assembly of Molecular Necklaces. J. Am. Chem. Soc. 124, 2140-2147.

Park, M. et al. (2016). Material Design and Engineering of Next-Generation Flow-Battery Technologies. Nat. Rev. Mater. 2, 16080.

Rostovtsev, V. V., et al. "A stepwise huisgen cycloaddition process: copper (I)-catalyzed regioselective "ligation" of azides and terminal alkynes" Angewandte Chemie (International ed in English) 41.14 (2002): 2596-2599.

Sauvage, J.-P. (2017). From chemical topology to molecular machines (Nobel Lecture). Angew. Chem. Int. Ed. 56, 11080-11093.

Schwarz, F. et al. (2015). Field-induced Conductance Switching by Charge-State Alternation in Organometallic Single-Molecule Junctions. Nat. Nanotechnol. 11, 170.

Schwarz, F. et al. (2016). Charge Transport and Conductance Switching of Redox-Active Azulene Derivatives. Angew. Chem. Int. Ed. 55, 11781-11786.

Stoddart, J. F. (2017). Mechanically interlocked molecules (MIMs)—molecular shuttles, switches, and machines (Nobel Lecture). Angew. Chem. Int. Ed. 56, 11094-11125.

Sue, C.-H., et al. "Enabling tetracationic cyclophane production by trading templates." Chemical Science 1.1 (2010): 119-125.

Sun, J. et al. (2015). An electrochromic tristable molecular switch. J. Am. Chem. Soc. 137, 13484-13487.

Sun, J. et al. (2017). Mechanical bond-protected air-stable radicals. J. Am. Chem. Soc. 139, 12704-12709.

Trabolsi, A. et al. (2010). Radically enhanced molecular recognition. Nat Chem 2, 42-49.

Tung, S.-T. et al. (2013). Synthesis of a [2]catenane from the sodium ion templated orthogonal arrangement of two diethylene glycol chains. Angew. Chem. Int. Ed. 52, 13269-13272.

Vögtle, F. et al. (1992). One-Step synthesis of a fourfold functionalized catenane. Angew. Cherm., Int. Ed. Engl. 31, 1619-1622.

Wang, Y. et al. (2016). Oligorotaxane radicals under orders. ACS Central Science 2, 89-98.

Wang, Y., et al. "Symbiotic Control in Mechanical Bond Formation." Angewandte Chemie (International ed. in English) 55.40 (2016): 12387-12392.

Wasserman, E. (1960). The preparation of interlocking rings: a catenanel. J. Am. Chem. Soc. 82, 4433-4434.

Wasserman, E. (1962). Chemical topology. Scientific American 207, 94-102.

Wei, X. et al. (2017). Materials and Systems for Organic Redox Flow Batteries: Status and Challenges. ACS Energy Letters 2, 2187-2204.

Wen, H. et al. (2016). Complex Formation Dynamics in a Single-Molecule Electronic Device. Science Advances 2(11), e1601113.

Winsberg, J. et al. (2017). Redox-Flow batteries: from metals to organic redox-active materials. Angew. Chem. Int. Ed. 56, 686-711.

Wu, C. et al. (1991). Synthesis of a rotaxane via the template method. Chem. Mater. 3, 569-572.

Wu, Q., et al. "Poly [n] catenanes: Synthesis of molecular interlocked chains." Science 358.6369 (2017): 1434-1439.

Xue, M. et al. (2010). Isomeric Squaraine-Based [2]Pseudorotaxanes and [2]Rotaxanes: Synthesis, Optical Properties, and Their Tubular Structures in the Solid State. Chemistry—A European Journal 16, 8537-8544.

Xue, M. et al. (2015). Development of Pseudorotaxanes and Rotaxanes: From Synthesis to Stimuli-Responsive Motions to Applications. Chem. Rev. 115, 7398-7501.

Yapici, N. B., et al. "Determination of intracellular pH using sensitive, clickable fluorescent probes." Bioorganic & medicinal chemistry letters 22.7 (2012): 2440-2443.

Zhang, L. et al. (2018). Enabling Graphene-Oxide-Based Membranes for Large-Scale Energy Storage by Controlling Hydrophilic Microstructures. Chem 4, 1035-1046.

* cited by examiner

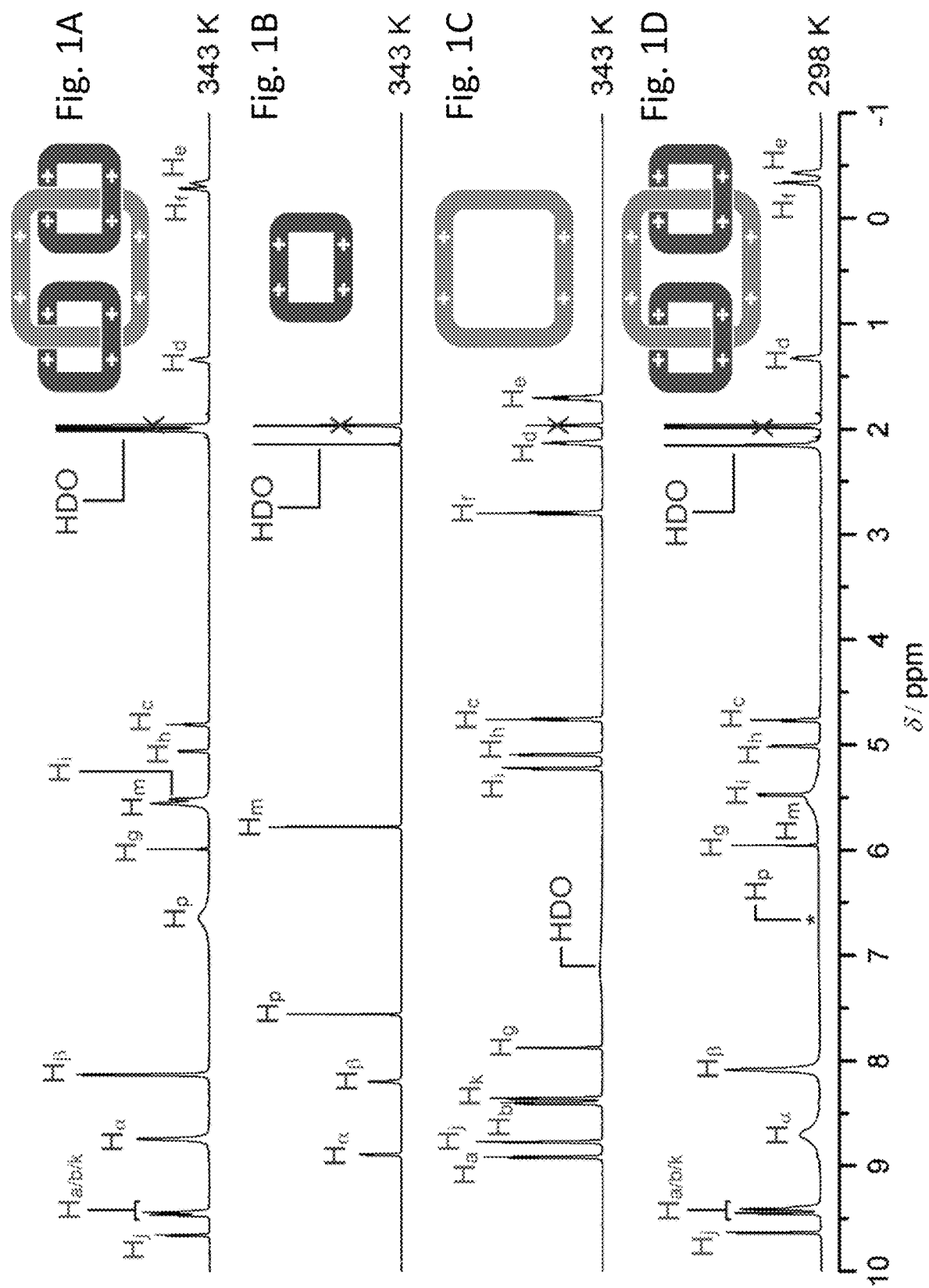

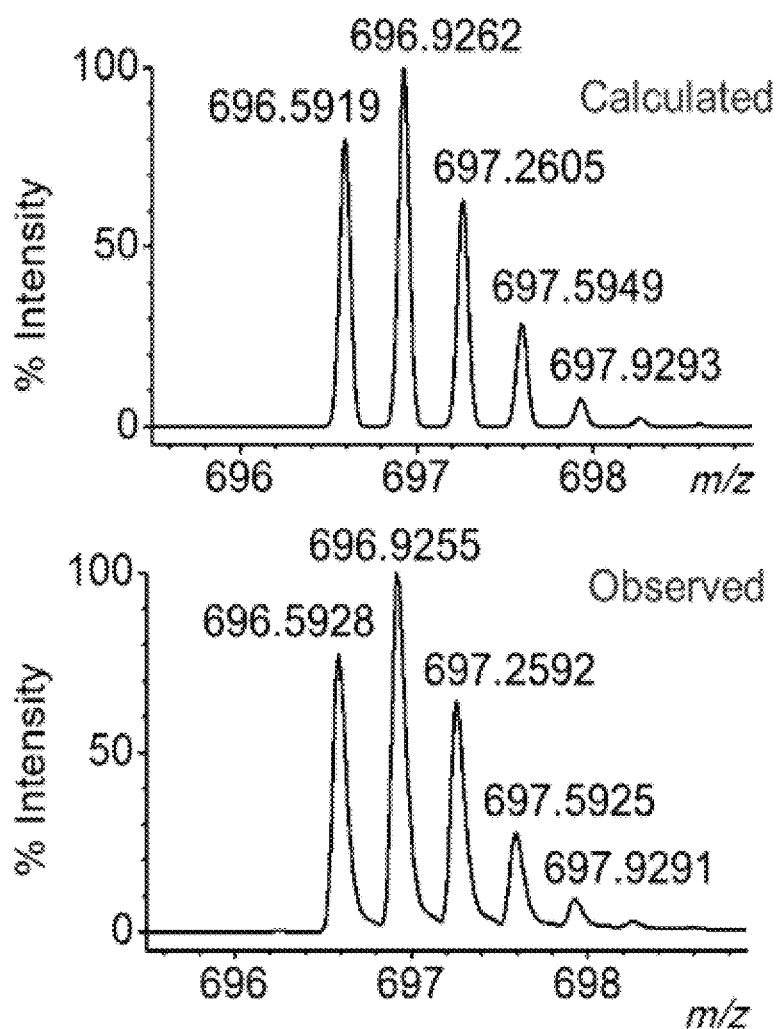
Fig. 4AII

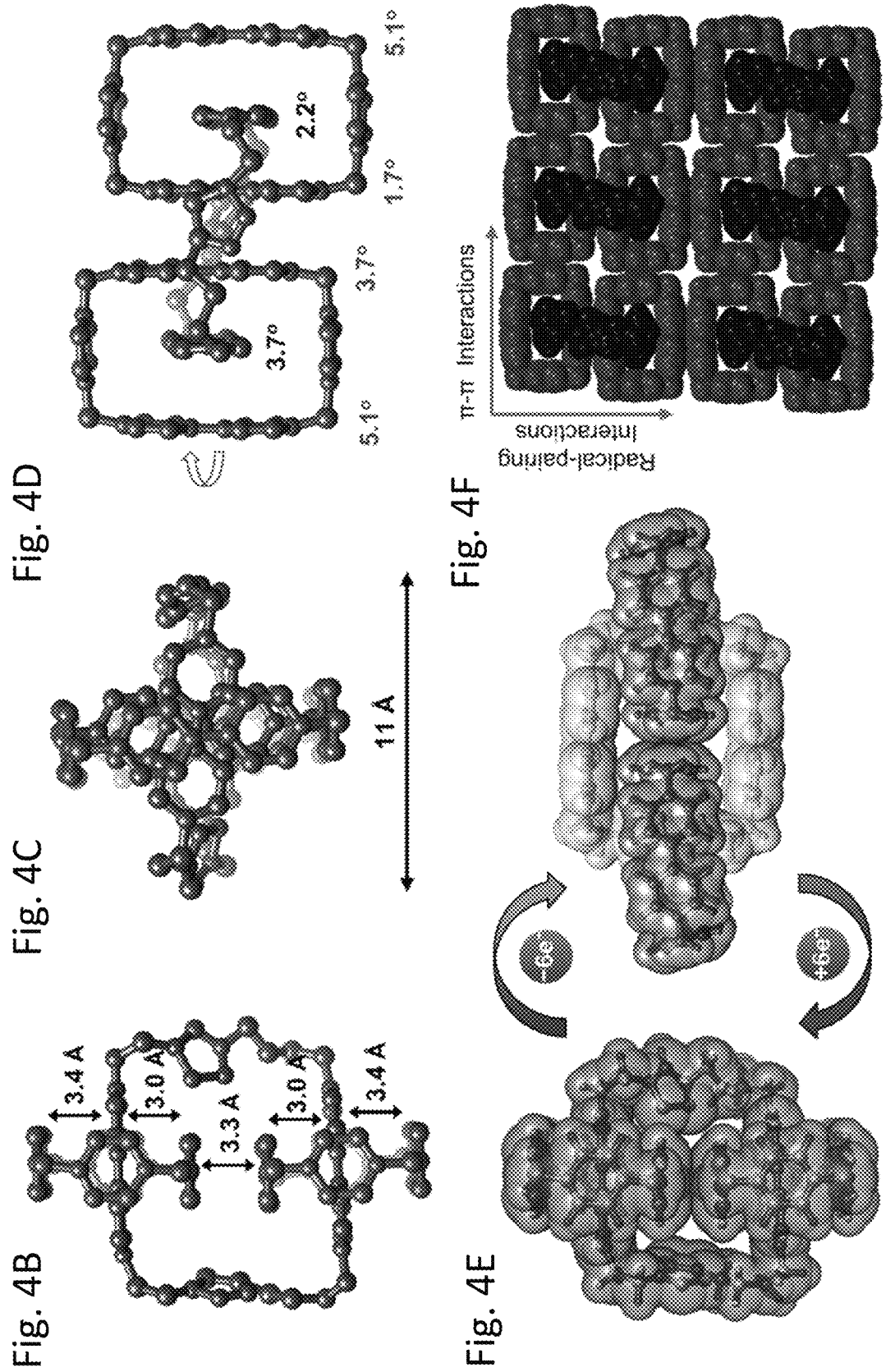

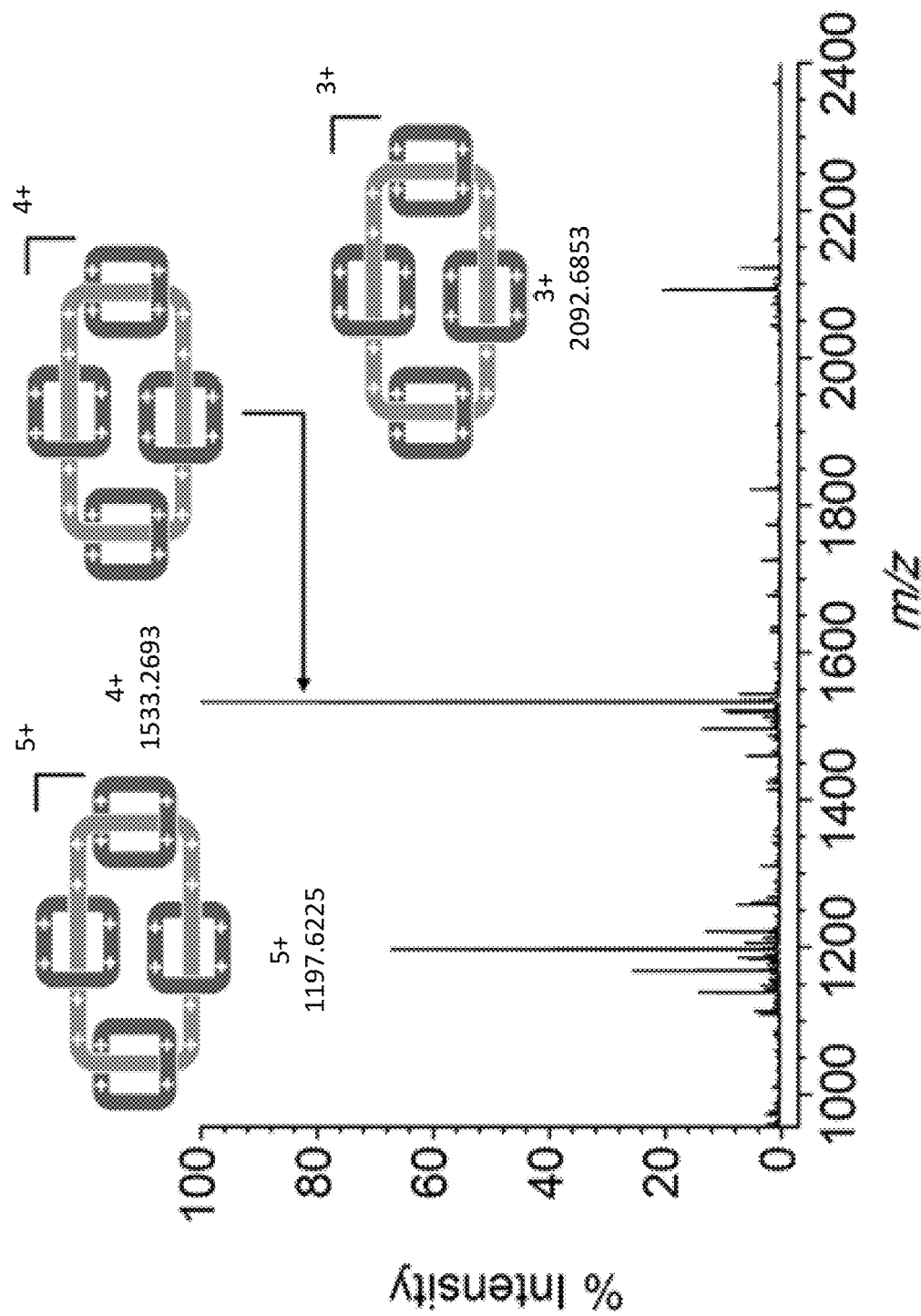
FIG. 6AII

Fig. 6E
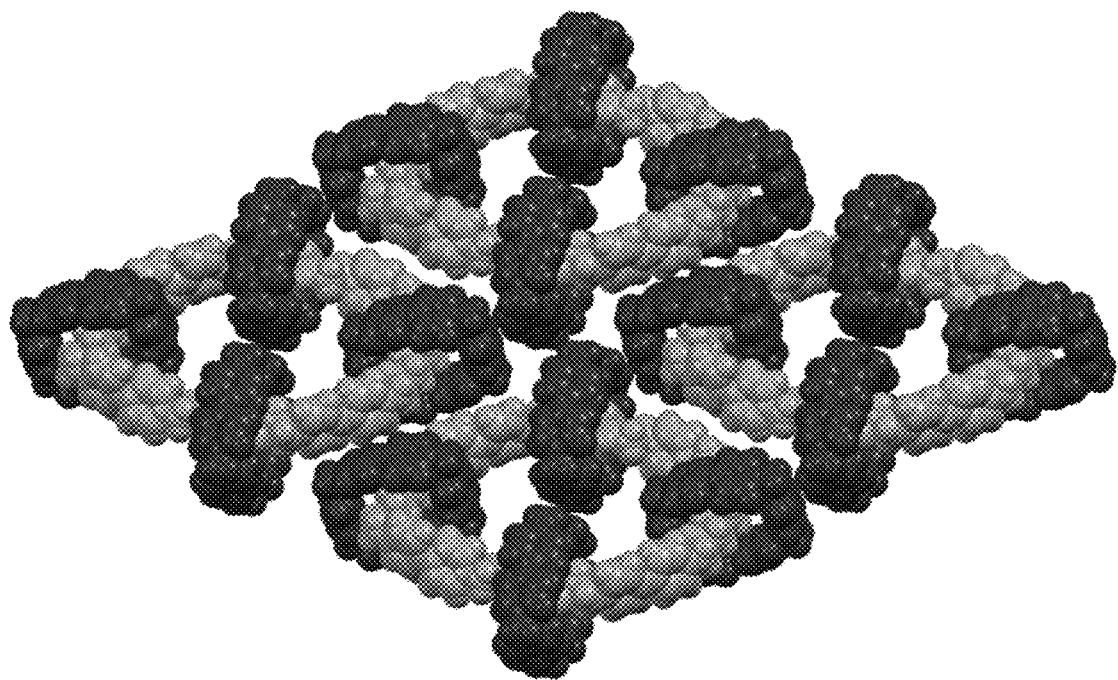
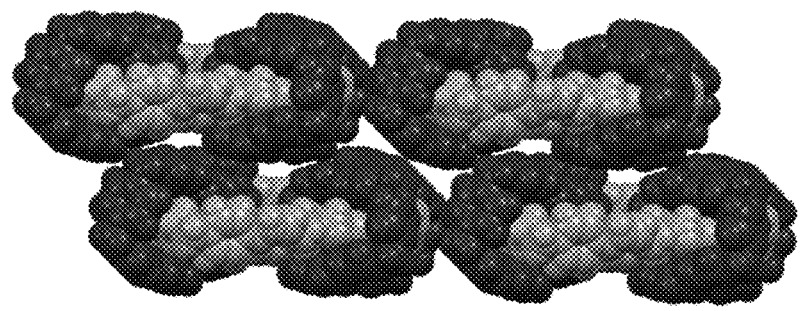
Fig. 6F

DENSELY CHARGED CATENANES

CROSS-REFERENCE TO RELATED APPLICATIONS

The present application represents the U.S. national stage entry of International Application PCT/US2019/026095, filed Apr. 5, 2019, which claims benefit of priority to U.S. Provisional Application No. 62/691,923, filed Jun. 29, 2018, and U.S. Provisional Application No. 62/653,301, filed Apr. 5, 2018, the contents of each are hereby incorporated by reference in their entireties.

BACKGROUND

The advent of supramolecular chemistry has paved the way for the template-directed syntheses of mechanically interlocked molecules (MIMs) whose unique structural features raise the prospect of their potential use in areas as diverse as molecular electronics and artificial molecular machines. Notwithstanding the many synthetic protocols for producing MIMs, mechanically interlocked structures containing multiple components, which intrinsically repel each other, remain undocumented for the most part.

BRIEF SUMMARY OF THE INVENTION

Disclosed herein are densely-charged radial catenanes and methods of making the same. The catenane comprising a central cationic ring and two or more radial cationic rings mechanically interlocked with the central cationic ring. The central cationic ring comprises two or more viologen subunits and two reactive linkers, and the catenane comprises an equal number of radial cationic rings as viologen subunits. Suitably, the central cationic ring may comprise two, three, or four viologen subunits.

Suitably the catenanes are cationic catenanes or radical/cationic catenanes. Moreover, the catenanes disclosed herein demonstrate reversible molecular switching and changing the redox state of the catenanes results in reversible switching of the molecular topologies. In some embodiments, the catenanes may reversibly switch between a 12+ cationic oxidation state and a 6(.+) radical/cationic oxidation state, a 18+ cationic oxidation state and a 9(.+) radical/cationic oxidation state, and a 24+ cationic oxidation state and a 12(.+) radical/cationic oxidation state.

Compositions, including crystalline compositions, and devices comprising the catenanes are also described herein.

Another aspect of the method comprises methods for making the catenanes described herein. The method comprises providing a pseudorotaxane. The pseudorotaxane comprises a threading component having a first terminal moiety, a second terminal moiety, and two or more radical/cation viologen subunits between the first terminal moiety and the second terminal moiety. Suitably, the threading component comprises two, three, or four viologen subunits. The pseudorotaxane also comprises two or more diradical/dicationic rings threaded by the threading component. The number of diradical/dicationic rings threaded by the threading component is equal to the number viologen subunits of the threading component. The method further comprises contacting the first terminal moiety with the second terminal moiety to form a central cationic ring that mechanically interlocks the two or more diradical/dicationic rings, thereby forming the catenane. The method may optionally comprise preparing the pseudorotaxane from one or more pseudoraxanes and/or oxidizing the catenane.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 1A-1D. 1H NMR Spectra (600 MHz, $CD_3CN$) of $[3]C^{12+}$ and its tetracationic non-interlocked macrocycles. (FIG. 1A) $[3]C.12PF_6$ recorded at 343 K showing much better resolved signals of the two $CBPQT^{4+}$ rings compared to those recorded at RT (FIG. 1D), an indication of their fast pirouetting at this elevated temperature. (FIG. 1B) $CBPQT.4PF_6$ recorded at 343 K. (FIG. 1C) $TB.4PF_6$ recorded at 343 K. (FIG. 1D) $[3]C.12PF_6$ recorded at 298 K showing that the two chemically equivalent cyclobis(paraquat-p-phenylene) ($CBPQT^{4+}$) rings are pirouetting slowly on the $^1H$ NMR timescale. The resonance for $H_p$ indicated with an asterisk (*) is very broad and could hardly be observed when plotted on the same intensity scale as the other signals. The peak assignments correspond to the protons labeled in FIG. 5A.

(FIGS. 2A-2C) Ball-and-stick representations—(FIG. 2A) viewed from above the plane containing the $TB^{4+}$ ring, (FIG. 2B) viewed from above the plane containing the two $CBPQT^{4+}$ rings, and (FIG. 2C) viewed along the axis connecting the centroids of three rings. Space-filling representations—(FIG. 2D) viewed from above the plane containing the $TB^{4+}$ ring, (FIG. 2E) viewed from above the plane containing the two $CBPQT^{4+}$ rings, and (FIG. 2F) viewed along the axis connecting the centroids of three rings, showing the compactness and rigidity along the centroids of the three interlocked rings. Hydrogen atoms, $PF_6^-$ counter ions, and solvent molecules have been omitted for sake of clarity.

FIG. 2G shows a first space-filling representation. FIG. 2H shows a space-filling representation from a second view of the representation of FIG. 2G. FIG. 2I shows a space-filling representation from a third view of the representation of FIG. 2G. FIG. 2J shows a space-filling representation from a fourth view of the representation of FIG. 2G.

(FIG. 3A) Cyclic voltammogram of $[3]C.12PF_6$ recorded in a MeCN solution containing 0.1 M $TBAPF_6$ as supporting electrolyte. Scan rate, 100 mV $s^{-1}$. (FIG. 4B) UV-vis-NIR Spectra of $[3]C^{12+}$ (transparent sample) and $[3]C^{6(.+)}$ (colored sample), along with the photographs of the two solutions.

(FIG. 3C) Absorption intensities of $[3]C^{12+}$ (lower points) and $[3]C^{6(.+)}$ (upper points) at 1162 nm wavelength showing the reversible switching between the two states during each cycle. (FIG. 3D) Absorption intensity of $[3]C^{12+}$ (upper points) and $[3]C^{6(.+)}$ (lower points) at 272 nm recorded during each cycle.

(FIG. 4AI) ESI-TOF Mass spectrum of $[3]C^{6(.+)}$ ($PF_6$ salt) recorded under $N_2$. FIG. 4AII shows the expanded spectrum of the 3+ peak, both calculated (top) and observed (bottom).

FIGS. 4B-4D. Ball-and-stick representations of the solid-state structures of $[3]C6^{(.+)}$ (FIG. 4B) viewed from above the plane containing the $TB^{4+}$ ring, (FIG. 4C) viewed from above the plane containing the two $CBPQT^{4+}$ rings, and (FIG. 4D) viewed along the axis connecting the centroids of three rings.

FIG. 4E shows a comparison of the solid-state superstructures of $[3]C^{6(.+)}$ (left) and $[3]C^{12+}$ (right) depicted with combinations of ball-and-stick and space-filling representations.

FIG. 4F. Space-filling representations of the supramolecular arrangements of $[3]C^{6(.+)}$ revealing the molecular packing into 2D layers as a result of both radical-radical interactions between $BIPY^{(.+)}$ units and the π-π interactions of the phenylene units in the $CBPQT^{2(.+)}$ rings. Hydrogen atoms, $PF_6^-$ counter ions, and solvent molecules have been omitted for sake of clarity.

FIG. 4G shows a first space-filling representation. FIG. 4H shows a space-filling representation from a second view of the representation of FIG. 4G. FIG. 4I shows a space-filling representation from a third view of the representation of FIG. 4G. FIG. 4J shows a space-filling representation from a fourth view of the representation of FIG. 4G.

(FIG. 6AI) $^1H$ NMR Spectrum (500 MHz, $CD_3CN$) of $r[5]C.24PF_6$ recorded at 298 K. The spectrum has been abridged in the region of the residual solvent and water resonances, while all signals for $r[5]C^{24+}$ are displayed with peak assignments corresponding to the protons labelled in FIG. 5B. FIG. 6AII shows the HR-ESI-TOF mass spectrum of $r[5]C^{24+}$ ($PF_6$ salt) with signals corresponding to the loss from three to five $PF_6^-$ counter ions. Calculated peaks m/z=2092.9542 $[M-3PF_6]^{3+}$; 1533.2693 $[M-4PF_6]^{4+}$; 1197.6225 $[M-5PF_6]^{5+}$.

(FIG. 6B) View from above the plane containing the $BTB^{8+}$ ring. The $CBPQT^{4+}$ rings are represented in the space-filling fashion. (FIG. 6C) A first side-on view. (FIG. 6D) A second side-on view. Hydrogen atoms in FIGS. 6C and 6D, $PF_6^-$ counter ions, and solvent molecules have been omitted for the sake of clarity.

FIGS. 6E-6F. Representations of the structure of $r[5]C.24PF_6$. Solid-state structures of $r[5]C^{24-}$ including a view from above the plane containing the $BTB^{8+}$ central ring (FIG. 6E) and side-on view (FIG. 6F). Hydrogen atoms, $PF_6^-$ counter ions, and solvent molecules omitted for the sake of clarity.

(FIG. 7A) UV-vis-NIR Spectrum along with the photograph of the solutions of the dodecacationic/dodecaradical radial [5]catenane $r[5]C^{12(.+)}$ and the tetracosacationic $r[5]C^{24+}$ obtained by reducing $r[5]C^{z+}$ with Zn dust in MeCN. (FIG. 7B) Cyclic voltammogram of $r[5]C.24PF_6$ recorded in a DMF solution containing 0.1 M $TBAPF_6$ as supporting electrolyte. Scan rate, 100 mV s$^{-1}$.

(FIG. 7C) CV scans starting with a positive sweep. As there is little to no current found at potential ca. +478 mV in the first scan, the detected current at this potential region in the second and third scans is, therefore, attributed to the oxidation of the generated reduced species, i.e., $r[5]C^{12(.+)}$. (FIG. 7D) CV scans starting with a negative sweep showing no change in peak currents for the first three scans.

DETAILED DESCRIPTION

Figure 2C:
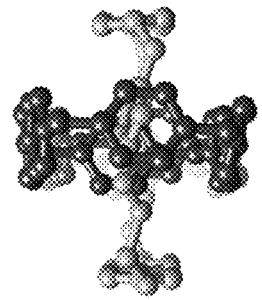
FIGS. 2A-2F. Solid-state structures of $[3]C^{12+}$ deduced from single-crystal X-ray crystallography. Two $CBPQT^{4+}$ rings are mechanically interlocked with a central $TB^{4+}$ ring.
Figure 2F:
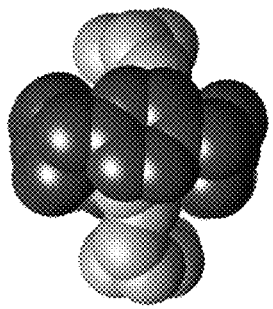

Disclosed herein are densely-charged radial catenanes and methods of making the same. The densely-charged radial catenanes may be a [3]catenane, [4]catenane, or a [5]catenane. The present invention demonstrates a rational strategy, using radical-radical interaction and tandem Click chemistry, to synthesize mechanically interlocked molecules, i.e., radial catenanes, consisting all electrostatically repulsive components. Moreover the catenanes disclosed herein demonstrate reversible molecular switching and changing the redox state of the catenanes results in reversible switching of the molecular topologies.

The presented materials are suited for use in applications that require either (i) densely charged or high-energy-density organic redox materials or (ii) effective switching between different states of a molecule and therefore the material properties, which has been utilized in many electronic devices such as switches, transistors, memory devices and electrochromic devices. Suitably, compositions comprising the catenanes described herein may have a charge density of 5.0+ charge/nm$^3$ or greater, including 6.0+ charge/nm$^3$ or greater or 7.0+ charge/nm$^3$ or greater. The archetypical molecular structure and switching in our invention could hold great promise for the fabrication of next generation organic electronic devices and/or nonaqueous redox-flow batteries.

As demonstrated in the Examples that follow, the radial catenanes may have a high cationic charge density such as a 12+ or a 24+ charge. One exemplary embodiment includes a dodecacationic [3]catenane, comprising three mechanically interlocked positively charged rings despite their mutual Coulombic repulsion. The constitution and topology of this [3]catenane were confirmed by NMR spectroscopy, mass spectrometry, and X-ray crystallography on a single crystal. The solid-state structure shows that two mechanical bonds result in the nano-confinement of 12 positive charges within a volume of less than 1.65 nm$^3$, corresponding to 7.3+ charges/nm$^3$. Another exemplary embodiment includes a radial [5]catenane, comprising four mechanically interlocked rings around a fifth ring and can bears up to 24 positive charges in its co-constitution. The solid-state structure of this organic tetracosacation, determined by X-ray crystallography, reveals a molecular length of 3.7 nm and a charge density of 6.0+ charge/nm$^3$. The template-directed strategy for constructing MIMs, consisting of multiply charged interlocked rings, represents a departure in the chemistry of these compounds that is tantamount to producing a blueprint to explore a novel class of organic molecules which boast large numbers and high densities of like charges.

Definitions

As used herein, an asterisk "*" or a plus sign "+" may be used to designate the point of attachment for any radical group or substituent group.

The term "alkyl" as contemplated herein includes a straight-chain or branched alkyl radical in all of its isomeric forms. The number of atoms in the alkyl group can be specified using $C_n$-$C_m$ nomenclature where n is an integer specifying the lowest number of carbon atoms, m is an integer specifying the greatest number of carbon atoms, and the group may comprise any number of carbon atoms inclusive of n and m. In some embodiments, the alkyl is a $C_1$-$C_{12}$ alkyl, a $C_1$-$C_6$ alkyl, or a $C_1$-$C_3$ alkyl.

The term "alkylene" refers to a diradical of an alkyl group. An exemplary alkylene group is —(CH$_2$)$_n$— where n is an integer greater than or equal to 1. In some embodiments, n is equal to any of 1-12, 1-6, or 1-3.

The term "alkenyl" as used herein refers to an unsaturated straight or branched hydrocarbon having at least one carbon-carbon double bond. The number of atoms in the alkenyl group can be specified using $C_n$-$C_m$ nomenclature where n is an integer specifying the lowest number of carbon atoms, m is an integer specifying the greatest number of carbon atoms, and the group may comprise any number of carbon atoms inclusive of n and m. In some embodiments, the alkenyl is a $C_1$-$C_{12}$ alkenyl, a $C_1$-$C_6$ alkenyl, or a $C_1$-$C_3$ alkenyl.

The term "alkynyl" as used herein refers to an unsaturated straight or branched hydrocarbon having at least one carbon-carbon triple bond. The number of atoms in the alkynyl group can be specified using $C_n$-$C_m$ nomenclature where n is an integer specifying the lowest number of carbon atoms, m is an integer specifying the greatest number of carbon atoms, and the group may comprise any number of carbon atoms inclusive of n and m. In some embodiments, the alkynyl is a $C_1$-$C_{12}$ alkynyl, a $C_1$-$C_6$ alkynyl, or a $C_1$-$C_3$ alkynyl.

The term "aryl" as used herein refers to a carbocyclic aromatic group. Representative aryl groups include phenyl and the like. Unless specified otherwise, the aromatic ring may be substituted, for example, an alkyl. In certain other embodiments, the aromatic ring is not substituted, i.e., it is unsubstituted. The number of atoms in the aryl group can be specified using $C_n$-$C_m$ nomenclature where n is an integer specifying the lowest number of carbon atoms, m is an integer specifying the greatest number of carbon atoms, and the group may comprise any number of carbon atoms inclusive of n and m. In some embodiments, the aryl is a $C_5$-$C_{10}$ alkenyl or a $C_6$-$C_{10}$ aryl.

The term "azide moiety" as used herein refers to a radical comprising —N$_3$.

As described herein, "catenane" means a mechanically-interlocked molecular architecture consisting of two or more interlocked macrocylic components. Once the catenane is formed, the interlocked macrocyclic components cannot be separated without breaking a covalent bond of at least one macrocyclic component. Catenanes by may be prefixed with an integer to indicate the number of mechanically-interlocked macrocyclic components, e.g., [2]catenane or [2]C indicates a catenane comprises two interlocked macrocyclic components, [3]catenane or [3]C indicates a catenane comprises three interlocked macrocyclic components, [4]catenane or [4]C indicates a catenane comprises four interlocked macrocyclic components, and [5]catenane or [5]C indicates a catenane comprises five interlocked macrocyclic components. A radial catenane comprises a central ring and three or more radial rings each mechanically interlocked with the central ring.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_n$-$C_m$ nomenclature where n is an integer specifying the lowest number of atoms in the ring, m is an integer specifying the greatest number of atoms in the ring, and the group may comprise any number of atoms inclusive of n and m. Exemplary heterocyclic groups include triazole groups and alkyl triazole groups.

As described herein, "macrocyclic component" means a molecule that has at least one ring (cycle) large enough to allow it to be threaded onto a linear sub-chain of another molecule. Macrocyclic components include cyclobis(paraquat-p-phenylene) (CBPQT). Depending on context, the macrocyclic component may be used interchangeably with "ring".

"Pseudorotaxane" means a molecular assembly comprising at least one molecule with a linear section threaded through at least one macrocyclic component of another or the same molecule in which the threading component has an end small enough to permit threading or dethreading of the macrocyclic component. Pseudorotaxanes by may be prefixed with an integer to indicate the number of threading components and macrocyclic components, e.g., [2]pseudorotaxane indicates a pseudorotaxane comprising a molecular with at least one linear section onto which one macrocyclic component is threaded and [3]pseudorotaxane indicates a pseudorotaxane comprising a molecular with at least one linear section onto which two macrocyclic components is threaded.

"Reactive linker" means a linker formed from a reaction between moieties that allows for a continuous bridge of atom between viologen subunits. Reactive linkers may be used to extend threading components or close macrocyclic components. Suitably the reaction resulting in the formation of a reactive linker is a click chemistry, e.g., alkyne-azide reaction resulting in a triazole reactive linker, or other suitable reaction.

"Threading component" means a molecule with at least one linear section onto which at least one macrocyclic component is threaded.

"Viologen subunit" (V) means a subunit that is derivative of 4,4'-bipyridine ($C_{10}H_9N_2$). Viologens include 4,4'-bipyridinium (BIPY) subunits. Viologen subunits may be in a dicationic oxidation state (i.e., $V^{2+}$) or a radical/cationic oxidation state (i.e., $V^{\cdot+}$).

Densely Charged Radial Catenanes

One aspect of the invention is directed to densely charged catenanes. The catenanes have a positive charge distributed between mechanically interlocked rings. Catenanes comprise a central cationic ring and two or more radial cationic rings mechanically interlocked with the central cationic ring. Each of the rings is a macrocyclic component that is threaded by a sub-chain of another ring. The central cationic rings comprises two or more viologen subunits (V) and two reactive linkers. Suitably, the central cationic ring may comprise two, three, or four V. V may comprise 4,4'-bipyridinium (BIPY) subunits.

V may reversibly switch between a dicationic oxidation state ($V^{2+}$) or a radical/cationic oxidation state ($V^{\cdot+}$). In certain embodiments each V is in a dicationic state. In other embodiments, each V is in a radical/cationic oxidation state. In yet other embodiments, the V of the central cationic ring may be in any combination of the dicationic state and the radical/cationic oxidation state. For example when the central cationic ring comprises two V, one V may be in the dicationic state and the other V may be in the radical/cationic state. Similarly when the cationic rings comprises three V, one V may be in the dicationic state and the other two V may be in the radical/cationic state or one V may be in the radical/cationic state and the other V may be in the dicationic state.

The catenane comprises an equal number of radial cationic rings as V of the central cationic ring. For example, when the central cationic ring comprises two, three, or four V, the catenane comprises two, three, and four radial cationic rings, respectively. Suitably, the radial cationic rings may reversibly switch between oxidation states. In some embodiments, each of the radial cationic rings are in the same oxidation state. In other embodiments, the radial cationic rings are in different oxidation states. Suitably the radial cationic rings comprises cyclobis(paraquat-p-phenylene) (CBPQT) which may reversibly switch between the tetracationic oxidation state ($CBPQT^{4+}$) and the diradical/dicationic state ($CBPQT^{2(\cdot+)}$). In certain embodiments each CBPQT is in a tetracationic state. In other embodiments, each CBPQT is in a diradical/dicationic oxidation state. In yet other embodiments, the CBPQT of the central cationic ring may be in any combination of the tetracationic state and the diradical/dicationic oxidation states.

In some embodiments, the central cationic ring comprises two V. Suitably, the central cationic ring may comprise

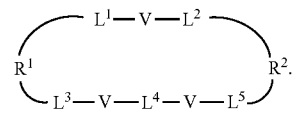

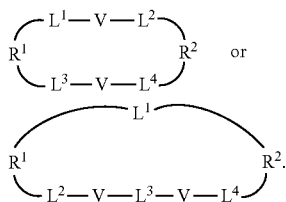

In some embodiments, each V may be in a dicationic oxidation state, resulting in a positive charge of 4+ on the central cationic ring. When each V is in a dicationic oxidation state, the two radial rings may be in a tetracationic oxidation state. In such cases, the catenane is a dodecacationic catenane ($[3]C^{12+}$). In other embodiments, each V may be in a radical/cationic oxidation state, resulting in a positive charge of 2+. When each V is in a radical/cationic oxidation state, each radial rings may be in a diradical/dicationic oxidation state. In such cases, the radial catenane is a dodecacationic radial catenane ($[3]C^{6(\cdot+)}$).

In some embodiments, the central cationic ring comprises three V. Suitably, the central cationic ring may comprise

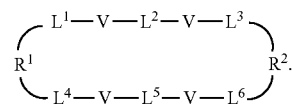

In some embodiments, each V may be in a dicationic oxidation state, resulting in a positive charge of 6+ on the central cationic ring. When each V is in a dicationic oxidation state, the two radial rings may be in a tetracationic oxidation state. In such cases, the radial catenane is a octodecacationic radial catenane ($r[4]C^{18+}$). In other embodiments, each V may be in a radical/cationic oxidation state, resulting in a positive charge of 2+. When each V is in a radical/cationic oxidation state, each radial rings may be in a diradical/dicationic oxidation state. In such cases, the radial catenane is a nonacationic radial catenane ($r[4]C^{9(\cdot+)}$).

In some embodiments, the central cationic ring comprises four V. Suitably, the central cationic ring may comprise In some embodiments, each V may be in a dicationic oxidation state, resulting in a positive charge of 8+ on the central cationic ring. When each V is in a dicationic oxidation state, the two radial rings may be in a tetracationic oxidation state. In such cases, the radial catenane is a tetracosacationic radial catenane ($r[5]C^{24+}$). In other embodiments, each V may be in a radical/cationic oxidation state, resulting in a positive charge of 2+. When each V is in a radical/cationic oxidation state, each radial rings may be in a diradical/dicationic oxidation state. In such cases, the radial catenane is a dodecacationic radial catenane ($r[5]C^{12\cdot+}$).

V is a viologen subunit. $R^1$ and $R^2$ are reactive linkers. Each L is a linker bridging adjacent V, either alone or in combination with another L and/or a reactive linker.

Suitably the reactive linkers $R^1$ and $R^2$ may be formed from a click chemistry reaction. Click chemistry encompasses a group of linking reactions that are simple to perform, have high yields, require no or minimal purification, and are versatile in joining diverse structures without the prerequisite of protection steps. Suitably the click chemistry is a cycloaddition, nucleophilic ring-opening, non-aldol carbonyl chemistry, or a carbon multiple bond reaction. In some embodiments, $R^1$ and $R^2$ are formed from the same click chemistry reaction. In other embodiments, $R^1$ and $R^2$ are formed from different click chemistry reactions. Suitably, $R^1$ and/or $R^2$ is formed from a cycloaddition reaction such as an alkyne-azide reaction forming a triazole.

Suitably each L is independently selected from an alkyl, an alkenyl, an aryl, an alkylaryl, a triazole, or an alkyltriazole. A linker L may bridge adjacent V, either alone or in combination with another L and/or a reactive linker. In some embodiments, the bridge comprises a continuous bride of 8, 9, 10, 11, or 12 atoms between V.

Methods of Making Densely Charged Radial Catenanes

Methods for making the catenanes described above are also provided. The method for forming the catenane comprises contacting terminal moieties of a pseudorotaxane to form a central cationic ring that mechanically interlocks radials cationic rings. The pseudorotaxane comprises a threading component having a first terminal moiety, a second terminal moiety, and two or more radical/cation viologen subunits between the first terminal moiety and the second terminal moiety and two or more diradical/dicationic rings threaded by the threading component. The pseudorotaxane may comprise an equal number of diradical/dicationic rings as viologen subunits. Suitably, the threading component may comprises two, three, or four viologen subunits.

Suitably V is in a radical/cationic oxidation state ($V^{\cdot+}$). Although V may be in a dicationic state, when V is in the radical/cationic oxidation state the viologen subunit may form stabilizing radical-radical interactions with radial rings that also have unpaired electrons that are threaded by the threading component. Suitably the radial cationic rings comprises cyclobis(paraquat-p-phenylene) (CBPQT) in the diradical/dicationic state ($CBPQT^{2(\cdot+)}$). In certain embodiments each CBPQT is in a tetracationic state. In other embodiments, each CBPQT is in a diradical/dicationic oxidation state. In yet other embodiments, the CBPQT of the central cationic ring may be in any combination of the tetracationic state and the diradical/dicationic oxidation states.

In some embodiments, the threading component comprises two V. The threading component of the pseudorotaxane may comprise

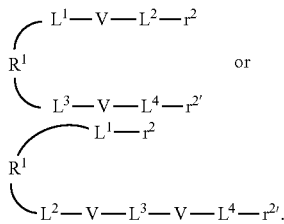

Suitably, each V may be in a radical/cationic oxidation state, resulting in a positive charge of 2+ as well as two unpaired electrons, which may interact with radial cationic rings that also have unpaired electrons to stabilize the pseudorotaxane.

The first of these threading components may be formed by contacting threading components $r^1$-$L^1$-V-$L^2$-$r^2$ and $r^{1\prime}$-$L^3$-V-$L^4$-$r^{2\prime}$ and Suitably, each V may be in a radical/cationic oxidation state, resulting in a positive charge of 1+ as well as one unpaired electrons. Suitably each of these threading components form a pseudorotaxane that threads a radial ring. These threading components may interact with a radial cationic ring having unpaired electrons to stabilize the pseduorotaxane.

The second of these threading components may be formed by contacting $r^1$-$L^1$-$R^2$ and threading component $r^{1\prime}$-$L^2$-V-$L^3$-V-$L^4$-$r^{2\prime}$ Suitably, each V may be in a radical/cationic oxidation state, resulting in a positive charge of 2+ as well as two unpaired electrons on the threading component. Suitably the threading component forms a pseudorotaxane that threads two radial rings. These threading component may interact with the radial cationic rings having unpaired electrons to stabilize the pseduorotaxane.

In some embodiments, the threading component comprises three V. Suitably, the threading component of the pseudorotaxane comprises

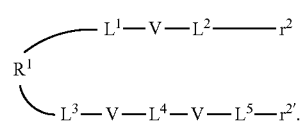

Suitably, each V may be in a radical/cationic oxidation state, resulting in a positive charge of 3+ as well as three unpaired electrons, which may interact with radial cationic rings that also have unpaired electrons to stabilize the pseudorotaxane.

The threading components may be formed by contacting threading components $r^1$-$L^1$-V-$L^2$-$r^2$ and $r^{1\prime}$-$L^3$-V-$L^4$-V-$L^5$-$r^{2\prime}$ and Suitably, each V may be in a radical/cationic oxidation state, resulting in a positive charge of 1+ as well as one unpaired electron, one of the threading components and a positive charge of 2+ as well as two unpaired electrons on the other threading component. Suitably each of these threading components may form a pseudorotaxanes that threads one or two radial rings, respectively. These threading components may interact with radial cationic rings associated therewith that also have unpaired electrons to stabilize the pseduorotaxanes.

In some embodiments, the threading component comprises four V. The threading component of the pseudorotaxane may comprise

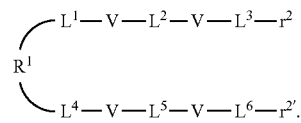

Suitably, each V may be in a radical/cationic oxidation state, resulting in a positive charge of 4+ as well as four unpaired electrons, which may interact with radial cationic rings that also have unpaired electrons to stabilize the pseudorotaxane.

The threading components may be formed by contacting threading components $r^1$-$L^1$-V-$L^2$-V-$L^3$-$r^2$ and $r^{1\prime}$-$L^4$-V-$L^5$-V-$L^6$-$r^{2\prime}$ and Suitably, each V may be in a radical/cationic oxidation state, resulting in a positive charge of 2+ as well as two unpaired electrons on each threading component. Suitably each of these threading component may form a pseudorotaxane that threads two radial rings. These threading components may interact with radial cationic rings associated therewith that also has unpaired electrons to stabilize the pseduorotaxane reactants.

Terminal moieties r² and r²' may suitably be selected to react and form the reactive linker R² and r¹ and r¹' may suitably be selected to react and form the reactive linker R¹. Suitably r² and r²' and r¹ and r¹' may be selected from moieties capable of performing a click chemistry reaction. In some embodiments, r² and r²' and r¹ and r¹' are selected to perform a cycloaddition reaction such as an alkyne-azide reaction forming a triazole.

Suitably, the catenanes may be reversibly oxidized with a suitably selected oxidant or reductant. For example, a radial catenane in a reduced state may be oxidized by an oxidant such as $NOPF_6$ or a radial catenane in an oxidized state may be reduced by a reductant such as Zn dust.

Dodecacationic and Hexaradical/Hexacationic Radial [3]Catenanes

One aspect of the invention is directed to dodecacationic and hexaradical/hexacationic [3]catenanes. As will be shown in the Examples below, the dodecacationic and hexaradical/hexacationic [3]catenanes may be reversibly interconverted between the different oxidation states as well as molecular topologies.

Figure 5A:
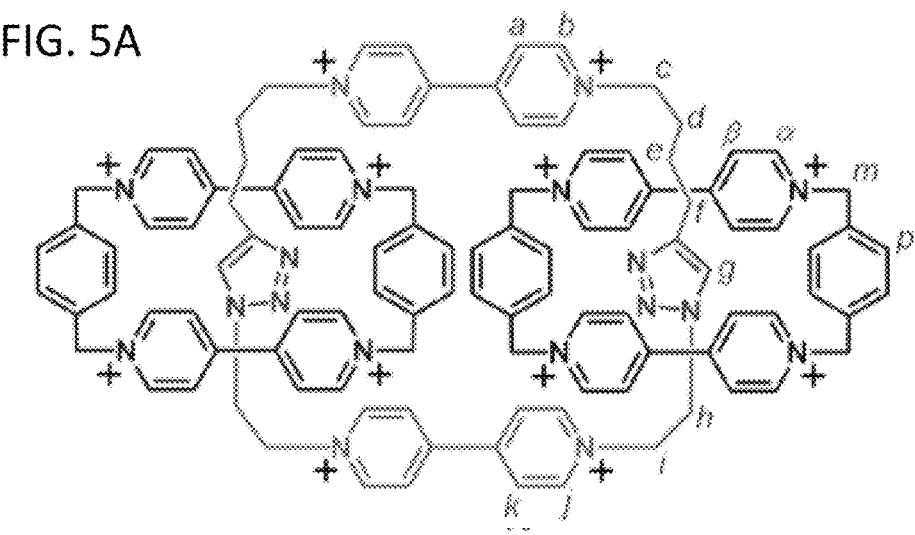
FIGS. 5A-5B. Chemical formulae of $[3]C^{12+}$ (FIG. 5A) and $r[5]C^{24+}$ (FIG. 5B) showing proton assignments.

The dodecacationic [3]catenane (r[3]$C^{12+}$) comprises a central tetracationic ring mechanically interlocked with a second tetracationic ring and a third tetracationic ring. An exemplary [3]$C^{12+}$ is provided in FIG. 5A.

The second tetracationic ring and the third tetracationic ring may be any tetracationic macrocyclic component. In some embodiments, the second or third ring comprises cyclobis(paraquat-p-phenylene) tetracation ($CBPQT^{4+}$).

In some embodiments, the [3]$C^{12+}$ comprises the catenane of Formula Ia

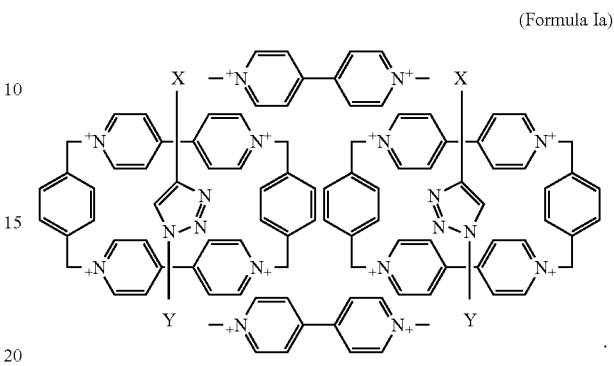

(Formula Ia)

or the hexaradical/hexacationic [3]catenane ([3]$C^{6(.+)}$) comprises the catenane of Formula IIa

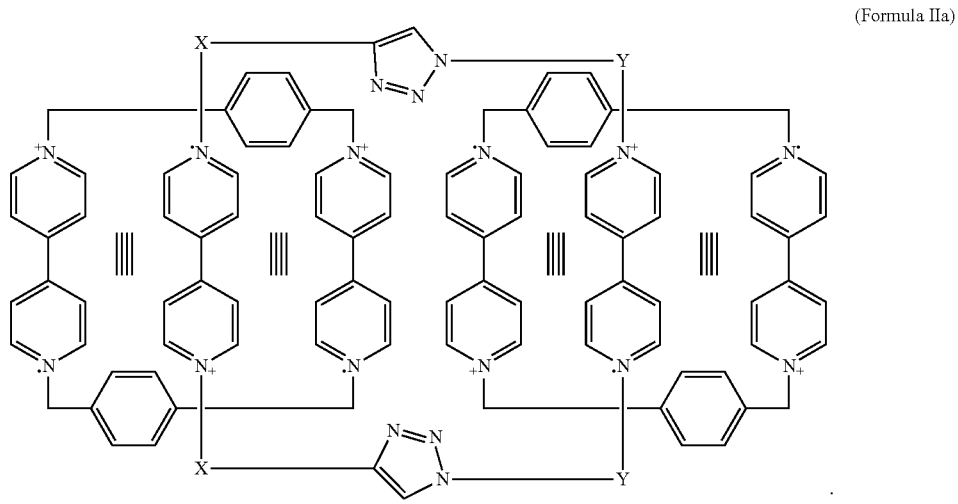

(Formula IIa)

The hexaradical/hexacationic [3]catenane (r[3]$C^{6(.+)}$) comprises a central diradical/dicationic ring mechanically interlocked with a second diradical/dicationic ring and a third diradical/dicationic ring.

Linker R¹, linker R², or both linker R¹ and linker R² may comprise a triazole group formed from a click reaction between a azide and akyne moiety. Both or at least one of the linkers R¹ and R² may allow the opposing viologen subunits to be separated by a distance of about 9.5 Å and restrict the separation from 8.0 to 12.0 Å or anything in between, including from about 9.0 Å to about 11.0 Å. In order to allow for these separations, the linkers may comprise a continuous bridge of about 7 to about 16 atoms or anything in between, including from about 8 to about 12 atoms. For the purposes of counting, if the continuous bridge of atoms bifurcates, e.g., at a triazole group, one counts the atoms along the bridge formed by the fewest number of atoms.

X and Y together with the triazole group form the linkers R¹ and R². X may comprise diradicals of alkyl groups, alkenyl groups, aryl groups, alkylaryl groups, triazole groups, or alkyltriazole groups. Y may comprise diradicals of alkyl groups, alkenyl groups, aryl groups, alkylaryl groups, triazole groups, or alkyltriazole groups.

The length of the X-triazole-Y linker may be any suitable length. In some cases, the X-triazole-Y linker of Formula Ib or Formula IIa comprises a continuous bridge of 8, 9, 10, 11, or 12 atoms. In some embodiments, X comprises —$(CH_2)_{nx}$— where nx is 0, 1, 2, 3, 4, 5, or 6, —$(CH_2)_{mx}(C_2N_3H)(CH_2)_{mx'}$— where mx+mx' is 0, 1, or 2, or —$(CH_2)_{lx}(C_6H_4)(CH_2)_{lx'}$— where lx+lx' is 0, 1, or 2. In some embodiments, Y comprises —$(CH_2)_{ny}$— where ny is 0, 1, 2, 3, 4, 5, or 6, —$(CH_2)_{my}(C_2N_3H)(CH_2)_{my'}$— where my+my' is 0, 1, or 2, or —$(CH_2)_{ly}(C_6H_4)(CH_2)_{ly'}$— where ly+ly' is 0, 1, or 2. In some embodiments, X comprises —$(CH_2)_{nx}$— where nx is 0, 1, 2, 3, 4, 5, or 6, —$(CH_2)_{mx}(C_2N_3H)(CH_2)_{mx'}$— where mx+mx' is 0, 1, or 2, or —$(CH_2)_{lx}(C_6H_4)(CH_2)_{lx}'$— where lx+lx' is 0, 1, or 2 and Y comprises —$(CH_2)_{ny}$— where ny is 0, 1, 2, 3, 4, 5, or 6, —$(CH_2)_{my}(C_2N_3H)(CH_2)_{my}'$— where my+my' is 0, 1, or 2, or $(CH_2)_{ly}(C_6H_4)(CH_2)_{ly}'$— where ly+ly' is 0, 1, or 2.

In some embodiments, X and Y both comprise alkyl groups. In certain embodiments, X comprises —$(CH_2)_{nx}$—, Y comprises —$(CH_2)_{ny}$—, and nx+ny=6, including an embodiment where nx=4 and ny=2, nx=3 and ny=3, or nx=2 and ny=4.

In some embodiments, X comprises an alkyl group and Y comprises an aryl or alkylaryl group. In certain embodiments, X comprises —$(CH_2)_{nx}$—, Y comprises —$(CH_2)_{ly}(C_6H_4)(CH_2)_{ly}'$—, and nx+ly+ly'=3, including an embodiment where nx=2 and ly+ly'=1.

In some embodiments, X comprises a triazole or alkyltriazole group and Y comprises an alkyl. In certain embodiments, wherein X comprises —$(CH_2)_{my}(C_2N_3H)(CH_2)_{my}'$—, Y comprises —$(CH_2)_{ny}$—, and my+my'+ny=4, including an embodiment where my+my'=2 and ny=2.

In some embodiments, the $[3]C^{12+}$ comprises the catenane of Formula Ib or Formula Ic

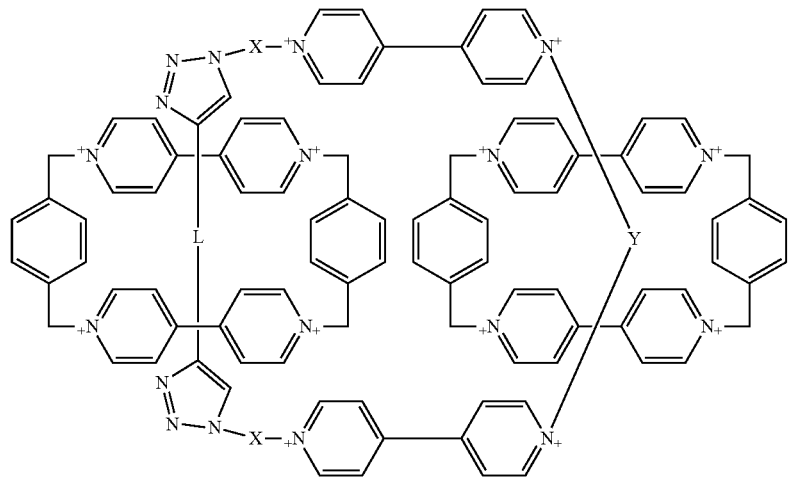

(Formula Ib)

or

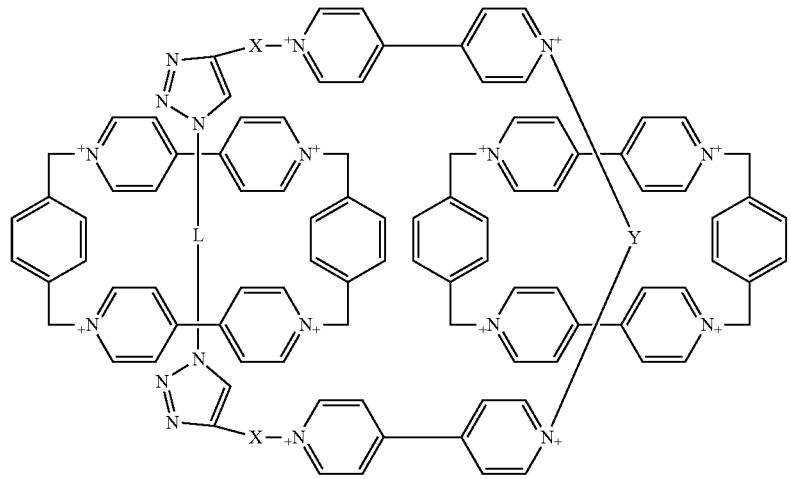

(Formula Ic)

or the hexaradical/hexacationic [3]catenane ($[3]C^{6(\cdot+)}$) comprises the catenane of Formula IIb or IIc
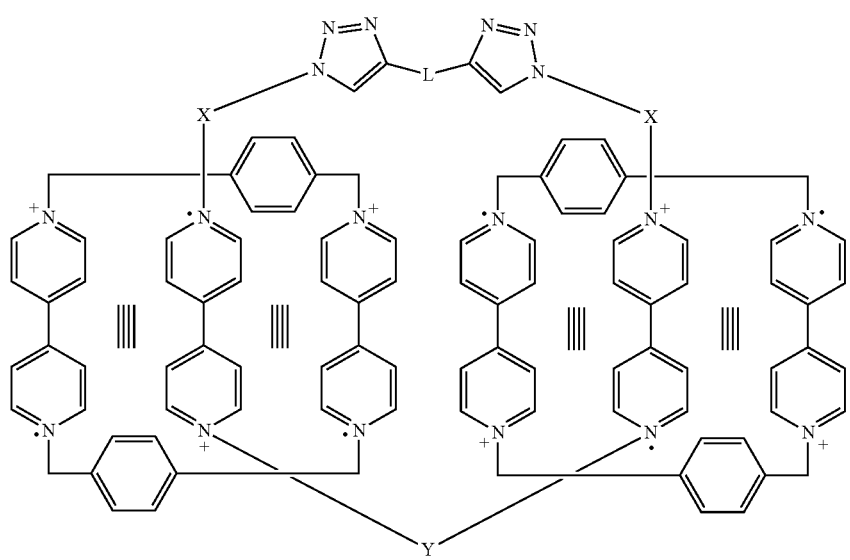
(Formula IIb)
or
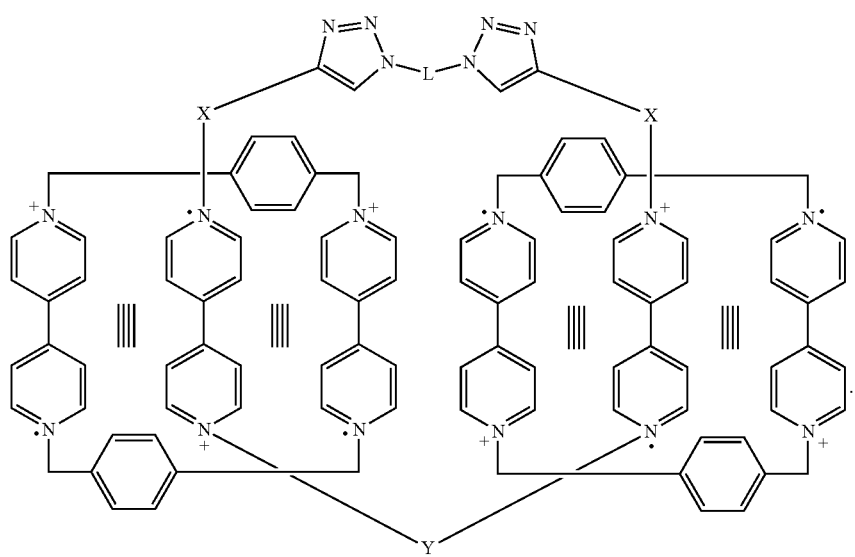
(Formula IIc)

X may comprise an alkyl, an alkenyl, an aryl, an alkylaryl, a triazole, or an alkyltriazole and Y may comprise an alkyl, an alkenyl, an aryl, an alkylaryl, a triazole, or an alkyltriazole.

The X-triazole-L-triazole-X linker and the Y linker may be any suitable length. In some embodiments, X-triazole-L-triazole-X linker of Formulas Ib, Ic, IIb or IIc may comprise a continuous bridge of 8, 9, 10, 11, or 12 atoms. In some embodiment, Y linker of Formulas Ib, Ic, IIb or IIc may comprise a continuous bridge of 8, 9, 10, 11, or 12 atoms. In certain embodiment, X-triazole-L-triazole-X linker and the Y linker of Formulas Ib, Ic, IIb or IIc may comprise a continuous bridge of 8, 9, 10, 11, or 12 atoms. In some embodiments, X may comprise —$(CH_2)_{nx}$— where nx is 0, 1, 2, 3, or 4. In some embodiments, Y may comprise —$(CH_2)_{nl}$— where nl is 0, 1, 2, 3, or 4. In some embodiments, Y may comprise —$(CH_2)_{ny}$— where ny is 8, 9, 10, 11, or 12. In certain embodiments, X may comprise —$(CH_2)_{nx}$— where nx is 0, 1, 2, 3, or 4, L may comprise —$(CH_2)_{nl}$— where nl is 0, 1, 2, 3, or 4, and, Y may comprise —$(CH_2)_{ny}$— where ny is 8, 9, 10, 11, or 12. In particular embodiments, nx=1 or 2, nl=1 or 2, and ny=9 or 11.

Crystalline compositions may be prepared from the [3]catenanes described herein. The crystalline composition may comprise any of the [3]catenanes described above. In some embodiments, the composition further comprises a counter anion, e.g., $PF_6^-$ as used in the Examples that follow. The counter anion may be provided to balance the charge of the [3]catenane, including having a molar ration of counter anion to [3]catenane from about 12:1 to 6:1 or anything in between.

Synthesis of [3]Catenane

Figure 9:
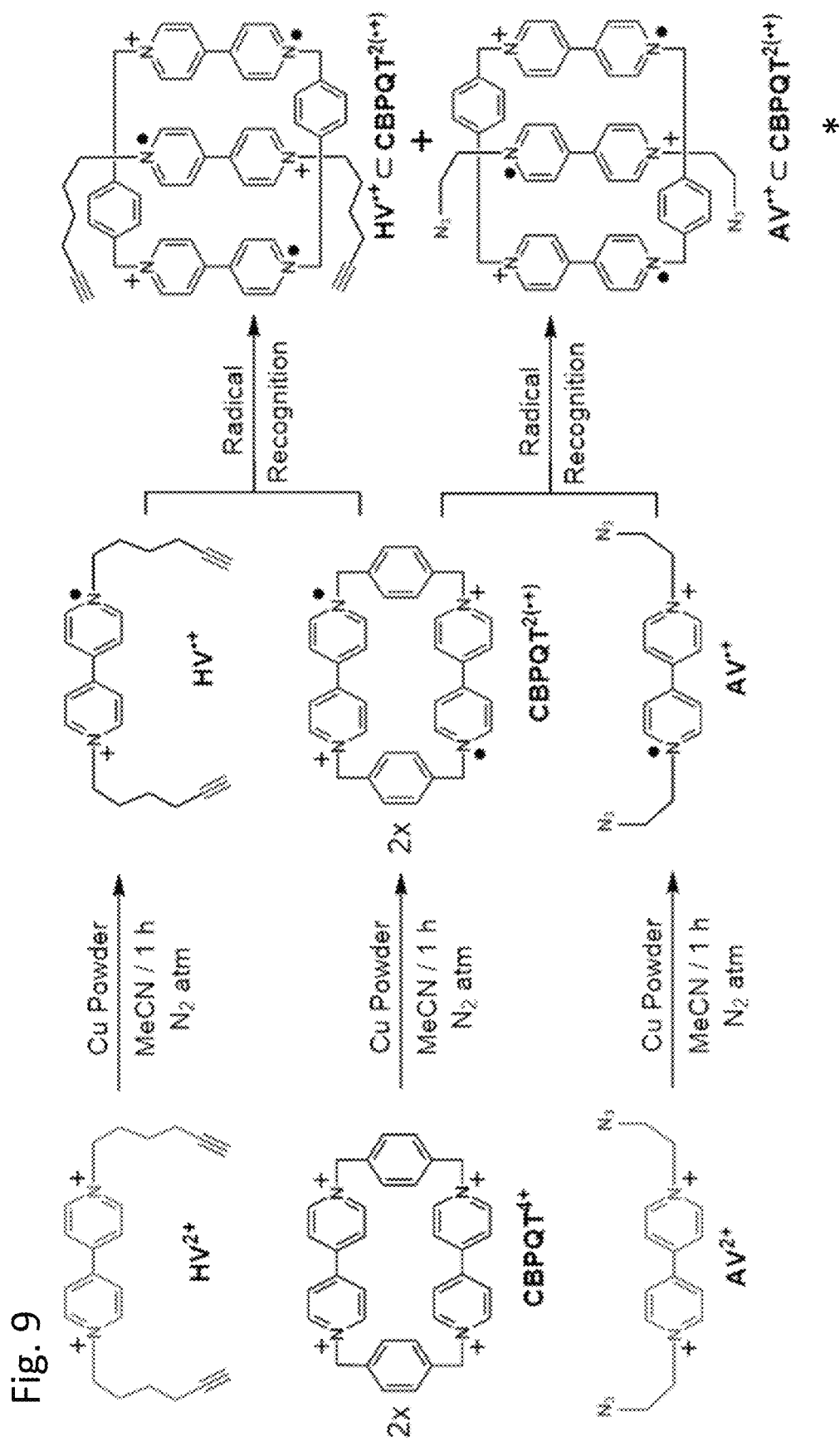
FIG. 9. Illustration of Scheme 1. Preparation of [3]C12+ and [3]C6(.+) via ring-closing of a [3]pseudorotaxane prepared from two [2]pseudorotaxanes. * indicates where the FIG. 9 drawings meet.
Figure 9:
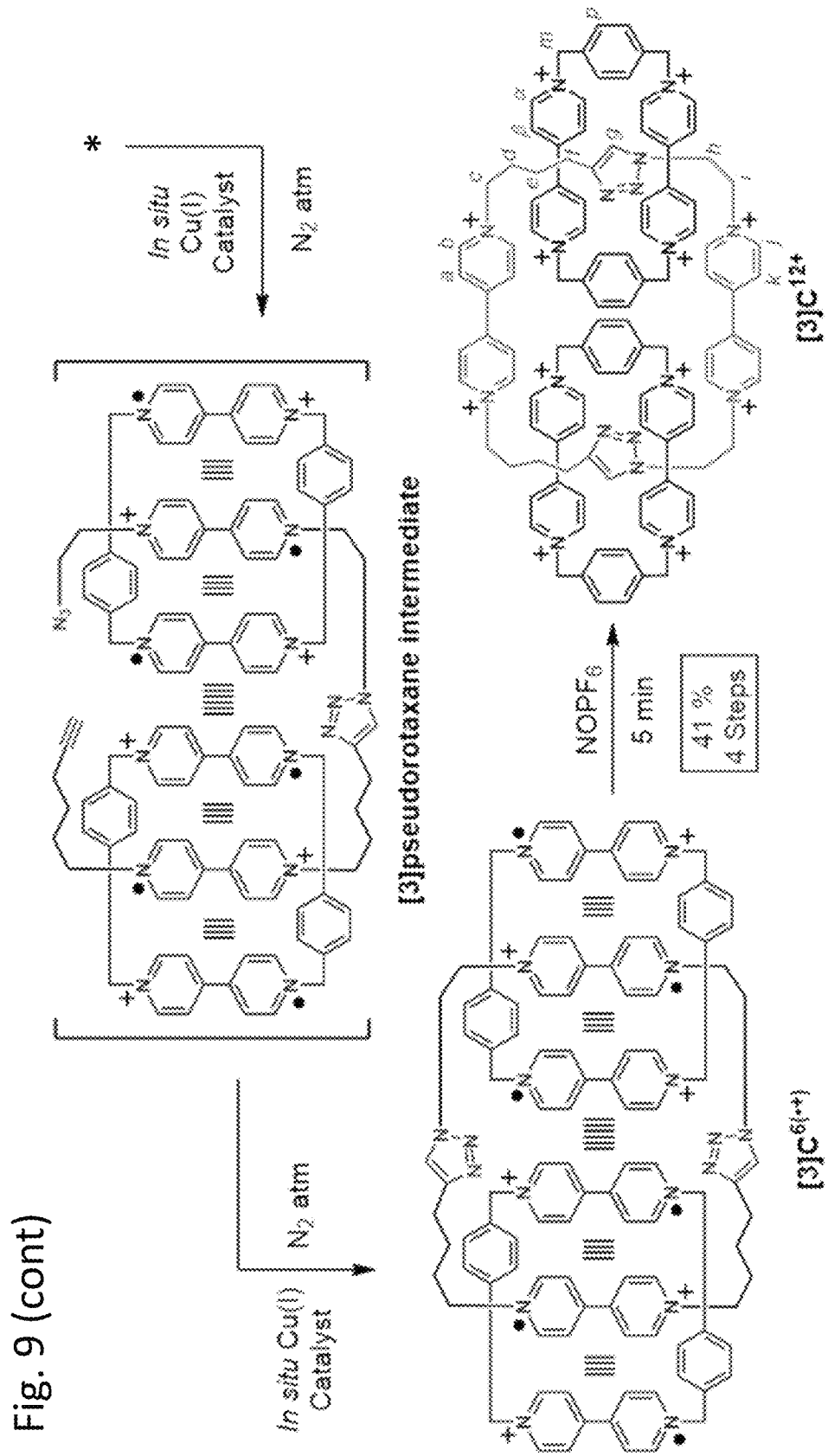
Figure 10:
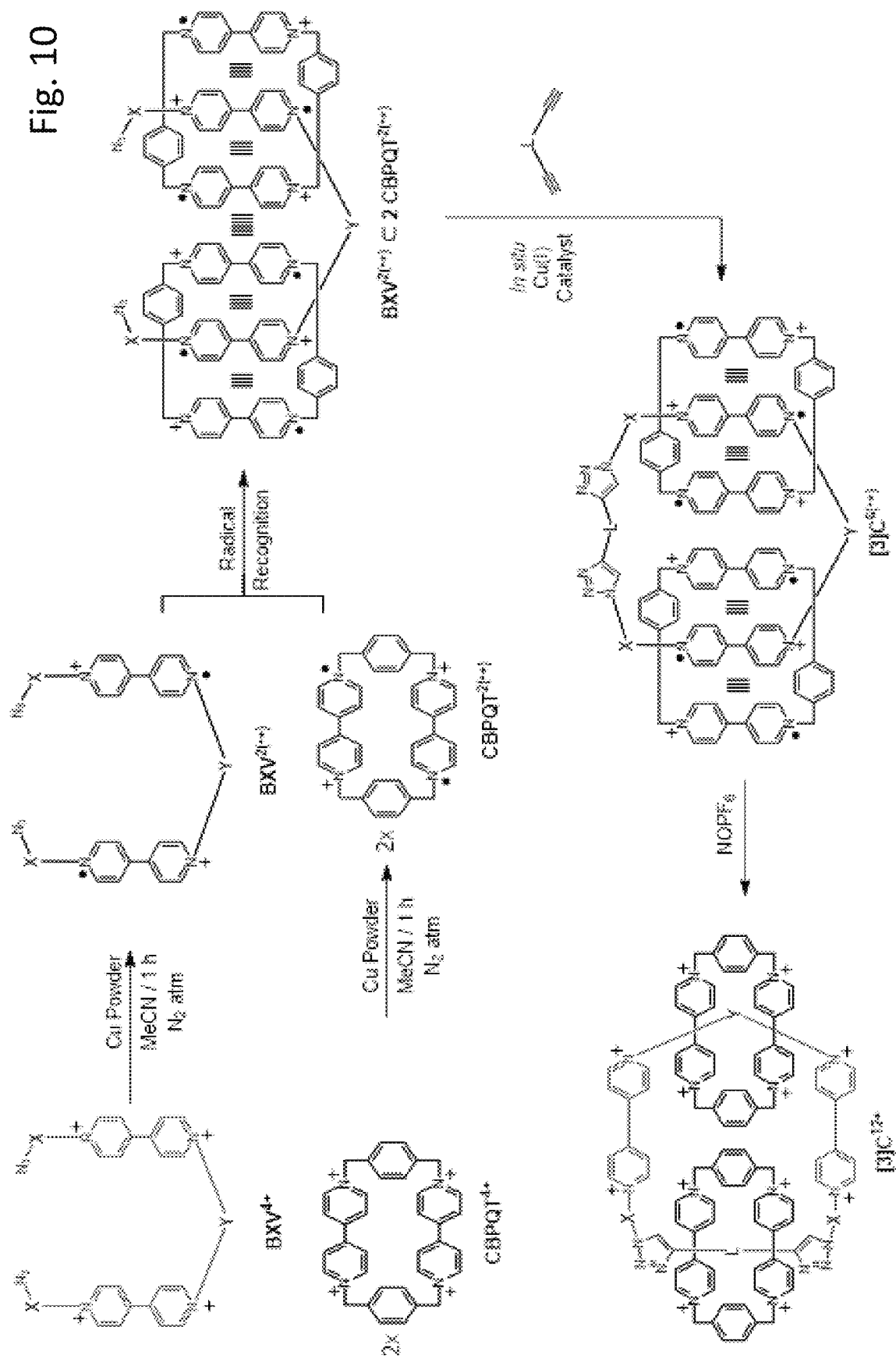
FIG. 10. Illustration of Scheme 2. Preparation of $[3]C^{12+}$ and $[3]C^{6(.+)}$ via ring-closing of a [3]pseudorotaxane.
Figure 11:
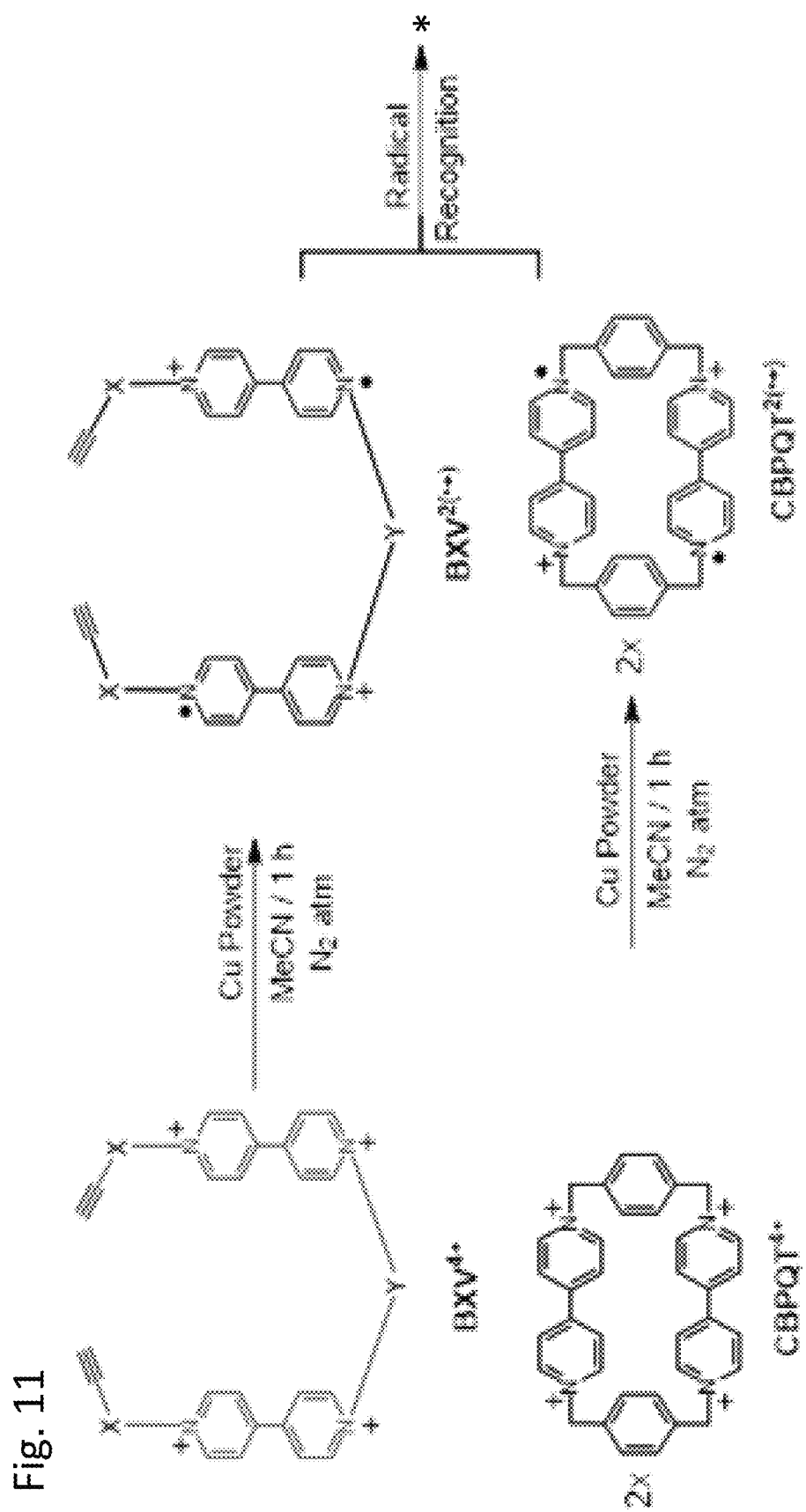
FIG. 11. Illustration of Scheme 3. Preparation of $[3]C^{12+}$ and $[3]C^{6(.+)}$ via ring-closing of a [3]pseudorotaxane. * indicates where the FIG. 11 drawings meet.
Figure 11:
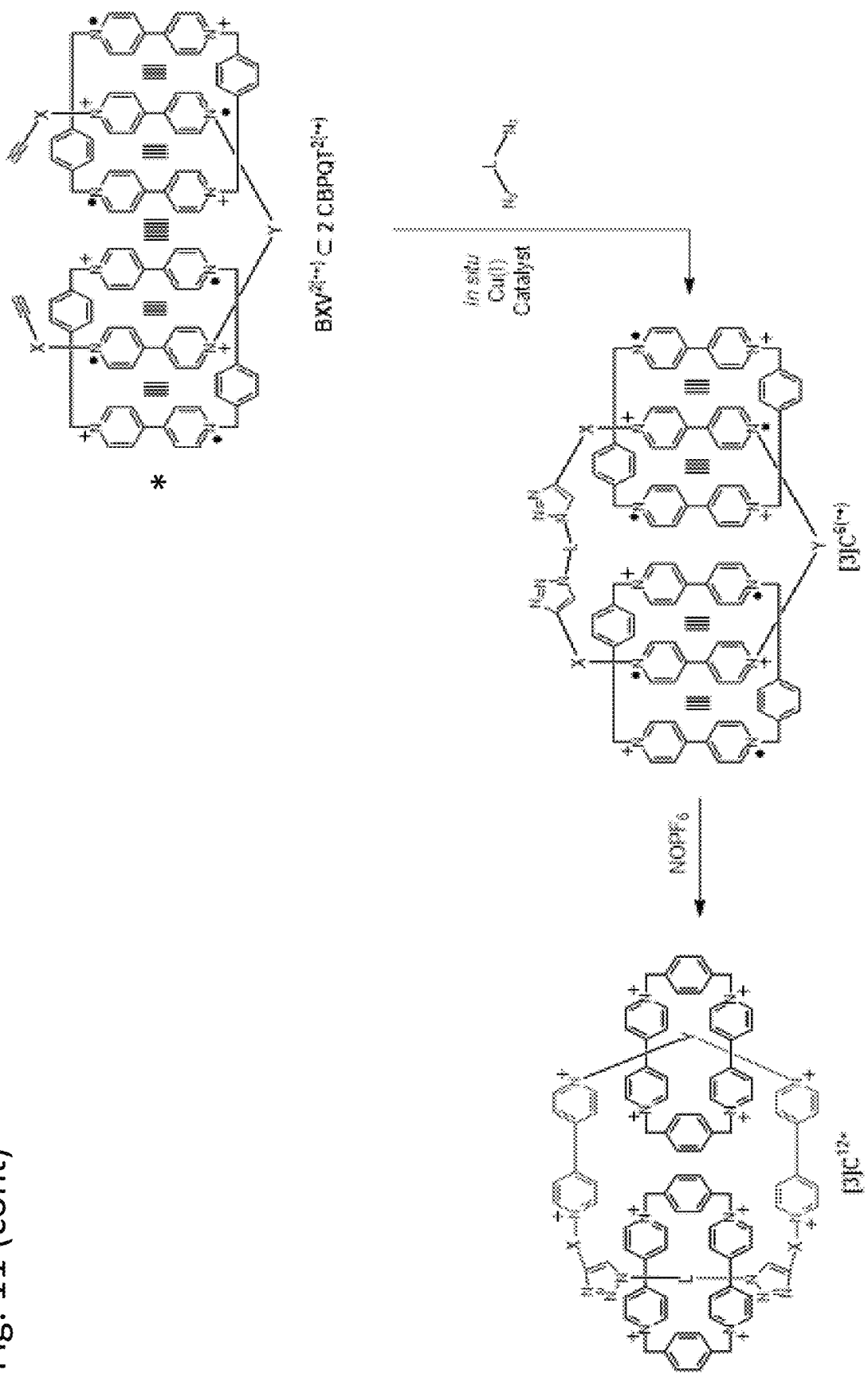

Another aspect of the invention is methods of preparing [3]catenanes. Exemplary methods for preparing [3]catenanes are provided in Schemes 1-3 (FIGS. 9-11). The method comprises ring-closing a [3]pseudorotaxane to prepare the [3]catenane. The [3]pseudorotaxane comprises a threading component threading two diradical/dicationic rings, and the threading component comprises two viologen subunits between terminal moieties that each comprise a click-functionalized moiety. The method also comprises contacting a click-functionalized terminal moiety with a corresponding click-functionalized moiety to form a central diradical/dicationic ring mechanically interlocking the two diradical/dicationic rings. The two diradical/dicationic rings may each comprise cyclobis(paraquat-p-phenylene) bisradical dication ($CBPQT^{2(\cdot+)}$).

The click-functionalized moiety may be any click-functionalized moiety. In some embodiments, the [3]pseudorotaxane comprises one azide terminal moiety or two azide terminal moieties. In some embodiments, the [3]pseudorotaxane comprises one alkynyl terminal moiety or two alkynyl terminal moieties. In yet another embodiment, the [3]pseudorotaxane comprises one alkynyl terminal moiety and one azide terminal moiety. Ring-closing via a click reaction results in the macrocyclic component of Formula II as described above.

As shown in Scheme 1 (FIG. 9), a [3]catenane may be formed by ring-closing the [3]pseudo rotaxane

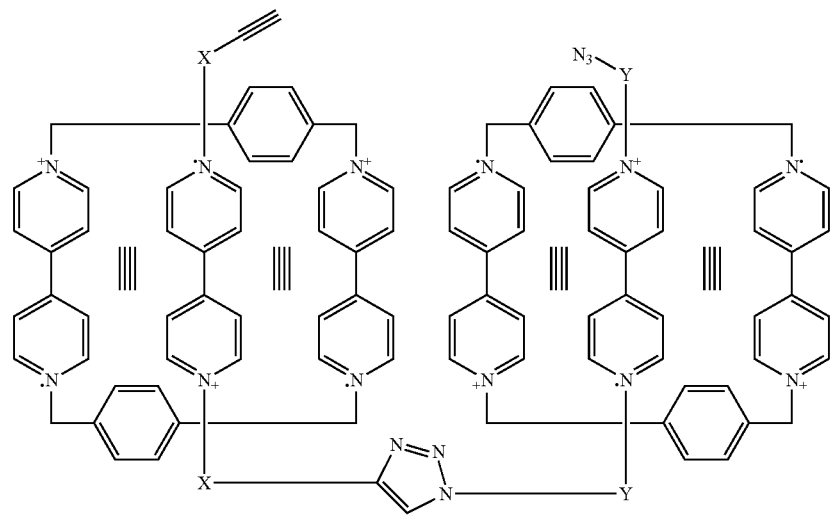

(Formula IIIa)

When the azide terminal moiety is contacted with the alkynyl terminal moiety, the central diradical/dicationic ring is formed mechanically interlocking the $CBPQT^{2(\cdot+)}$ rings to form the [3]catencane of Formula IIa. The [3]catenane of Formula IIa may be oxidized to form the [3]catencane of Formula Ia.

The [3]pseudorotaxane may be prepared from reaction of a first [2]pseudorotaxane and a second [2]pseudorotaxane.

One of the [2]pseudorotaxanes may comprise a pseudorotaxane of Formula IVa

The other [2]pseudorotaxane comprises a pseudorotaxane of Formula IVb

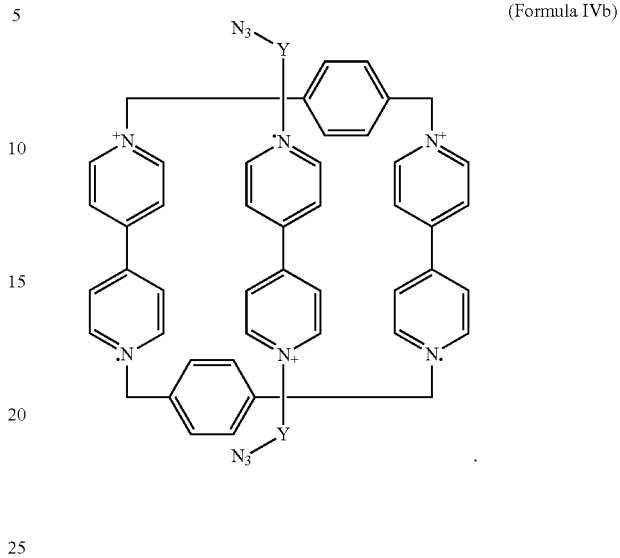

(Formula IVb)

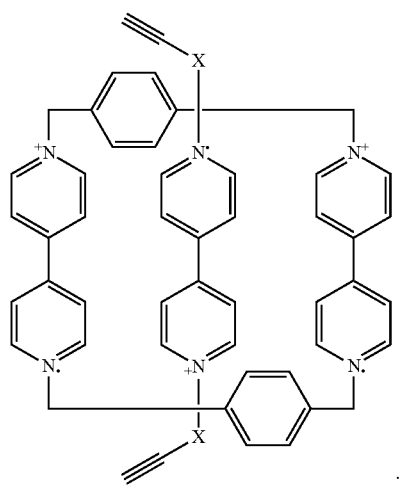

(Formula IVa)

When the azide terminal moiety of a [2]pseudorotaxane reacts with the alkynyl terminal moiety of the other [2]pseudorotaxane, the [3]pseudorotaxane of Formula IIIa is formed.

Alternative methods of preparing the [3]catenane is shown in Schemes 2-3 (FIGS. 10-11). In this embodiment, the [3]pseudorotaxane comprises terminal moieties each comprising the same click-functionalized moiety. The [3]pseudorotaxane may comprise a compound of Formula III or a compound of Formula IIIc

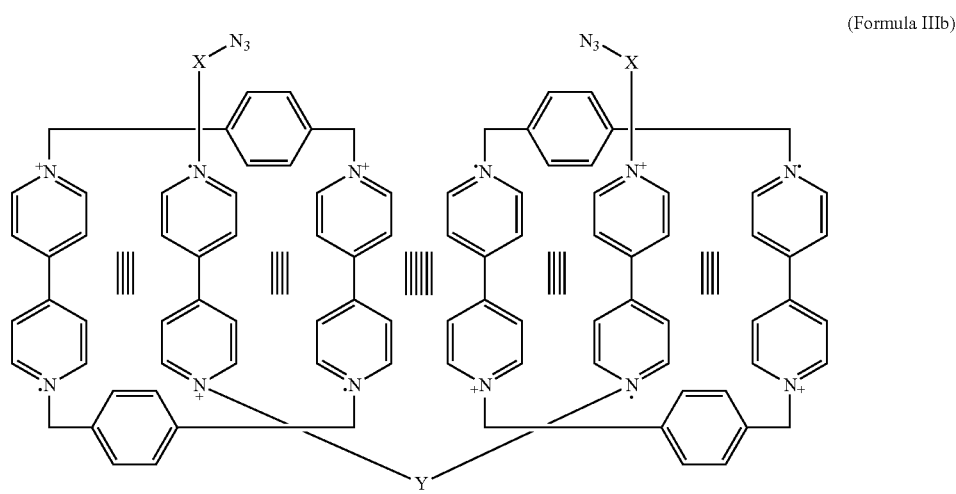

(Formula IIIb)

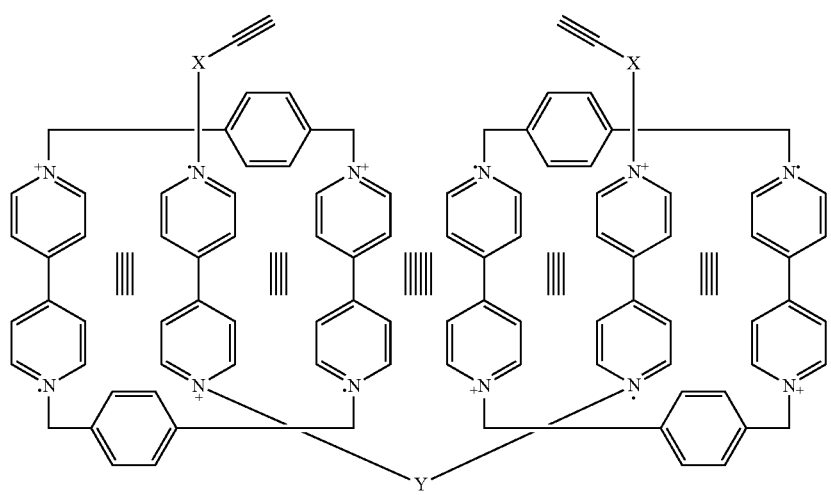

Formula (IIIc)

Ring-closing may be accomplished by reacting the [3]pseudorotaxane of Formula IIIb and Formula IIIc with compounds of Formula Va

(Formula Va)

or (Formula Vb)

respectively. Ring-closing forms the central diradical/dicationic ring to mechanically interlocking the $CBPQT^{2(\cdot+)}$ rings to form the [3]catencane of Formula IIb and IIc. The [3]catenane of Formulas IIb or IIc may be oxidized to form the [3]catencane of Formulas Ib or Ic, respectively.

An exemplary [3]catenane may be prepared from the synthetic scheme shown in Scheme 1 (FIG. 9) and as demonstrated in the Examples. Two trisradical [2]pseudorotaxanes—one azide-functionalized and the other alkyne-functionalized—were synthesized by treating two independent solutions of (i) bis(2-azidoethyl)viologen ($AV^{2+}$) and $CBPQT^{4+}$ and (ii) bis(6-hexynyl)viologen ($HV^{2+}$) and $CBPQT^{4+}$ with Cu powder under an inert atmosphere in a $N_2$-filled glovebox. The complexation between the viologens and their respective $CBPQT^{2(\cdot+)}$ bisradical dication is driven by radical-radical recognition to form $[AV^{(\cdot+)} \subset CBPQT^{2(\cdot+)}]$ and $[HV^{(\cdot+)} \subset CBPQT^{2(\cdot+)}]$ inclusion complexes, which were allowed to coalesce over a period of an hour before the two dark-purple solutions were mixed together. Tandem copper(I)-catalyzed azide-alkyne cycloaddition (CuAAC) reactions then occurred between the two bis(azide)-functionalized and bis(alkyne)-functionalized axles of the two [2]pseudorotaxanes with the lingering copper(I) catalytic species in situ generated from the previous reduction step. The first of the two Click reactions brings together the two [2]pseudorotaxanes to produce a [3]pseudorotaxane intermediate, while the second CuAAC is the ring-closing step, driven by the face-to-face radical interactions between two bipyridinium radical cations of the $CBPQT^{2(\cdot-)}$ subunits of the [3]pseudorotaxanes. This inter-ring recognition, coupled with the high dilution conditions (1.25 mM), resulted in the formation of a more complex mechanically interlocked species, i.e., a [3]catenane, in a hexaradical/hexacationic state. The fully oxidized [3]catenane $[3]C^{12+}$ was obtained either by reacting the reduced-state [3]catenane with nitrosonium hexafluorophosphate ($NOPF_6$), which oxidized all three rings within seconds, or by exposing the dark purple intermediate in air overnight. The formation of all the radical intermediates (Scheme 1; FIG. 9) was monitored by mass spectrometry, UV-vis-NIR spectroscopy, and single-crystal X-ray diffraction when possible. Upon purification by reverse-phase flash chromatography ($C_{18}$: water/acetonitrile, 0.1% TFA—trifluoroacteic acid) and counterion exchange ($NH_4PF_6/H_2O$) to give $[3]C.12PF_6$ which was obtained in 41% yield overall. The identity and purity of the [3]catenane were confirmed by high-resolution electrospray mass spectrometry (HR-ESI-MS) and analytical high performance liquid chromatography (HPLC, FIG. 8B), respectively.

The $^1H$ and $^{13}C$ (data not shown) nuclear magnetic resonance (NMR) spectra of $[3]C.12PF_6$, recorded in $CD_3CN$ at 298 K (FIG. 1D), support the proposed structure of $[3]C^{12+}$ in solution with all the $^1H$ and $^{13}C$ assignments being confirmed by two-dimensional NMR measurements (data not shown). The $^1H$ NMR spectrum (FIG. 1D) of $[3]C.12PF_6$ reveals that the two equivalent $CBPQT^{4+}$ rings are located on the 1-(1-(ethylene)-1H-1,2,3-triazole-4-yl) butylene linkers in the central $TB^{4+}$ ring and undergo slow pirouetting motions at room temperature as indicated by the broadening of all the $^1H$ $CBPQT^{4+}$ resonances. The $^1H$ NMR spectrum (FIG. 1A) of $[3]C.12PF_6$, recorded at 343 K, reveals that these resonances for the two $CBPQT^{4+}$ ring protons become much better resolved as a result of fast exchange (i) associated with the facile pirouetting of the $CBPQT^{4+}$ rings around the linkers and (ii) supplemented, most likely, by rapid rotation along the axes of the bipyridinium and phenylene units within the $CBPQT^{4+}$ rings.

The characteristics of the mechanically interlocked structure of $[3]C.12PF_6$ emerge clearly when comparing its $^1H$ NMR spectrum (FIG. 1A) with those (FIG. 1B-C) of its non-interlocked macrocyclic counterparts—$CBPQT.4PF_6$ (FIG. 1C) and $TB.4PF_6$ (FIG. 1B), which is synthesized from $AV.2PF_6$ and $HV.2PF_6$ using traditional CuAAC conditions. There are significant upfield shifts in the resonances associated with the methylene protons of the triazole linkers in [3]$C^{12+}$ compared to those in $TB^{4+}$. For example, the chemical shifts for protons $H_d$, $H_e$, and $H_f$ change from 2.76, 2.06 and 1.63 ppm in the free macrocycle ($TB^{4+}$) to 1.30, −0.36 and −0.46 ppm, respectively, in the interlocked [3]catenane [3]$C^{12+}$. This evidence supports strongly the significant change in the local electronic environment induced by the constrained $CBPQT^{4+}$ cations within the [3]catenane.

Unambiguous evidence for the constitution of the [3]catenane is achieved from X-ray crystallographic analysis of single crystals obtained by slow diffusion of diisopropyl ether into an MeCN solution of [3]C.12$PF_6$. The solid-state structure (FIG. 2A-2J) confirms the topology and 12 positive charges (by counting the anions) associated with the dodecacationic [3]catenane where the two $CBPQT^{4+}$ rings are mechanically interlocked to a central $TB^{4+}$ macrocycle. The three tetracationic rings aligns themselves in a collinear fashion in which their centroids lie almost in a straight line. The compactness of the [3]$C^{12+}$ dodecacation is illustrated in FIG. 2D-2J by space-filling representations, where it becomes apparent that there is little or no free space between the two $CBPQT^{4+}$ rings with a 3.2 Å plane-to-plane separation between their closest phenylene units. This separation is considerably shorter than the range (3.3-4.0 Å) of distances associated with typical π-π interactions. As a result of the compact mechanically interlocked structure, the six bipyridinium ($BIPY^{2+}$) units in [3]$C^{12+}$ exhibit much smaller torsional angles (mean angle=17°) than those found for BIPY units in isolated $CBPQT^{4+}$ (40°) and/or $TB^{4+}$ (73° free macrocycles.

Figure 3A:
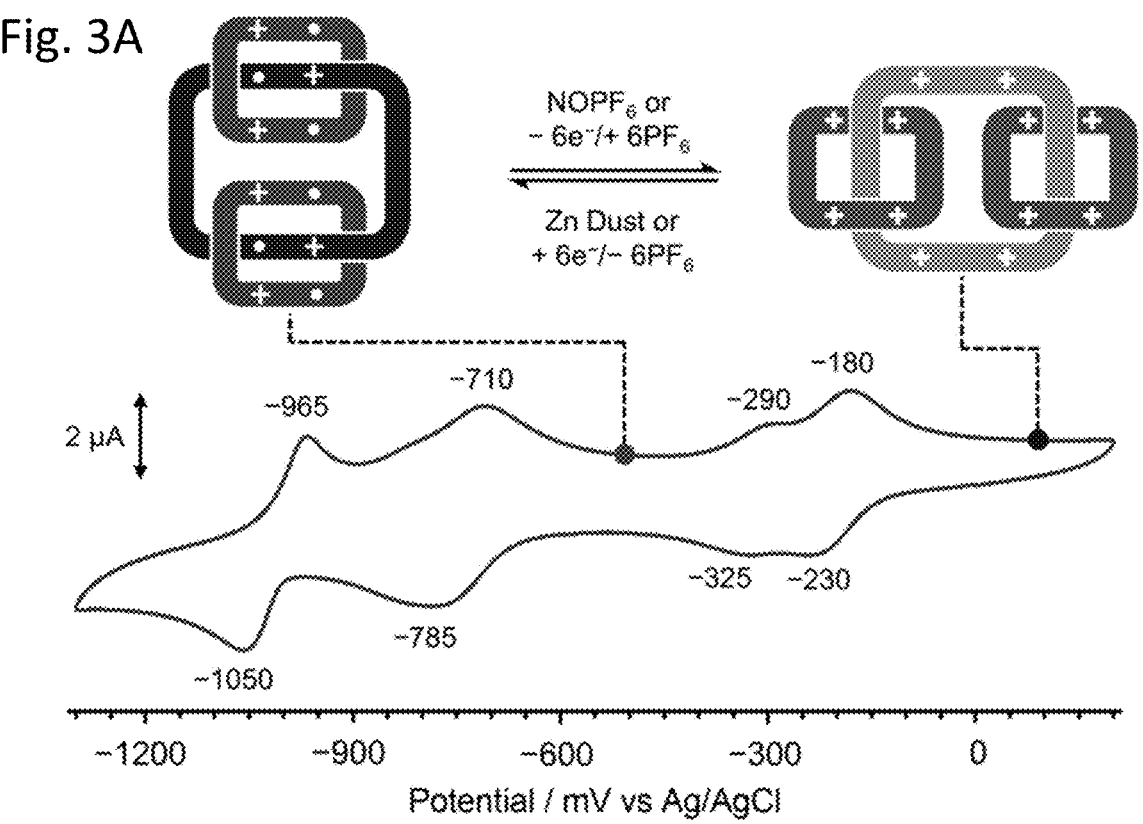
FIGS. 3A-3B. Reversible switching between $[3]C^{12+}$ and $[3]C^{6(.+)}$.

The six bipyridinium units in the [3]catenane offer a possibility of the dodecacation taking up a total of 12 electrons in a system with potentially 13 redox states. Cyclic voltammetry of [3]$C^{12+}$ revealed (FIG. 3A), however, that the two most prevalent redox states characterized by widely separated potential windows are the dodecacationic [3]$C^{12+}$ form and the hexaradical/hexacationic [3]$C^{6(.+)}$ form. These two states can be interconverted reversibly by means of both electrochemical (FIG. 3A) and chemical (FIG. 3B-3D) stimuli. Treatment (298 K/20 min) of [3]C.12$PF_6$ in MeCN with Zn dust resulted in a characteristic color change from colorless to dark purple, indicating the formation of [3]$C^{6(.+)}$. This color change was corroborated by air-free ESI-MS experiments (FIG. 4AI-4AII) in which prominent peaks, corresponding to [[3]$C.6PF_6$-n$PF_6$]$^{n+}$ (n=3-5), were observed. The reverse process ([3]$C^{6(.+)}$ to [3]$C^{12+}$) occurs within seconds on treating the hexaradical hexacation [3]$C^{6(.+)}$ with $NOPF_6$. Reversible switching can be repeated by up to five times as confirmed (FIG. 3B-3D) by UV-vis-NIR spectroscopy.

X-Ray diffraction analysis (FIG. 4B-4J) of a single crystal, grown by vapor diffusion of diisopropyl ether into an MeCN solution of [3]C.6$PF_6$ in an $N_2$-filled glovebox, confirms the constitution of [3]$C^{6(.+)}$, but reveals a marked difference in topology from that of its oxidized [3]$C^{12+}$ form. The two $CBPQT^{2(.+)}$ rings display a change in their relative geometries when compared with their fully oxidized states in the [3]$C^{12+}$ form, i.e., moving from the triazole linkers to encircling the $BIPY^{(.+)}$ unit of the $TB^{2(.+)}$ ring. This change results in an intramolecular π-π interaction across the six adjacent viologen radical cations with an average plane-to-plane distance of 3.24 Å. All the $BIPY^{(.+)}$ units become flattened in comparison to their corresponding $BIPY^{2+}$ units in [3]$C^{12+}$. The mean torsional angle in the $BIPY^{(.+)}$, which is 3.6°, further corroborates the presence of radical cationic states for these $BIPY^{(.+)}$ units. The changes in the relative dispositions of the three rings in [3]$C^{12+}$ and [3]$C^{6(.+)}$—wherein electron sharing and delocalization among the $BIPY^{n./(2-n)+}$ (n=0 or 1) units are only present in [3]$^{C6(.+)}$—may explain the smaller number of observed redox states found in this [3]catenane, compared to the previously reported homo[2]catenane, wherein the two $CBPQT^{n./(4-n)+}$ (n=0-2) rings are rigid and retain the same relative dispositions, irrespective of the different redox states. At the supramolecular level, the hexaradical/hexacations [3]$C^{6(.+)}$ assemble (FIG. 4F) into 2D layers wherein the $CBPQT^{2(.-)}$ rings are located in a single plane within each layer driven by the intermolecular interactions between both BIPY-to-BIPY and phenylene-to-phenylene pairs.

Tetracosacationic and Dodecaradical/Dedecacationic Radial [5]Catenanes

Tetracosacationic and dodecaradical/dedecacationic r[5]catenanes may be prepared from the reaction of [3]pseudorotaxanes as described above. As will be shown in the Examples below, the tetracosacationic and dodecaradical/dedecacationic r[5]catenanes may be reversibly interconverted between the different oxidation states as well as molecular topologies.

Figure 5B:
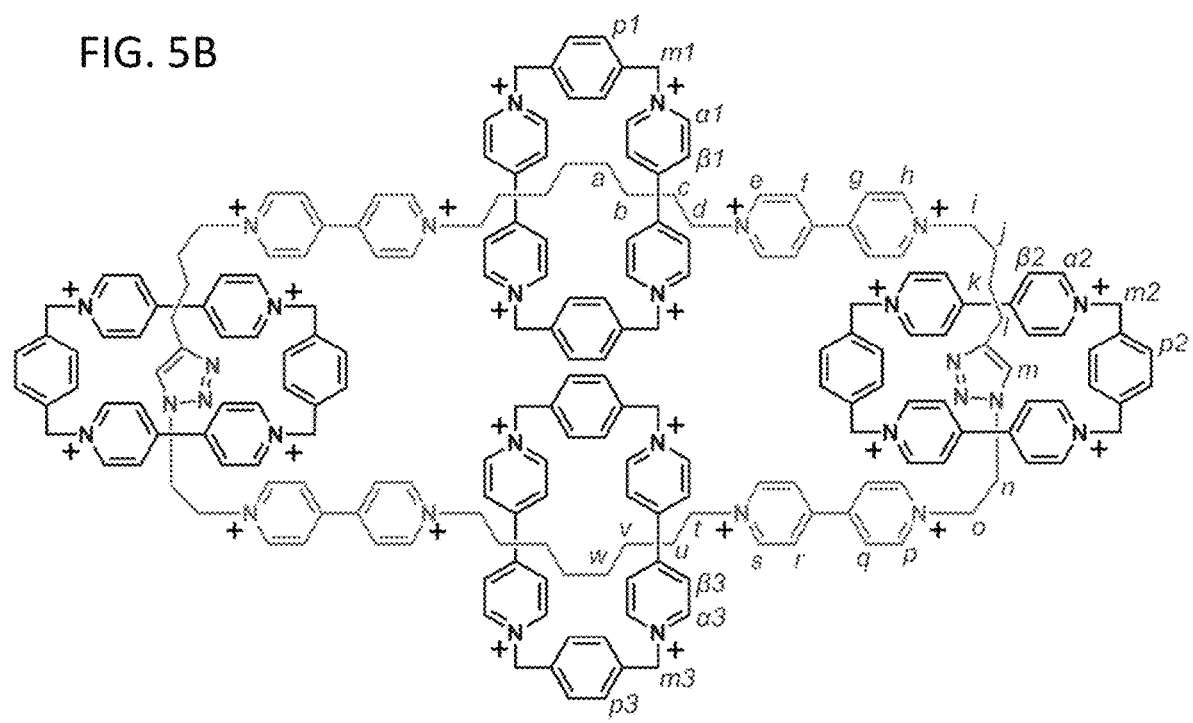

The tetracosacationic r[5]catenane comprises a central octacationic ring mechanically interlocked with a second tetracationic ring, a third tetracationic ring, a fourth tetracationic ring, and a fifth tetracationic ring. An exemplary r[5]$C^{24+}$ is provided in FIG. 5B.

The dodecaradical/dedecacationic r[5]catenane comprises a central tetraradical/tetracationic ring mechanically interlocked with a second diradical/dicationic ring, a third diradical/dicationic ring, a fourth diradical/dicationic ring, and a fifth diradical/dicationic ring.

Each of the linkers $R^1$ and $R^2$ may comprise a triazole group prepared from azide-alkyne click reactions between the terminal moieties of the [3]pseudorotaxanes. Each of the linkers $L^1$ and $L^2$ may be independently selected from an alkyl, an alkenyl, an aryl, an alkylaryl, a triazole, or an alkyltriazole. Suitable linkers for each of $R^1$, $R^2$, $L^1$, and $L^2$ are described above and those of skill in the art may make particular selections based upon the teachings herein.

The tetracation ring may comprise cyclobis(paraquat-p-phenylene) tetracation ($CBPQT^{4+}$). The diradical/di cation ring may comprise cyclobis(paraquat-p-phenylene) diradical/dication ($CBPQT^{2(.+)}$).

Reversible switching between the fully oxidized tetracosacationic [24+] and the halfway-reduced dodecaradical/dodecacationic [12(.+)] states was also promoted in the case of the radial [5]catenane by both chemical and electrochemical means. Upon the reduction of r[5]$C^{24+}$ with Zn dust, the formation of the r[5]$C^{12(.+)}$ species can be monitored (FIG. 7A) by UV-Vis spectroscopy with a characteristic absorption band at 1116 nm. The identity of this dodecaradical/dodecacationic radial [5]catenane, which could be facilely converted back to r[5]$C^{24+}$ by an oxidation with $NOPF_6$, was confirmed by the air-free ESI-MS, wherein prominent peaks were observed at m/z=1512.8240 and 1098.3773, corresponding to the [M-n$PF_6$]$^{n+}$ peaks with n=3 and 4, respectively. Electrochemical studies on r[5]C.24$PF_6$ lend (FIG. 7B) the reversible inter-conversion between the two dodecaradical/dodecacationic and tetracosacationic states, in which CV scans can be repeated several times without any changes (FIG. 7C-7D) of the peak currents.

Synthesis of [5]Catenane

Figure 12:
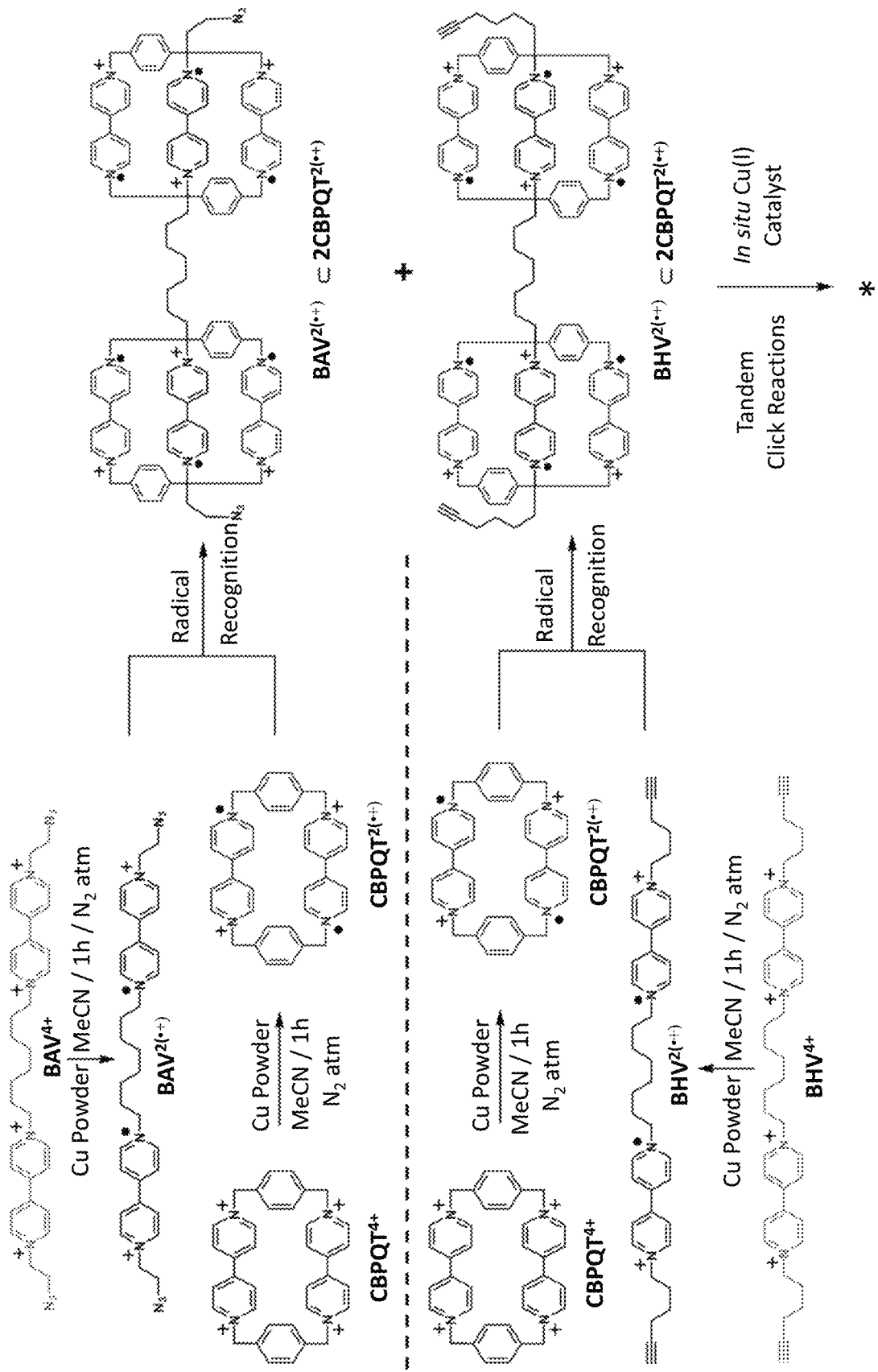
FIG. 12. Illustration of Scheme 4. Preparation of $r[5]C^{z+}$ and $r[5]C^{12(.+)}$ via ring-closing of a [5]pseudorotaxane prepared from two [3]pseudorotaxanes. * indicates where the FIG. 12 drawings meet.
Figure 12:
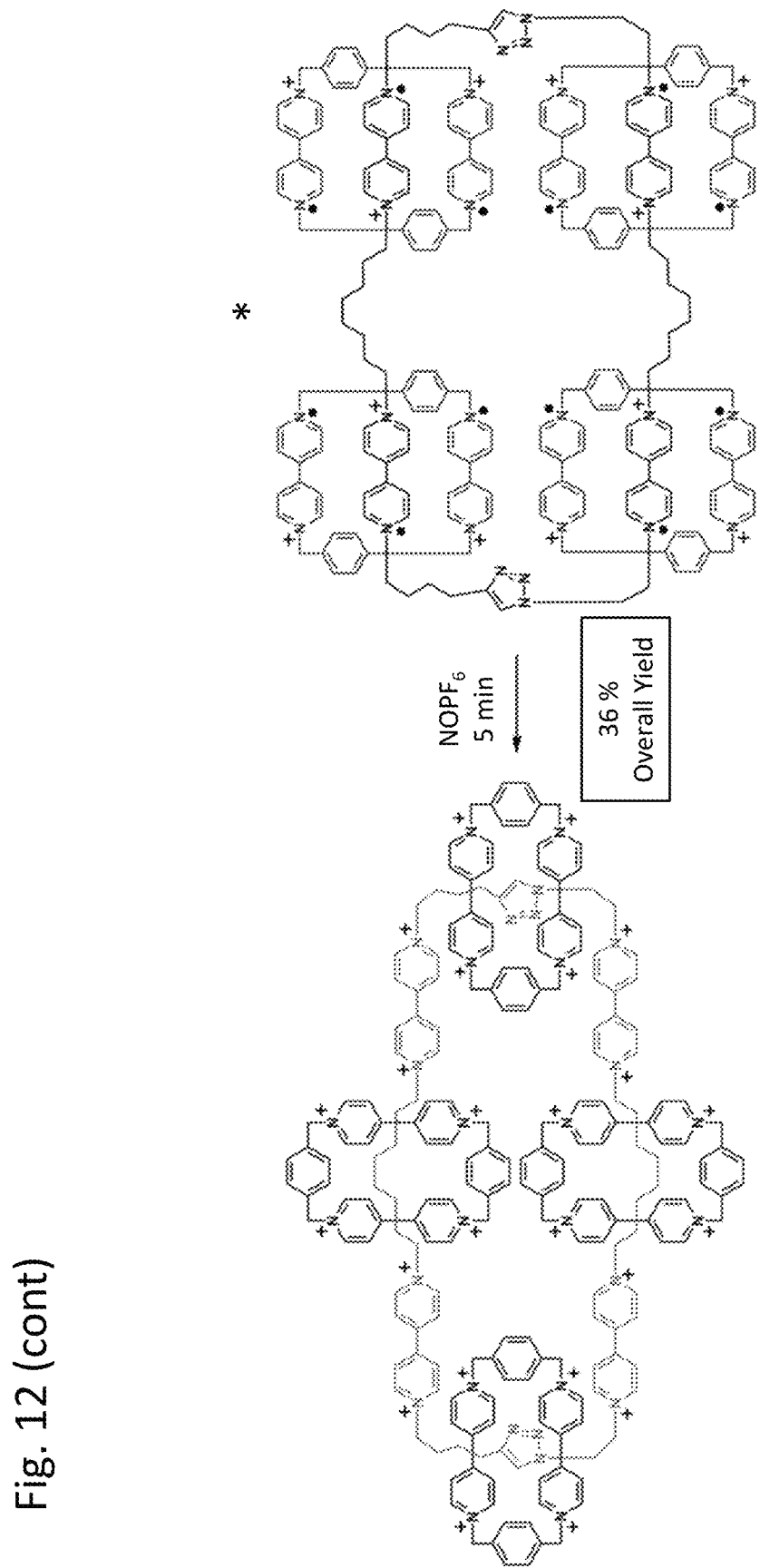

Another aspect of the invention is methods of preparing [5]catenanes. Exemplary methods for preparing [5]catenanes are provided in Scheme 4 (FIG. 12). The method comprises reacting two [3]pseudorotaxanes to prepare the [5]catenane. The [3]pseudorotaxane comprises a threading component threading two diradical/dicationic rings, and the threading component comprises two viologen subunits between terminal moieties that each comprise a click-functionalized moiety. The method also comprises contacting a click-functionalized terminal moiety with a corresponding click-functionalized moiety to form a central diradical/dicationic ring mechanically interlocking the two diradical/dicationic rings. The two diradical/dicationic rings may each comprise cyclobis(paraquat-p-phenylene) bisradical di cation (CBPQT$^{2(.+)}$).

The click-functionalized moiety may be any click-functionalized moiety. In some embodiments, the [3]pseudorotaxane comprises two azide terminal moiety or two alkynyl terminal moieties. Ring-closing via a click reaction results in the macrocyclic component of Formula V as described above.

In particular embodiments, [3]pseudorotaxanes comprising a compound of Formula IIIb X of either of the [3]pseudorotaxanes may comprises an alkyl, alkenyl, aryl, alkylaryl, triazole, or alkyltriazole as described above. Y of either of the [3]pseudorotaxanes may comprise an alkyl, alkenyl, aryl, alkylaryl, triazole, or alkyltriazole. Suitably linkers are described above.

Employing the radical-templated synthetic strategy that was used to make [3]C$^{12+}$, we have been able to synthesize (FIG. 5) a radial [5]catenane r[5]C$^{24+}$—which can also be named a [5]molecular necklace—bearing up to 24 positive charges within its co-constitution. Two bis-viologen axles, BAV$^{4+}$ and BHV$^{4+}$, with octamethylene spacers between the two viologen units were used to drive the formation of two pseudo[3]rotaxanes with bisradical dicationic CBPQT$^{2(.+)}$ rings under reducing conditions. The tandem click reactions between these two pseudo[3]rotaxanes, catalyzed by the in situ generated Cu(I) species, followed by oxidation with NOPF$_6$, gave r[5]C$^{24+}$ in 36% overall yield. The use of Cu$^0$ powder as both a reducing agent and a catalytic precursor for

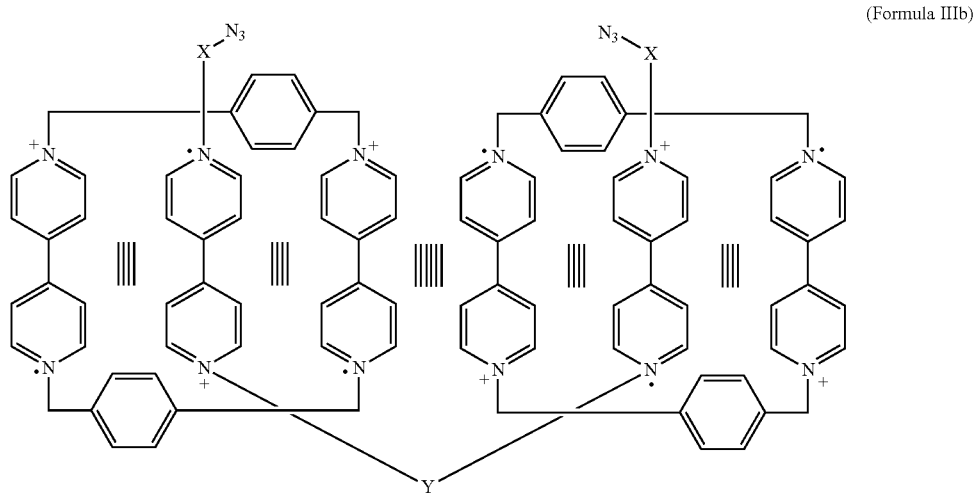

(Formula IIIb)

and the second [3]pseudorotaxane comprises a pseudorotaxane of Formula IIIc the click reactions together with the triazole-based ETB linkers to facilitate the cyclization of the central ring, has

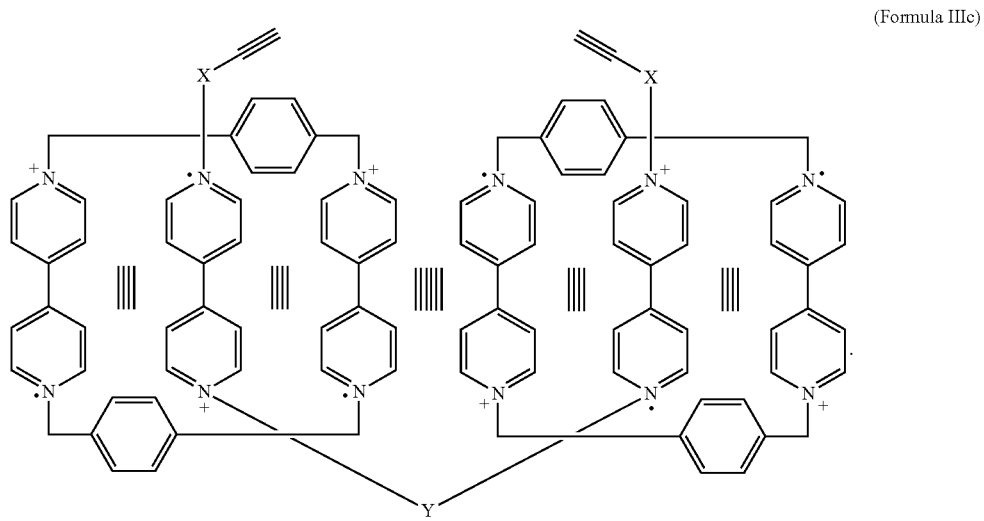

(Formula IIIc)

been shown, yet again, to be an effective way for the production of highly charged MIMs.

Figure 6A:
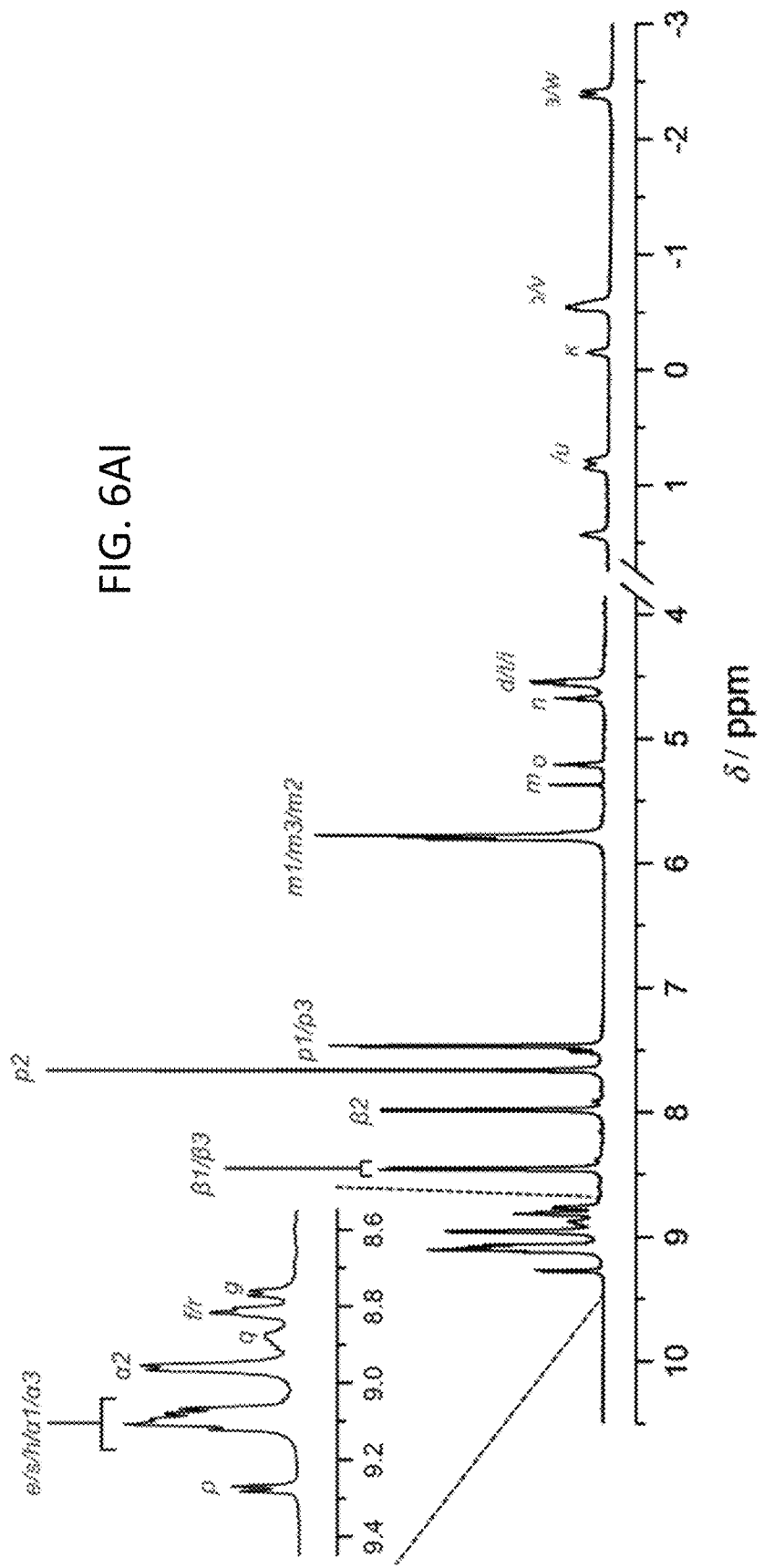
FIGS. 6AI-6AII. Structural characterization of $r[5]C^{24+}$.
Figure 6C:
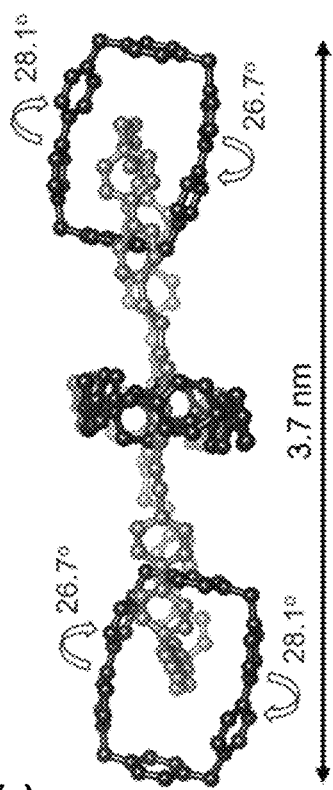
FIGS. 6B-6D. Solid-state structures of $r[5]C^{24+}$ deduced from single-crystal X-ray crystallography.
Figure 6D:
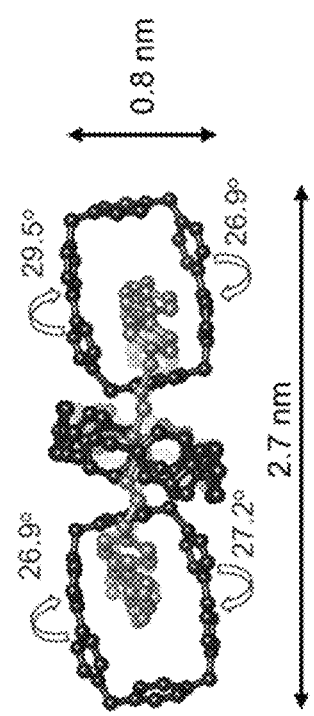
Figure 6B:
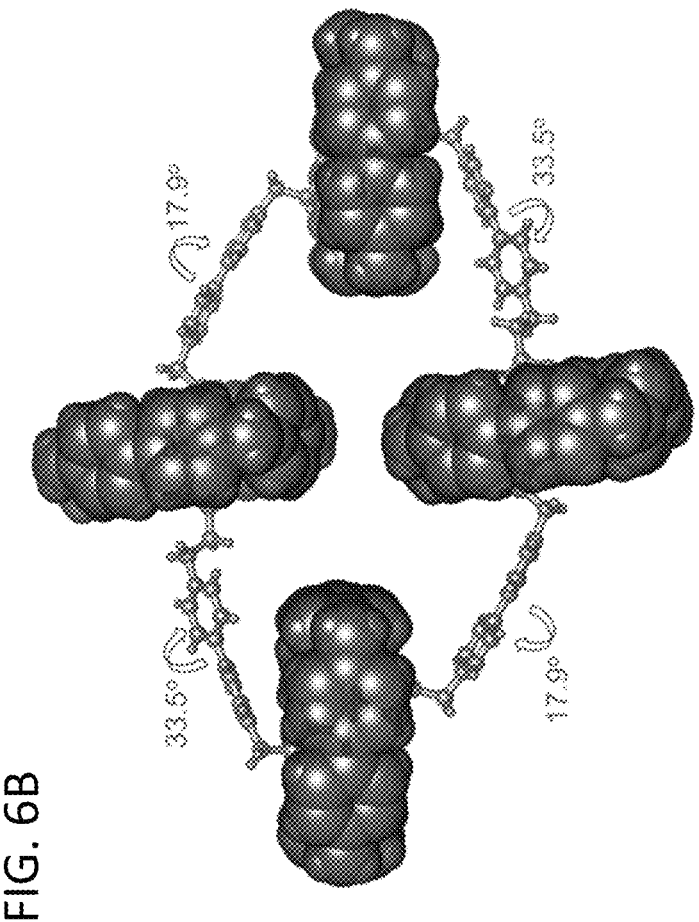

The mechanically interlocked nature of the radial [5]catenane r[5]C$^{24+}$ was established by NMR spectroscopy. The $^1$H NMR spectrum (FIG. 6AI) of r[5]C.24PF$_6$, recorded in CD$_3$CN at 298 K, reveals significant upfield chemical shifts for methylene protons associated with the octamethylene chains and the triazole-based ETB linkers. In particular, the dramatic shielding of protons H$_q$ (δ=−2.37 ppm) and H$_w$ (δ=−2.41 ppm) on the two octamethylene chains indicates their encirclement by two CBPQT$^{4+}$ rings. The resonances (δ=ca. −0.58 and −0.15 ppm) associated with protons H$_l$ and H$_k$, respectively, suggest that the other two CBPQT$^{4+}$ rings reside on the triazole-based ETB linkers as in the case of [3]C$^{12+}$. The $^1$H NMR spectrum of the radial [5]catenane supports the averaged C$_{2v}$ symmetry of this molecule as demonstrated by (i) a small chemical shift difference (H$_{p1}$ and H$_{p3}$; Δδ=0.1 ppm, FIG. 6AI) for the resonances associated with the phenylene protons in the two CBPQT$^{4+}$ rings encircling the octamethylene chains and (ii) a single set of proton resonances for the two CBPQT$^{4−}$ rings encircling the triazole-based ETB linkers. HR-ESI-MS supports the structural assignment of r[5]C$^{24+}$ as its PF$_6^-$ salt, in which m/z fragments, corresponding to the [M-nPF$_6$]$^{n+}$ species for n=3, 4, and 5, are observed (FIG. 6AII) for the radial [5]catenane along with the loss of three to five PF$_6^-$ counter ions, respectively. The 3D geometry of r[5]C$^{24+}$ was determined unequivocally by X-ray diffraction analysis on single crystals grown by slow diffusion of diisopropyl ether into a MeCN solution of r[5]C.24PF$_6$. FIG. 6B-D illustrate the solid-state structure of r[5]C$^{24+}$, demonstrating clearly the mechanically interlocked nature of the tetracosacationic radial [5]catenane and further supporting the structural assignments from the NMR spectroscopic investigations, as well as the relative location of the four CBPQT$^{4+}$ rings within the co-constitution of this MIM. The tetracosation r[5]C$^{24+}$ with a molecular formula of [C$_{218}$H$_{216}$N$_{30}$]$^{24+}$ exhibits a length of 3.7 nm in one dimension and occupies a volume ca. 4.0 nm$^3$, corresponding to 6.0+ charges/nm$^3$.

SUMMARY

We demonstrate the synthesis and characterization of densely charged catenanes. We synthesized by radical templation a dodecacationic [3]catenane, which consists of three mechanically interlocked 4+ charged rings despite their mutual Coulombic repulsion. This highly (12+) charged [3]catenane has the ability to accept up to 12 electrons and occupies a volume of less than 1.65 nm$^3$, corresponding to 7.3+ charges/nm$^3$ which, to the best of our knowledge, is the highest charge density ever observed in a polycationic organic mechanically interlocked molecule. Moreover, this catenane can be switched either electrochemically or chemically between two stable states, i.e., its dodecationic and hexaradical/hexacationic forms. It turned out to be possible to grow good quality single crystals of these two different redox states, which were shown by X-ray diffraction to exist in two distinct geometries in the solid states. These geometries are the result of circumrotation of the two outer cyclophanes from encircling the triazole linkers to encircling the BIPY$^{(\cdot +)}$ units, following their reduction from CBPQT$^{4+}$ to CBPQT$^{2(\cdot +)}$. The molecular switch is reversible in its operation and can be switched in solution as monitored by UV-vis-NIR spectroscopy. We envision that such redox switching, accompanied by relative geometrical changes, could be harnessed in the development of new stimuli-responsive macromolecular architectures and could be of potential use in molecular electronics which require bistable switching of electron conductance.

The possibility of expanding the radical templation strategy has been realized with the construction of a more complex MIM, namely, a tetracosacationic radial [5]catenane that bears up to 24 positive charges in its co-constitution. With a length of up to 3.7 nm, this redox-active tetracosation has a capability of storing as many as 24 electrons per molecule. Overall, our synthetic approach lays the foundation for exploring highly and densely charged organic materials which could find applications in energy storage technologies where novel oligomeric organic redox-active molecules capable of storing and transferring multiple electrons are highly desired. In particular, these MIMs are potentially well-suited to be incorporated into redox flow batteries utilizing oligomeric organic redox-active materials in size exclusion strategies to overcome membrane cross-contamination and, therefore, improve cell performance.

REFERENCES

Bruns, C. J.; Stoddart, J. F. In *The Nature of the Mechanical Bond: From Molecules to Machines*; John Wiley & Sons, Inc.: 2016.

Xue, M.; Yang, Y.; Chi, X.; Yan, X.; Huang, F. (2015). Development of pseudorotaxanes and rotaxanes: from synthesis to stimuli-responsive motions to applications. Chem. Rev. 115, 7398-7501.

Evans, N. H.; Beer, P. D. (2014). Progress in the synthesis and exploitation of catenanes since the millennium. Chem. Soc. Rev. 43, 4658-4683.

Gil-Ramirez, G.; Leigh, D. A.; Stephens, A. J. (2015). Catenanes: fifty years of molecular links. Angew. Chem. Int. Ed. 54, 6110-6150.

Frisch, H.; Martin, I.; Mark, H. (1953). Zur struktur der polysiloxene. I. Monatsh. Chem. 84, 250-256.

Feringa, B. L. (2017). The art of building small: from molecular switches to motors (Nobel Lecture). Angew. Chem. Int. Ed. 56, 11060-11078.

Stoddart, J. F. (2017). Mechanically interlocked molecules (MIMs)—molecular shuttles, switches, and machines (Nobel Lecture). Angew. Chem. Int. Ed. 56, 11094-11125.

Sauvage, J.-P. (2017). From chemical topology to molecular machines (Nobel Lecture). Angew. Chem. Int. Ed. 56, 11080-11093.

Erbas-Cakmak, S.; Leigh, D. A.; McTernan, C. T.; Nussbaumer, A. L. (2015). Artificial molecular machines. Chem. Rev. 115, 10081-10206.

Li, Z.; Barnes, J. C.; Bosoy, A.; Stoddart, J. F.; Zink, J. I. (2012). Mesoporous silica nanoparticles in biomedical applications. Chem. Soc. Rev. 41, 2590-2605.

Barat, R.; Legigan, T.; Tranoy-Opalinski, I.; Renoux, B.; Peraudeau, E.; Clarhaut, J.; Poinot, P.; Fernandes, A. E.; Aucagne, V.; Leigh, D. A.; Papot, S. (2015). A mechanically interlocked molecular system programmed for the delivery of an anticancer drug. Chem. Sci. 6, 2608-2613.

Asakawa, M.; Iiguchi, M.; Mattersteig, G.; Nakamura, T.; Pease, A. R.; Raymo, F. M.; Shimizu, T.; Stoddart, J. F. (2000). Current/voltage characteristics of monolayers of redox-switchable [2]catenanes on gold. Adv. Mater. 12, 1099-1102.

Collier, C. P.; Mattersteig, G.; Wong, E. W.; Luo, Y.; Beverly, K.; Sampaio, J.; Raymo, F. M.; Stoddart, J. F.; Heath, J. R. (2000). A [2]catenane-based solid state electronically reconfigurable switch. Science 289, 1172-1175.

Green, J. E.; Wook Choi, J.; Boukai, A.; Bunimovich, Y.; Johnston-Halperin, E.; Delonno, E.; Luo, Y.; Sheriff, B.

A.; Xu, K.; Shik Shin, Y.; Tseng, H.-R.; Stoddart, J. F.; Heath, J. R. (2007). A 160-kilobit molecular electronic memory patterned at 1011 bits per square centimetre. Nature 445, 414.

Coskun, A.; Spruell, J. M.; Barin, G.; Dichtel, W. R.; Flood, A. H.; Botros, Y. Y.; Stoddart, J. F. (2012). High hopes: can molecular electronics realise its potential? Chem. Soc. Rev. 41, 4827-4859.

Wasserman, E. (1960). the preparation of interlocking rings: a catenanel. J. Am. Chem. Soc. 82, 4433-4434.

Dietrich-Buchecker, C. O.; Sauvage, J. P.; Kintzinger, J. P. (1983). Une nouvelle famille de molecules: les metallo-catenanes. Tetrahedron Lett. 24, 5095-5098.

Mobian, P.; Kern, J.-M.; Sauvage, J.-P. (2003). A [2]catenane constructed around a Ru(diimine)$^{32+}$ complex used as a template. J. Am. Chem. Soc. 125, 2016-2017.

Fuller, A.-M. L.; Leigh, D. A.; Lusby, P. J.; Slawin, A. M. Z.; Walker, D. B. (2005). Selecting topology and connectivity through metal-directed macrocyclization reactions: a square planar palladium [2]catenate and two noninterlocked isomers. J. Am. Chem. Soc. 127, 12612-12619.

Dietrich-Buchecker, C. O.; Sauvage, J. P.; Kern, J. M. (1984). Templated synthesis of interlocked macrocyclic ligands: the catenands. J. Am. Chem. Soc. 106, 3043-3045.

Wu, C.; Lecavalier, P. R.; Shen, Y. X.; Gibson, H. W. (1991). Synthesis of a rotaxane via the template method. Chem. Mater. 3, 569-572.

Megiatto, J. D.; Schuster, D. I. (2008). General method for synthesis of functionalized macrocycles and catenanes utilizing "click" chemistry. J. Am. Chem. Soc. 130, 12872-12873.

Tung, S.-I.; Lai, C.-C.; Liu, Y.-H.; Peng, S.-M.; Chiu, S.-H. (2013). Synthesis of a [2]catenane from the sodium ion templated orthogonal arrangement of two diethylene glycol chains. Angew. Chem. Int. Ed. 52, 13269-13272.

Ashton, P. R.; Goodnow, T. T.; Kaifer, A. E.; Reddington, M. V.; Slawin, A. M. Z.; Spencer, N.; Stoddart, J. F.; Vicent, C.; Williams, D. J. (1989). A [2]catenane made to order. Angew. Chem., Int. Ed. Engl. 28, 1396-1399.

Bravo, J. A.; Raymo, F. M.; Stoddart, J. F.; White, A. J. P.; Williams, D. J. (1998). High yielding template-directed syntheses of [2]rotaxanes. Eur. J. Org. Chem. 1998, 2565-2571.

G. Hamilton, D.; K. M. Sanders, J.; E. Davies, J.; Clegg, W.; J. Teat, S. (1997). Neutral [2]catenanes from oxidative coupling of [small pi]-stacked components. Chem. Commun., 897-898.

Hunter, C. A. (1992). Synthesis and structure elucidation of a new [2]-catenane. J. Am. Chem. Soc. 114, 5303-5311.

Vögtle, F.; Meier, S.; Hoss, R. (1992). One-Step synthesis of a fourfold functionalized catenane. Angew. Chem., Int. Ed. Engl. 31, 1619-1622.

Xue, M.; Su, Y.-S.; Chen, C.-F. (2010). Isomeric squaraine-based [2]pseudorotaxanes and [2]rotaxanes: synthesis, optical properties, and their tubular structures in the solid state. Chem. Eur. J. 16, 8537-8544.

Johnston, A. G.; Leigh, D. A.; Pritchard, R. J.; Deegan, M. D. (1995). Facile synthesis and solid-state structure of a benzylic amide [2]catenane. Angew. Chem., Int. Ed. Engl. 34, 1209-1212.

Fu, N.; Baumes, J. M.; Arunkumar, E.; Noll, B. C.; Smith, B. D. (2009). Squaraine rotaxanes with boat conformation macrocycles. J. Org. Chem. 74, 6462-6468.

Armspach, D.; Ashton, P. R.; Moore, C. P.; Spencer, N.; Stoddart, J. F.; Wear, T. J.; Williams, D. J. (1993). The self-assembly of catenated cyclodextrins. Angew. Chem., Int. Ed. Engl. 32, 854-858.

Fujita, M.; Ibukuro, F.; Hagihara, H.; Ogura, K. (1994). Quantitative self-assembly of a [2]catenane from two preformed molecular rings. Nature 367, 720-723.

Wasserman, E. (1962). Chemical topology. Sci. Amer. 207, 94-102.

Li, H.; Fahrenbach, A. C.; Dey, S. K.; Basu, S.; Trabolsi, A.; Zhu, Z.; Botros, Y. Y.; Stoddart, J. F. (2010). Mechanical bond formation by radical templation. Angew. Chem. Int. Ed. 49, 8260-8265.

Li, H.; Zhu, Z.; Fahrenbach, A. C.; Savoie, B. M.; Ke, C.; Barnes, J. C.; Lei, J.; Zhao, Y.-L.; Lilley, L. M.; Marks, T. J.; Ratner, M. A.; Stoddart, J. F. (2013). Mechanical bond-induced radical stabilization. J. Am. Chem. Soc. 135, 456-467.

Wang, Y.; Frasconi, M.; Liu, W.-G.; Sun, J.; Wu, Y.; Nassar, M. S.; Botros, Y. Y.; Goddard, W. A.; Wasielewski, M. R.; Stoddart, J. F. (2016). Oligorotaxane radicals under orders. ACS Cent. Sci. 2, 89-98.

Barnes, J. C.; Fahrenbach, A. C.; Cao, D.; Dyar, S. M.; Frasconi, M.; Giesener, M. A.; Benitez, D.; Tkatchouk, E.; Chernyashevskyy, O.; Shin, W. H.; Li, H.; Sampath, S.; Stern, C. L.; Sarjeant, A. A.; Hartlieb, K. J.; Liu, Z.; Carmieli, R.; Botros, Y. Y.; Choi, J. W.; Slawin, A. M. Z.; Ketterson, J. B.; Wasielewski, M. R.; Goddard, W. A.; Stoddart, J. F. (2013). A Radically configurable six-state compound. Science 339, 429-433.

Sun, J.; Wu, Y.; Wang, Y.; Liu, Z.; Cheng, C.; Hartlieb, K. J.; Wasielewski, M. R.; Stoddart, J. F. (2015). An electrochromic tristable molecular switch. J. Am. Chem. Soc. 137, 13484-13487. Wang, Y.; Sun, J.; Liu, Z.; Nassar, M. S.; Botros, Y. Y.; Stoddart, J. F. (2016). Symbiotic control in mechanical bond formation. Angew. Chem. Int. Ed. 55, 12387-12392.

Gibbs-Hall, I. C.; Vermeulen, N. A.; Dale, E. J.; Henkelis, J. J.; Blackburn, A. K.; Barnes, J. C.; Stoddart, J. F. (2015). Catenation through a combination of radical templation and ring-closing metathesis. J. Am. Chem. Soc. 137, 15640-15643.

Sun, J.; Liu, Z.; Liu, W.-G.; Wu, Y.; Wang, Y.; Barnes, J. C.; Hermann, K. R.; Goddard, W. A.; Wasielewski, M. R.; Stoddart, J. F. (2017). Mechanical bond-protected air-stable radicals. J. Am. Chem. Soc. 139, 12704-12709.

Trabolsi, A.; Khashab, N.; Fahrenbach, A. C.; Friedman, D. C.; Colvin, M. T.; Coti, K. K.; Benitez, D.; Tkatchouk, E.; Olsen, J.-C.; Belowich, M. E.; Carmielli, R.; Khatib, H. A.; Goddard, W. A.; Wasielewski, M. R.; Stoddart, J. F. (2010). Radically enhanced molecular recognition. Nat. Chem. 2, 42-49.

Wu, Q.; Rauscher, P. M.; Lang, X.; Wojtecki, R. J.; de Pablo, J. J.; Hore, M. J. A.; Rowan, S. J. (2017). Poly[n]catenanes: Synthesis of molecular interlocked chains. Science. DOI: 10.1126/science.aap7675.

Niu, Z.; Gibson, H. W. (2009). Polycatenanes. Chem. Rev. 109, 6024-6046.

Rostovtsev, V. V.; Green, L. G.; Fokin, V. V.; Sharpless, K. B. (2002). A stepwise huisgen cycloaddition process: copper(i)-catalyzed regioselective "ligation" of azides and terminal alkynes. Angew. Chem. Int. Ed. 41, 2596-2599.

Sue, C.-H.; Basu, S.; Fahrenbach, A. C.; Shveyd, A. K.; Dey, S. K.; Botros, Y. Y.; Stoddart, J. F. (2010). Enabling tetracationic cyclophane production by trading templates. Chemical Science 1, 119-125.

Park, K.-M.; Kim, S.-Y.; Heo, J.; Whang, D.; Sakamoto, S.; Yamaguchi, K.; Kim, K. (2002). Designed Self-Assembly of Molecular Necklaces. J. Am. Chem. Soc. 124, 2140-2147.

Schwarz, F.; Kastlunger, G.; Lissel, F.; Egler-Lucas, C.; Semenov, S. N.; Venkatesan, K.; Berke, H.; Stadler, R.; Lörtscher, E. (2015). Field-induced Conductance Switching by Charge-State Alternation in Organometallic Single-Molecule Junctions. Nat. Nanotechnol. 11, 170.

Wen, H.; Li, W.; Chen, J.; He, G.; Li, L.; Olson, M. A.; Sue, A. C.-H.; Stoddart, J. F.; Guo, X. (2016). Complex Formation Dynamics in a Single-Molecule Electronic Device. Science Advances 2.

Jia, C.; Migliore, A.; Xin, N.; Huang, S.; Wang, J.; Yang, Q.; Wang, S.; Chen, H.; Wang, D.; Feng, B.; Liu, Z.; Zhang, G.; Qu, D.-H.; Tian, H.; Ratner, M. A.; Xu, H. Q.; Nitzan, A.; Guo, X. (2016). Covalently Bonded Single-Molecule Junctions with Stable and Reversible Photoswitched Conductivity. Science 352, 1443-1445.

Florian, S.; Michael, K.; Georg, K.; Heinz, B.; Robert, S.; Koushik, V.; Emanuel, L. (2016). Charge Transport and Conductance Switching of Redox-Active Azulene Derivatives. Angew. Chem. Mt. Ed. 55, 11781-11786.

Burgess, M.; Chénard, E.; Hernandez-Burgos, K.; Nagatjuna, G.; Assary, R. S.; Hui, J.; Moore, J. S.; Rodríguez-López, J. (2016). Impact of backbone tether length and structure on the electrochemical performance of viologen redox active polymers. Chem. Mater. 28, 7362-7374.

Doris, S. E.; Ward, A. L.; Baskin, A.; Frischmann, P. D.; Gavvalapalli, N.; Chénard, E.; Sevov, C. S.; Prendergast, D.; Moore, J. S.; Helms, B. A. (2017). Macromolecular design strategies for preventing active-material crossover in non-aqueous all-organic redox-flow batteries. Angew. Chem. Int. Ed. 56, 1595-1599.

Hendriks, K. H.; Robinson, S. G.; Braten, M. N.; Sevov, C. S.; Helms, B. A.; Sigman, M. S.; Minteer, S. D.; Sanford, M. S. (2018). High-performance oligomeric catholytes for effective macromolecular separation in nonaqueous redox flow batteries. ACS Cent. Sci. 4, 189-196.

Winsberg, J.; Hagemann, T.; Janoschka, T.; Hager, M. D.; Schubert, U. S. (2017). Redox-flow batteries: from metals to organic redox-active materials. Angew. Chem. Int. Ed. 56, 686-711.

Wei, X.; Pan, W.; Duan, W.; Hollas, A.; Yang, Z.; Li, B.; Nie, Z.; Liu, J.; Reed, D.; Wang, W.; Sprenkle, V. (2017). Materials and Systems for Organic Redox Flow Batteries: Status and Challenges. ACS Energy Letters 2, 2187-2204.

Park, M.; Ryu, J.; Wang, W.; Cho, J. (2016). Material Design and Engineering of Next-Generation Flow-Battery Technologies. Nat. Rev. Mater. 2, 16080.

Zhang, L.; Ding, Y.; Zhang, C.; Zhou, Y.; Zhou, X.; Liu, Z.; Yu, G. (2018). Enabling Graphene-Oxide-Based Membranes for Large-Scale Energy Storage by Controlling Hydrophilic Microstructures. Chem 4, 1035-1046.

EXAMPLES

General Methods

All chemicals and reagents were purchased from commercial suppliers (Aldrich or Fisher) and used without further purification. 2-Azidoethyl 4-methylbenzenesulfonate was prepared according to literature procedures.[1] Thin layer chromatography (TLC) was carried out on silica gel 60 F254 (E. Merck). Analytical high performance chromatography (HPLC) was performed on reverse phase HPLC (RP-HPLC) instruments, using C18 columns and a binary solvent system (MeCN and $H_2O$ with 0.1% $CF_3CO_2H$). Column chromatography was carried out on silica gel 60F (Merck 9385, 0.040-0.063 mm). UV/Vis/NIR Absorption spectra were recorded using a UV-3600 Shimadzu spectrophotometer. Nuclear magnetic resonance (NMR) spectra were recorded at 298 K on a Bruker Advance 500 and 600 spectrometers, with working frequencies of 500 and 600 MHz for $^1H$, and 125 and 150 MHz for $^{13}C$, respectively. Chemical shifts are reported in ppm relative to the signals corresponding to the residual non-deuterated solvents ($CD_3CN$: δ 1.94 ppm; $CDCl_3$: δ, 7.26 ppm). High-resolution mass spectra were measured on an Agilent 6210 Time of Flight (TOF) LC-MS, using an ESI source, coupled with Agilent 1100 HPLC stack, using direct infusion (0.6 mL/min). Cyclic voltammetry (CV) experiments were carried out at room temperature in Ar-purged solutions of MeCN with a Gamry multipurpose instrument (Reference 600) interfaced to a PC. All CV experiments were performed using a platinum working electrode (0.0314 $cm^2$). The electrode surface was polished routinely with 0.05 μm alumina-methanol slurry on a felt surface immediately before use. The counter electrode was a Pt coil and the reference electrode was an Ag/AgCl electrode. The concentration of the sample and supporting electrolyte, tetrabutylammonium hexafluorophosphate ($TBAPF_6$), were 1.0 mM and 0.1 M, respectively. The CV cell was dried in an oven immediately before use, and Ar was flushed continually through the cell as it was cooled down to room temperature to avoid condensation of water.

Synthetic Protocols a) AV.2PF$_6$.

Figure 13:
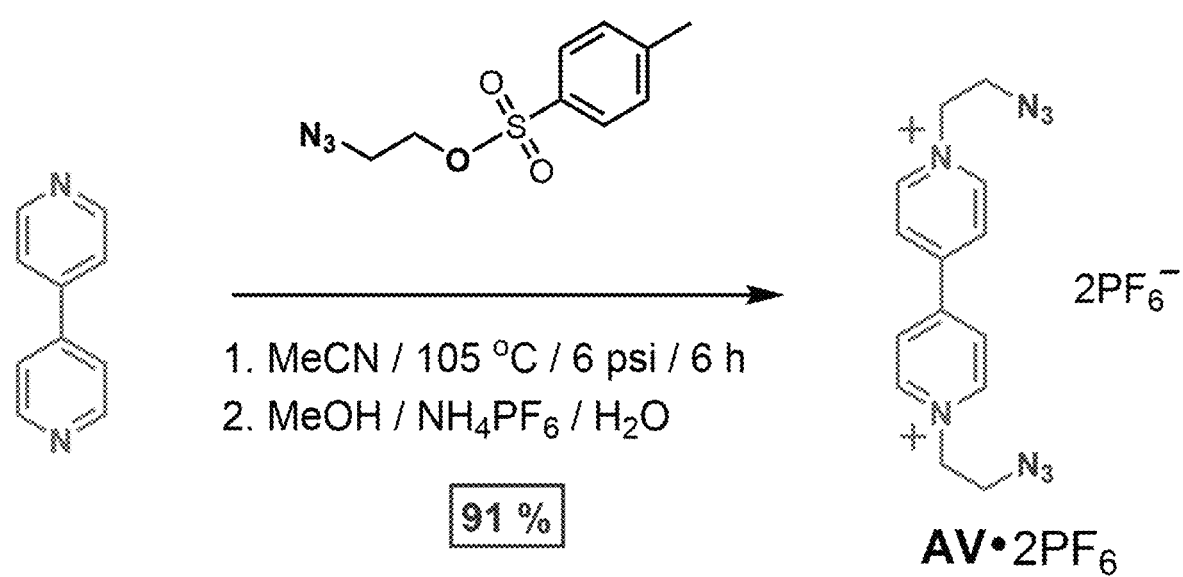
FIG. 13. Illustration of Scheme 5. Preparation of AV.

As depicted in Scheme 5 (FIG. 13), a mixture of 4,4'-bipyridine (450 mg, 2.9 mmol) and 2-azidoethyl 4-methylbenzenesulfonate[1] (2.0 g, 8.7 mmol) in dry MeCN (20 mL) was heated at 105° C./6 psi under $N_2$ for 3 h. The reaction mixture was cooled to room temperature followed by the addition of an excess tetraethylammonium bromide. The resulting precipitate was filtered and washed thoroughly with MeCN. The solid was dissolved in $H_2O$ (100 mL), followed by the addition of excess of $NH_4PF_6$, resulting in the precipitation of an off-white solid which was collected by centrifugation, washed with $H_2O$ several times and dried in vacuo to yield AV.2PF$_6$ as a white solid (1.57 g) in 91% yield. $^1H$ NMR (500 MHz, $CD_3CN$, 298 K) δ=8.92 (d, J=6.4 Hz, 4H), 8.42 (d, J=6.4 Hz, 4H), 4.74 (t, J=5.3 Hz, 4H), 4.01 (4.74 (t, J=5.3 Hz, 4H). $^{13}C$ NMR (125 MHz, $CD_3CN$, 298 K) δ=151.4, 147.1, 128.1, 61.6, 51.2. ESI-HRMS calcd for [M-PF$_6$]$^+$ m/z=441.1134, found 441.1141.

b) HV.2PF$_6$.

Scheme 6. Preparation of HV

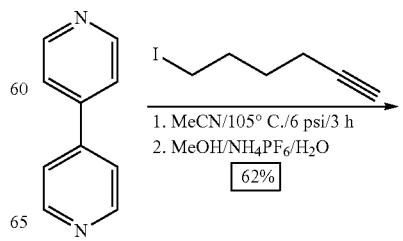

1. MeCN/105° C./6 psi/3 h
2. MeOH/NH$_4$PF$_6$/H$_2$O

62%

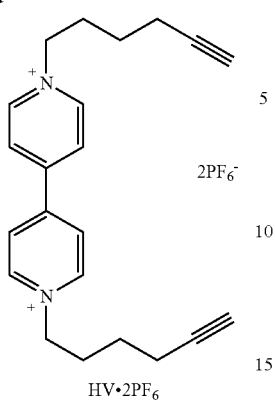

HV·2PF₆

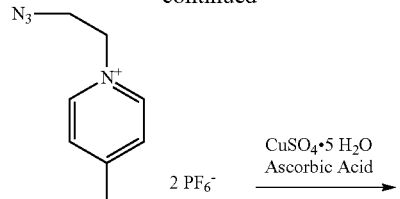

AV·2 PF₆

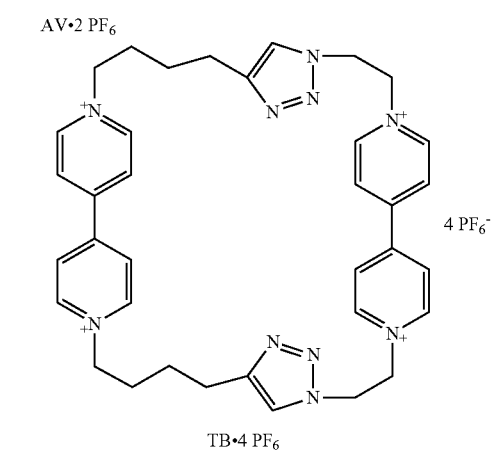

TB·4 PF₆

As depicted in Scheme 6, a mixture of 4,4'-bipyridine (1.0 g, 6.4 mmol) and 6-iodo-1-hexyne (4.6 g, 22 mmol) in dry MeCN (30 mL) was heated at 105° C./6 psi under $N_2$ for 3 h. The reaction mixture was cooled to room temperature and the resulting reddish precipitate was filtered and washed thoroughly with MeCN. The solid was dissolved in $H_2O$ (100 mL), followed by the addition of excess of $NH_4PF_6$, resulting in the precipitation of an off-white solid which was collected by centrifugation, washed with $H_2O$ (3×20 mL), MeOH (1×20 mL) and dried in vacuo to yield HV.2PF₆ as a light brown solid (2.4 g) in 62% yield. ¹H NMR (500 MHz, CD₃CN, 298 K) δ=8.90 (d, J=6.4 Hz, 4H), 8.39 (d, J=6.4 Hz, 4H), 4.65 (t, 1=7.5 Hz, 4H), 2.28 (dt, J=2.6 Hz, J=7.0 Hz, 4H), 2.23 (t, J=2.6 Hz, 2H), 2.13 (p, J=7.6 Hz, 4H), 1.60 (p, J=7.4 Hz, 4H). ¹³C NMR (125 MHz, CD₃CN, 298 K) δ=150.9, 146.5, 128.2, 84.2, 70.5, 62.5, 31.0, 25.5, 18.2. ESI-HRMS calcd for [M-PF₆]⁺ m/z=463.1732, found 463.1740.

c) TB.4PF₆.

Scheme 7. Preparation of AV

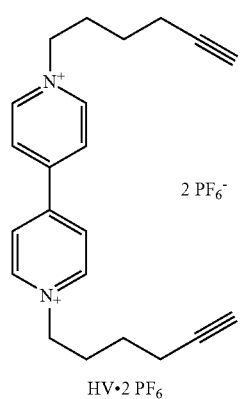

HV·2 PF₆

As depicted in Scheme 7, a solution of CUSO₄.5H₂O (10 mg, 0.04 mmol) in DMF (15 mL) was added to a solution of HV.2PF₆ (98 mg, 0.16 mmol) and AV.2PF₆ (95 mg, 0.16 mmol) in DMF (50 mL). After stirring for 30 min under a $N_2$ atmosphere, an excess of ascorbic acid (80 mg) was added. The reaction mixture was then stirred for 1 day at room temperature. Solvent was removed by rotary evaporation and the residue was redissolved in MeCN, followed by vacuum filtration. The filtrate was concentrated to ca. 5 mL and an excess of NH₄PF₆ (aq) solution was added. The resulting white precipitate was filtered and purified by RP-HPLC (H₂O-MeCN, 0.1% TFA, 0-100% MeCN in 60 min). A counter anion exchange from TFA salt to PF₆⁻ salt using NH₄PF₆ resulted in a white precipitate which was collected by centrifugation and washed several times with H₂O to afford TB.4PF₆ as a white solid (62 mg, 32%). ¹H NMR (500 MHz, CD₃CN, 298 K) δ=8.86 (d, J=6.8 Hz, 4H), 8.71 (d, J=6.8 Hz, 4H), 8.35 (d, J=6.8 Hz, 4H), 8.29 (d, =6.8 Hz, 4H), 7.83 (s, 2H), 5.18 (m, 4H), 5.01 (m, 4H), 4.70 (t, J=6.5 Hz, 4H), 2.76 (t, J=6.5 Hz, 4H), 2.06 (p, J=6.9 Hz, 4H), 1.63 (p, J=7.7 Hz, 4H). ¹³C NMR (125 MHz, CD₃CN, 298 K) δ=151.2, 151.0, 147.0, 146.9, 146.3, 128.1, 128.1, 125.6, 62.7, 61.1, 51.5, 30.6, 25.0, 24.3. Low-resolution ESI-MS calcd m/z=1049.2 [M-PF₆]⁺, found 1049.1; m/z=452.1 [M-2PF₆]²⁺, found 452.2; m/z=253.1 [M-3PF₆]³⁺, found 253.1. High-resolution ESI-MS calcd for [M-PF₆]⁺ m/z=1049.2514 and [M-2PF₆]²⁺ m/z=452.1433, found 1049.2517 and 452.1433, respectively.

d) [3]C.12PF₆.

As depicted in Scheme 1 (FIG. 9), an excess of Cu powder was added to a solution of AV.2PF₆ (29 mg, 0.05 mmol) and CBPQT.4 PF₆ (55 mg, 0.05 mmol) dissolved in dry MeCN (20 mL) in an $N_2$-filled glovebox. In a separate flask, HV.2PF$_6$ (30 mg, 0.05 mmol) and CBPQT.4PF$_6$ (55 mg, 0.05 mmol) were dissolved in dry MeCN (20 mL) and subjected to an excess amount of Cu powder. The two solutions were stirred at room temperature for 1 h before being mixed together quickly in another reaction flask. The reaction mixture was stirred at room temperature in the inert environment of a N$_2$-filled glovebox for 4 days. The resulting dark purple mixture was filtered inside the glovebox and NOPF$_6$ was added in small aliquots to the filtrate until the dark purple solution turned clear. The resulting solution was taken out of the glovebox and solvent was removed by rotary evaporation. The residue was purified using reversed-phase flash chromatography (C$_{18}$: water/MeCN 0.1% TFA 0-100%), followed by anion exchange from TFA$^-$ to PF$_6^-$ by treating the aqueous fractions with an excess amount of NF$_4$PF$_6$, resulting in a white precipitate which was collected by centrifugation and washed with H$_2$O several times before being dried in vacuo to yield an off-white solid (69 mg, 41%). $^1$H NMR (500 MHz, CD$_3$CN, 298 K) δ=9.61 (d, J=6.7 Hz, 4H), 9.43 (d, J=6.7 Hz, 4H), 9.38 (d, J=6.7 Hz, 4H), 9.36 (d, J=6.7 Hz, 4H), 8.95-8.45 (s, br, 16H), 8.15-7.95 (s, br, 16H), 6.60 (s, br, 16H), 5.93 (s, 2H), 5.48 (s, br, 16H), 5.46 (m, 4H), 4.99 (m, 4H), 4.74 (t, J=6.1 Hz, 4H), 1.30 (p, J=6.8 Hz, 4H), −0.36 (t, J=6.2 Hz, 4H), −0.46 (p, J=7.6 Hz, 4H). $^{13}$C NMR (125 MHz, CD$_3$CN, 298 K) δ=149.5, 149.0 (br), 148.6, 147.5, 147.4, 146.1 (br), 142.9, 135.9 (br), 130.9 (br), 128.9 (br, 2C), 127.5 (br), 123.4, 65.0 (br), 64.1, 62.1, 48.6, 30.3, 23.4, 23.3. Low-resolution ESI-MS calcd m/z=986.8 [M−3PF$_6$]$^{3+}$, found 986.6, m/z=703.9 [M−4PF$_6$]$^{4+}$, found 703.8, nil z=534.1 [M−5PF$_6$]$^{5+}$, found 534.1, m/z=420.9 [M−6PF$_6$]$^{6+}$, found 420.9. High-resolution ESI-MS calcd for [M-2PF$_6$]$^{2+}$ m/z=1552.7641 and [M-3PF$_6$]$^{3+}$ m/z=986.8540, found 1552.7628 and 986.8540, respectively.

e) Me$_2$TB.6PF$_6$.

Scheme 8. Preparation of ME$_2$TB

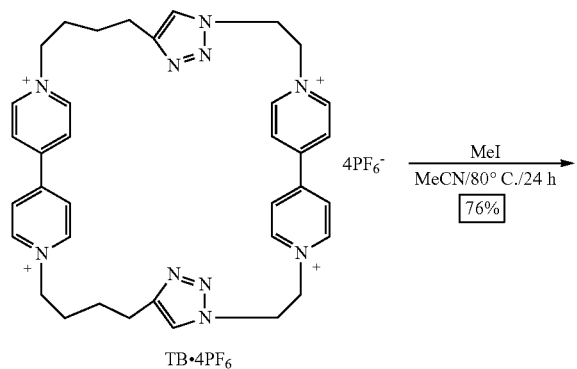

TB•4PF$_6$ → (MeI, MeCN/80° C./24 h, 76%) → Me$_2$TB•6PF$_6$

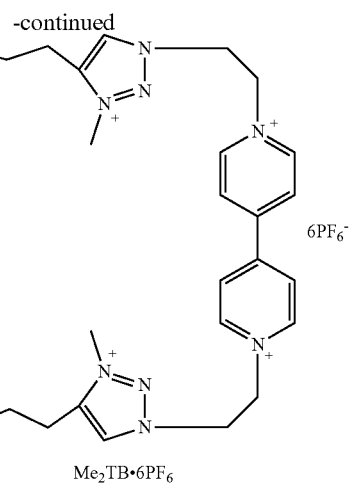

As depicted in Scheme 8, an excess of methyl iodide (0.1 mL) was added to a solution of TB.4PF$_6$ (8.0 mg, 6.7 μmop in MeCN (1.0 mL) and the reaction mixture was heated to 80° C. and stirred for 1 day. After cooling to room temperature, the solution was concentrated to ca. 0.2 mL and an excess of NH$_4$PF$_6$ (aq) solution was added. The resulting white precipitate was collected by centrifugation, washed several times with H$_2$O, and dried in vacuo. Recrystallization of the crude mixture (~90% pure by NMR) by slow diffusion of $^i$Pr$_2$O vapor into its solution in MeCN yielded Me$_2$TB.6PF$_6$ as an off-white solid (7.8 mg, 76%). $^1$H NMR (500 MHz, CD$_3$CN, 298 K) δ=8.86-8.81 (two overlapping doublets, J=8.7 Hz each, 4H each), 8.32 (two overlapping doublets, J=8.7 Hz each, 4H each), 8.10 (s, 2H), 7.83 (s, 2H), 5.30 (m, 4H), 5.15 (m, 4H), 4.69 (t, J=6.5 Hz, 4H), 4.02 (s, 6H), 2.82 (t, J=6.5 Hz, 4H), 2.10 (p, J=6.9 Hz, 4H), 1.59 (p, J=7.7 Hz, 4H). $^{13}$C NMR (125 MHz, CD$_3$CN, 298 K) δ=151.7, 150.9, 147.2, 146.5, 145.5, 130.1, 128.5, 128.2, 62.6, 59.3, 53.7, 38.7, 30.3, 23.5, 23.2. ESI-MS calcd m/z=612.13 [M-2PF$_6$]$^{2+}$, found 612.10; m/z=359.77 [M-3PF$_6$]$^{3-}$, found 359.71.

f) BBP.2PF$_6$.

Scheme 9. Preparation of BBP

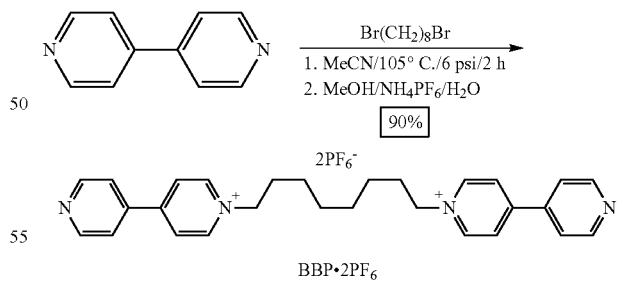

As depicted in Scheme 9, 4,4'-Bipyridine (5.0 g, 32 mmol) was dissolved in MeCN (50 mL) and heated under reflux. A solution of 1,8-dibromooctane (1.75 g, 6.4 mmol) in MeCN (20 mL) was added to the above solution during 30 min using a syringe pump. The reaction mixture was then heated at 105° C./6 psi under N$_2$ for 2 h before cooled to room temperature. The resulting precipitate was collected by vacuum filtration and washed thoroughly with MeCN. The solid was dissolved in H$_2$O (50 mL), followed by the addition of excess of NH$_4$PF$_6$, resulting in the precipitation of a white solid, which was collected by centrifugation, washed with H$_2$O several times and dried in vacuo to yield BBP.2PF$_6$ as a white solid (4.6 g) in 90% yield. $^1$H NMR (500 MHz, CD$_3$CN, 298 K) δ=8.84 (d, J=6.4 Hz, 4H), 8.76 (d, J=6.4 Hz, 4H), 8.31 (d, J=6.4 Hz, 4H), 7.79 (d, J=6.4 Hz, 4H), 4.54 (t, J=7.5 Hz, 4H), 1.99 (m, 4H), 1.37 (m, 8H). $^{13}$C NMR (125 MHz, CD$_3$CN, 298 K) δ=154.9, 152.0, 145.8, 142.2, 126.9, 122.7, 62.4, 31.7, 29.2, 26.3. ESI-HRMS calcd for [M-PF$_6$]$^+$ m/z=569.2263, found 569.2270.

g) BAV.4PF$_6$.

Figure 14:
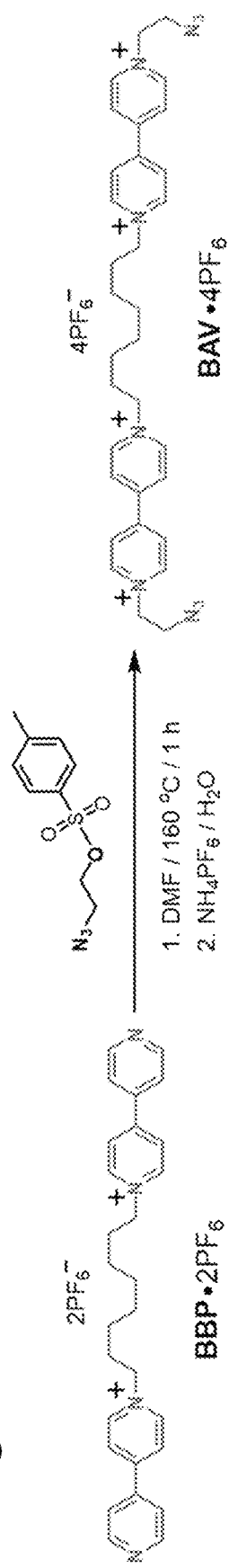
FIG. 14. Illustration of Scheme 10. Preparation of BAV.

As depicted in Scheme 10 (FIG. 14), a mixture of BBP.2PF$_6$ (130 mg, 0.18 mmol) and 2-azidoethyl 4-methylbenzenesulfonate[1] (200 mg, 0.83 mmol) in dry DMF (1.0 mL) was heated at 160° C. under N$_2$ for 1 h. The reaction mixture was cooled to room temperature, followed by the addition of an excess of a saturated solution of tetraethylammonium bromide in MeCN. The resulting precipitate was filtered off and washed thoroughly with MeCN. The solid was dissolved in H$_2$O (15 mL), followed by the addition of excess of NH$_4$PF$_6$, resulting in the precipitation of an off-white solid which was collected by centrifugation, washed with H$_2$O several times and dried in vacuo to yield BAV.4PF$_6$ as an off-white solid (129 mg) in 62% yield. $^1$H NMR (500 MHz, CD$_3$CN, 298 K) δ=8.90 (m, 8H), 8.40 (m, 8H), 4.74 (t, J=5.4 Hz, 4H), 4.61 (t, J=7.5 Hz, 4H), 4.01 (t, J=5.4 Hz, 4H), 2.02 (m, 4H), 1.40 (m, 8H). $^{13}$C NMR (125 MHz, CD$_3$CN, 298 K) δ=151.5, 150.8, 147.1, 146.5, 128.2, 128.1, 63.1, 61.6, 51.2, 31.9, 29.3, 26.5, 23.1. ESI-HRMS calcd for [M-PF$_6$]$^4$ m/z=999.2356, found 999.2384.

h) BHV.4PF$_6$.

Figure 15:
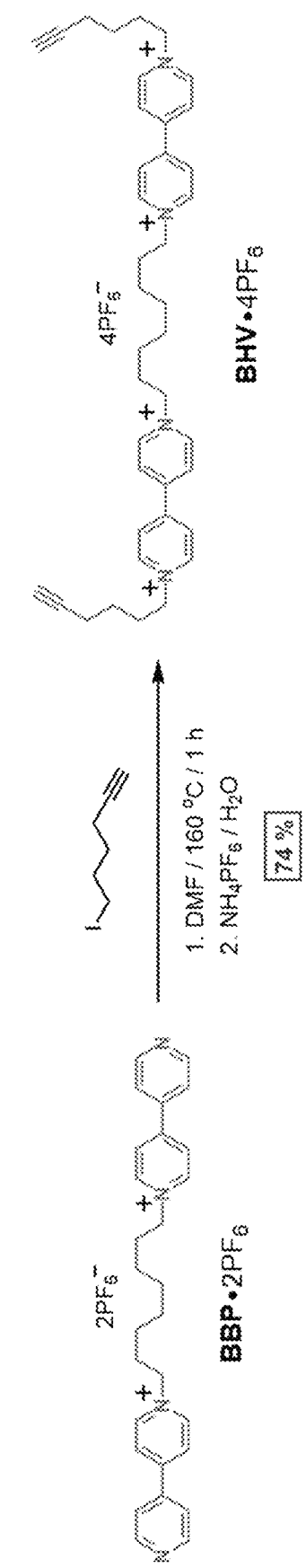
FIG. 15. Illustration of Scheme 11. Preparation of BHV.

As depicted in Scheme 11 (FIG. 15), a mixture of BBP.2PF$_6$ (150 mg, 0.21 mmol) and 6-iodo-1-hexyne (200 mg, 0.96 mmol) in dry DMF (1.0 mL) was heated at 160° C. under N$_2$ for 1 h. The reaction mixture was cooled to room temperature and suspended in MeCN (10 mL), followed by the addition of an excess of a saturated solution of tetraethylammonium bromide in MeCN. The resulting precipitate was filtered and washed thoroughly with MeCN. The solid was dissolved in H$_2$O (15 mL), followed by the addition of excess of NH$_4$PF$_6$, resulting in the precipitation of an off-white solid which was collected by centrifugation, washed with H$_2$O several times and dried in vacuo to yield BHV.4PF$_6$ as an off-white solid (180 mg) in 74% yield. $^1$H NMR (500 MHz, CD$_3$CN, 298 K) δ=8.90 (m, 8H), 8.38 (m, 8H), 4.65 (t, J=7.6 Hz, 4H), 4.61 (t, J=7.6 Hz, 4H), 2.29 (dt, J=2.6 Hz, J=7.0 Hz, 4H), 2.23 (t, J=2.6 Hz, 2H), 2.13 (p, J=7.6 Hz, 4H), 2.02 (m, 4H), 1.60 (p, J=7.4 Hz, 4H), 1.40 (m, 8H). $^{13}$C NMR (125 MHz, CD$_3$CN, 298 K) δ=151.0, 150.9, 146.5, 128.3, 128.2, 84.3, 70.6, 63.1, 62.6, 31.9 31.1, 29.3, 26.5, 25.6, 18.3. ESI-HRMS calcd for [M-PF$_6$]$^+$ m/z=1021.2955, found 1021.3019.

i) r[5]C.24PF$_6$.

As depicted in Scheme 4 (FIG. 12), an excess of Cu powder was added to a solution of BAV.4PF$_6$ (7 mg, 6.1 nmol) and CBPQT.4 PF$_6$ (27 mg, 24.5 nmol) dissolved in dry MeCN (6 mL) in an N$_2$-filled glovebox. In a separate flask, BHV.4PF$_6$ (7.1 mg, 6.1 nmol) and CBPQT.4PF$_6$ (27 mg, 24.5 nmol) were dissolved in dry MeCN (6 mL) and subjected to an excess of Cu powder. The two solutions were stirred at room temperature for 2 h before being mixed together quickly in another reaction flask. The reaction mixture was stirred at room temperature in the inert environment of a N$_2$-filled glovebox for 4 days. The resulting dark purple mixture was filtered inside the glovebox and NOPF$_6$ was added in small aliquots to the filtrate until the dark purple solution turned clear. The resulting solution was taken out of the glovebox and solvent was removed by rotary evaporation. The residue was purified using reverse-phase flash chromatography (C$_{18}$: water/MeCN 0.1% TFA 0-100%), followed by anion exchange from TFA$^-$ to PF$_6^-$ by treating the aqueous fractions with an excess of NH$_4$PF$_6$, resulting in a white precipitate which was collected by centrifugation and washed with H$_2$O several times before being dried in vacuo to yield an off-white solid (14.8 mg, 36%). $^1$H NMR (500 MHz, CD$_3$CN, 298 K) δ=9.28 (d, J=6.8 Hz, 4H), 9.13-9.05 (br, 22H), 8.96 (d, br, 8H), 8.88 (br, 2H), 8.82 (br, 4H), 8.77 (d, J=6.3 Hz, 2H), 8.46 (d, J=6.7 Hz, 8H), 7.98 (d, J=6.7 Hz, 8H), 7.66 (s, 16H), 7.48 (s, 8H), 7.47 (s, 8H), 5.81 (s, 8H), 5.79 (s, 8H), 5.78 (s, 16H), 5.37 (s, 2H), 5.21 (t, J=6.5 Hz, 4H), 4.68 (t, J=6.5 Hz, 4H), 4.60-4.51 (m, br, 6H), 1.43 (p, J=7.7 Hz, 4H), 0.85 (p, J=7.7 Hz, 4H), 0.79 (p, J=7.7 Hz, 4H), −0.15 (p, J=7.7 Hz, 4H), (−0.49)-(−0.63) (m, br, 8H), −2.37 (m, br, 4H), −2.41 (m, br, 4H). $^{13}$C NMR (125 MHz, CD$_3$CN, 298 K) δ=152.2, 151.5, 151.1, 151.1, 149.2 (×2), 148.7, 147.5, 146.8, 146.5, 146.4, 146.3, 143.7, 137.1, 137.0 (×2), 131.4, 131.2, 128.8, 128.5, 127.9, 127.2, 122.2, 68.7, 65.9, 65.7, 62.1 (×2), 62.0, 60.0, 49.6, 32.0, 31.6, 31.4, 28.8 (×2), 26.6, 26.5, 24.1, 23.6. High-resolution ESI-MS calcd m/z=2092.6833 [M-3PF$_6$]$^{3+}$, found 2092.6853, m/z=1533.2713 [M-4PF$_6$]$^{4+}$, found 1533.2693, m/z=1197.6241 [M-5PF$_6$]$^{5+}$, found 1197.6225.

Analytical HPLC Analysis

Figure 8A:
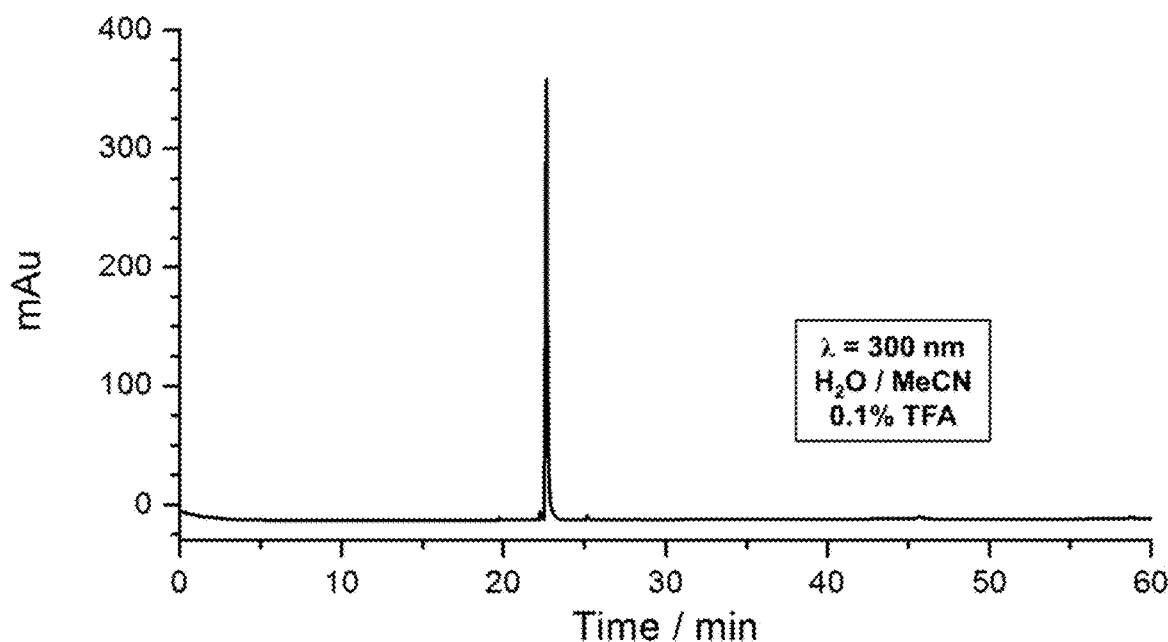
FIGS. 8A-8B. Analytical RP-HPLC trace of $TB.4PF_6$ (FIG. 8A) and $[3]C.12PF_6$ (FIG. 8B). The photodiode array was set to detect absorbance at 300 nm.
Figure 8B:
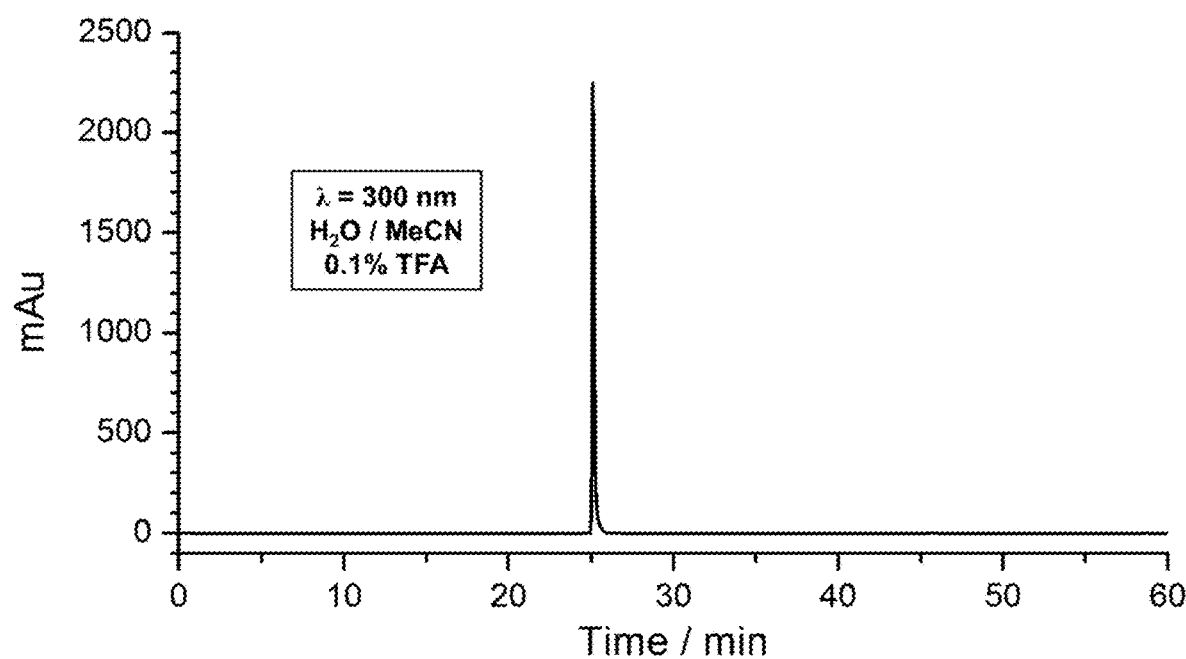

HPLC was performed as described in the methods. The HPLC traces of the compounds TB.4PF$_6$ and [3]C.12PF$_6$ are shown in FIG. 8A and FIG. 8B, respectively.

Crystallographic Characterization

In a typical data collection, a suitable crystal was selected and mounted in inert oil and transferred to the cold gas stream of a Bruker Kappa APEX CCD area detector diffractometer. The crystal was kept at 100.0 K during data collection. Using Olex2,[2] the structure was solved with the XT[3] structure solution program employing Dual Space and refined with the XL[4] refinement package using least squares minimization. The coordinates of the non-hydrogen atoms were refined anisotropically, while hydrogen atoms were included in the calculation isotropically but not refined. The crystallographic information, structural parameters, and additional refinement details for TB.4PF$_6$, [AV⊂CBPQT].3PF$_6$, [3]C.12PF$_6$, [3]C.6PF$_6$, and r[5]C.24PF$_6$ are given below.

a) TB.4PF$_6$

Method. Single crystals of TB.4PF$_6$ were grown by slow diffusion of iPr$_2$O vapor into a solution of TB.4PF$_6$ in MeCN over the course of three days.

Crystal Parameters. C$_{36}$H$_{42}$F$_{24}$N$_{10}$P$_4$. Clear block (0.255×0.117×0.090 mm). Monoclinic, C 2/m, a=12.5832(9), b=26.390(2), c=17.5713(13) Å, α=90, β=96.326(4), γ=90°, V=5799.4(7) Å$^3$, Z=4, T=100(2) K, ρ$_{calc}$=1.534 g cm$^{-3}$, μ=0.292 mm$^{-1}$. Of a total of 38804 reflections which were collected, 5302 were unique (R$_{int}$=0.0618). Final R$_1$ (F$^2$>2σF$^2$)=0.0657 and wR$_2$=0.2047 (all data). CCDC deposition number 1828432.

Refinement Details. The two bipyridinium units within one TB$^{4+}$ macrocycle were found to be crystallography equivalent while there is disorder found for the two 1-(1-(ethylene)-1H-1,2,3-triazole-4-yl)butylene linkers, which have been modeled over two sites with a 50% occupancy for each site. The solvent-masking procedure, as implemented in Olex2, was used to remove the electronic contributions of heavily disordered solvent molecules from the refinement. As the exact solvent content is not known, only the atoms used in the refinement model are reported here in the formula. Total solvent accessible volume/cell=206.1 Å$^3$

[3.6%]. Three of the four $PF_6^-$ anions were modeled over two positions and their anisotropic displacement parameters were refined using SIMU and DELU restraints.[5]

b) [AV⊂CBPQT].3PF$_6$

Method. Single crystals of the trisradical tricationic complex [AV⊂CBPQT].3PF$_6$—a [2]pseudorotaxane—were grown in a glovebox under positive $N_2$ by treating a solution of 1:1 HV.2PF$_6$/CBPQT.4PF$_6$ in MeCN with Cu powder for 1 h, followed by filtration of the resulted purple solution through a 0.2-μm filter into a culture tube. Thereafter, slow diffusion of iPr$_2$O vapor into the MeCN solution was allowed to happen over the course of 2 days under nitrogen atmosphere. A rod-like crystal was picked out, quickly mounted using paratone oil (Infineum V8512) on a microloop and flash frozen under a continuous cold stream of nitrogen gas.

Crystal Parameters. $C_{54}H_{54}F_{18}N_{14}P_3$. Dark block (0.203×0.114×0.084 mm). Triclinic, P$\bar{1}$, a=9.7754(13), b=11.0040(14), c=14.024(2) Å, α=73.827(3), β=76.518(3), γ=80.565(3)°, V=1401.0(3) Å$^3$, Z=1, T=100(2) K, pcalc=1.581 g cm$^{-3}$, μ=0.220 mm$^{-1}$. Of a total of 17383 reflections which were collected, 4757 were unique ($R_{int}$=0.0286). Final $R_1$ ($F^2>2\sigma F^2$)=0.0343 and $wR_2$=0.0839 (all data). No disorder was observed in the sample; no restraints were used in the refinement.

c) [3]C.12PF$_6$

Method. Single crystals of [3]C.12PF$_6$ were grown by slow diffusion of iPr$_2$O vapor into a solution of [3]C.12PF$_6$ in MeCN under ambient conditions at room temperature over the course of four days.

Crystal Parameters. $C_{112}H_{112}F_{72}N_{20}P_{12}$. Colorless block (0.117×0.083×0.074 mm). Triclinic, P$\bar{1}$, a=13.0318(3), b=17.5225(5), c=20.1997(6) Å, α=64.483(2), β=89.085(2), γ72.334(2), V=3930.9(2) Å$^3$, Z=1, T=100(2) K, pcalc=1.469 g cm$^{-3}$, μ=0.264 mm$^{-1}$. Of a total of 44829 reflections which were collected, 13817 were unique ($R_{int}$=0.0471). Final $R_1$ ($F^2>2\sigma F^2$)=0.1232 and $wR_2$ 0.3963 (all data). CCDC deposition number 1828429.

Figure 2B:
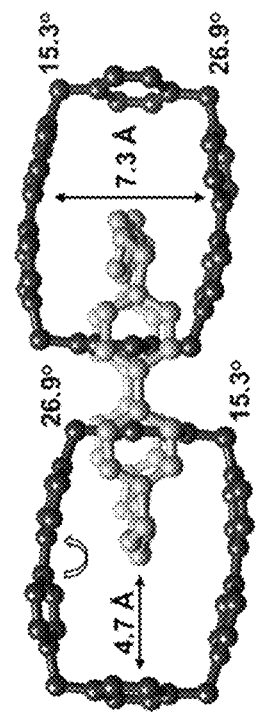
Figure 2E:
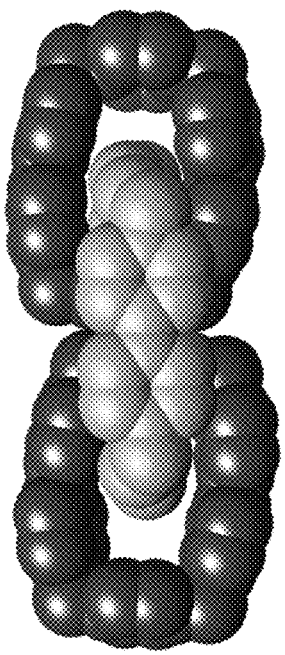
Figure 2A:
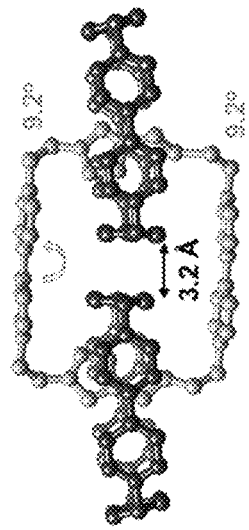
Figure 2D:
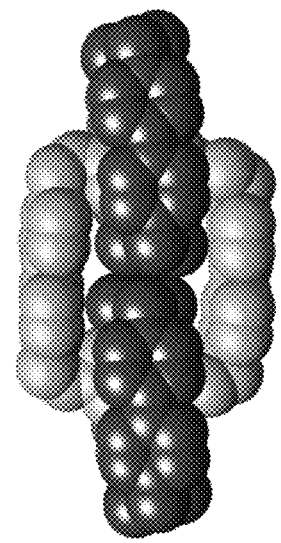
Figure 2G:
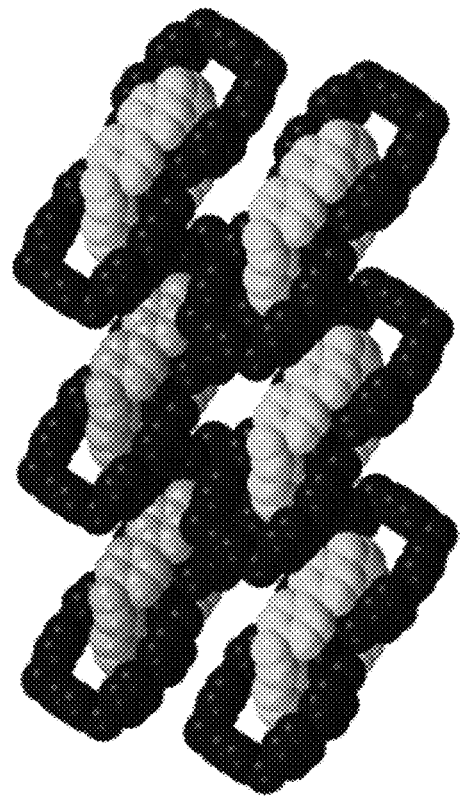
FIGS. 2G-2J. Space-filling representations of the structure of $[3]C.12PF_6$ from several views with hydrogen atoms, $PF_6^-$ counter ions, and solvent molecules omitted for the sake of clarity.
Figure 2H:
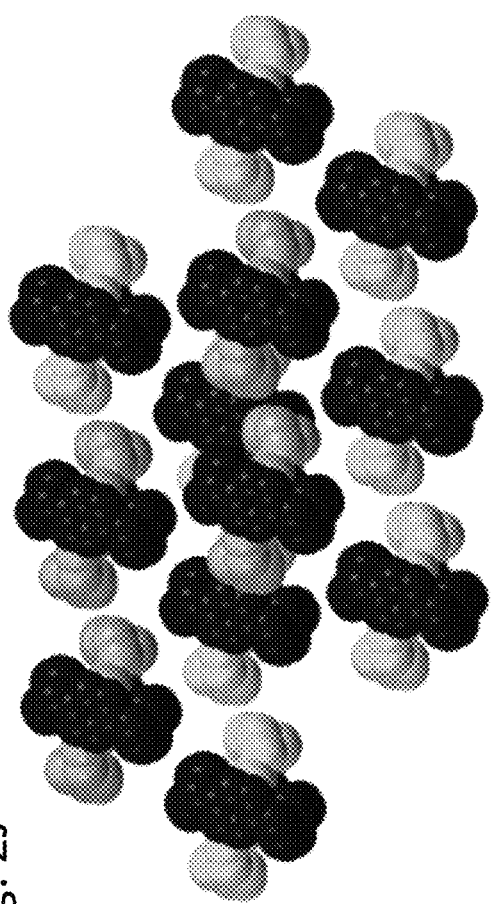
Figure 2I:
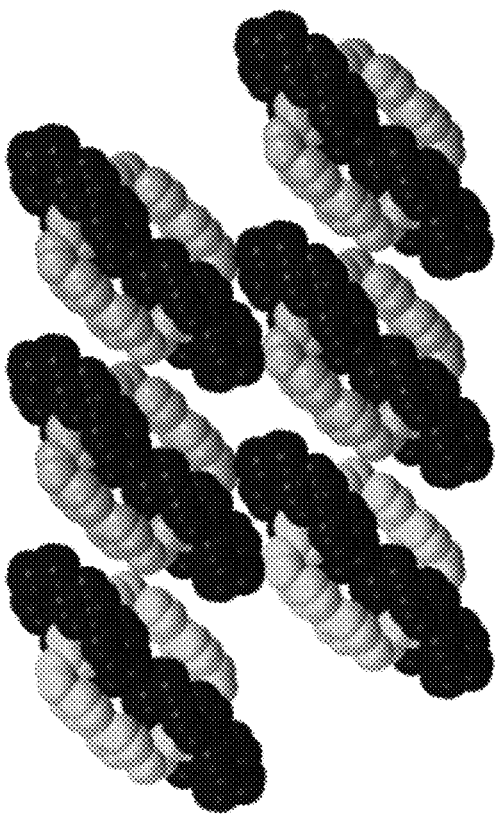
Figure 2J:
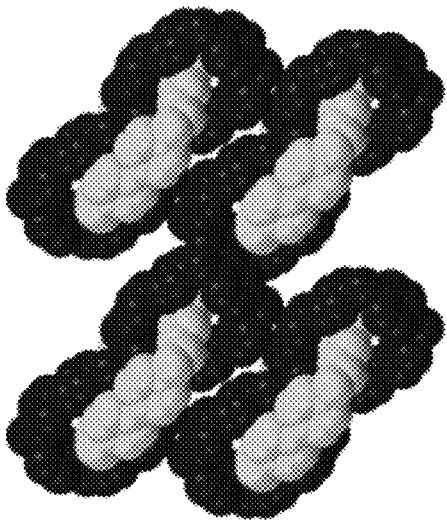

Refinement Details. The two CBPQT$^{4+}$ macrocycles as well as the two bipyridinium units of the central macrocycle (TB$^{4+}$) in [3]C$^{12+}$ were found to be crystallography equivalent with an inversion center at the centroid of the TB$^{4+}$ ring. As such, the 1-(1-(ethylene)-1H-1,2,3-triazole-4-yl)butylene linkers of the TB$^{4+}$ macrocycle were found to be disordered and were modeled over two positions with half-occupancy. The solvent-masking procedure, as implemented in Olex2, was used to remove the electronic contributions of heavily disordered solvent molecules from the refinement. As the exact solvent content is not known, only the atoms used in the refinement model are reported here in the formula. Total solvent accessible volume/cell=109.2 Å$^3$ [2.8%]. Three of the six PF$_6^-$ anions in the asymmetric unit were modeled over two positions and their anisotropic displacement parameters were refined using SIMU and DELU restraints.[5] Stick representations of the solid-state structure of [3]C.12PF$_6$ are shown in FIG. 2A-2C and space-filling representations of the superstructure are shown in FIG. 2D-2J. As the result of being interlocked in a [3]catenane, the two crystallography equivalent CBPQT$^{4+}$ macrocycles exhibit much smaller torsional angles (mean angle=17.1°) of the bipyridinium units compared to either those found in the non-interlocked CBPQT$^{4+}$ structure (torsional angle=39.8°)[6] or the BIPY$^{.+}$ units within the non-interlocked TB$^{4+}$ (torsional angle=72.8°).

d) [3]C.6PF$_6$

Method. The hexaradical hexacationic [3]C$^{6(.+)}$ [3]catenane was obtained by treating a solution of its oxidized form [3]C.12PF$_6$ in MeCN with Zn dust for 20 minutes in a glovebox under positive $N_2$. The purple solution was filtered through a 0.2-μm filter into a culture tube to remove the excess of zinc dust and single crystals of [3]C.6PF$_6$ were grown by slow diffusion of iPr$_2$O vapor into the MeCN solution over the course of 1 week under a nitrogen atmosphere at room temperature. A plate-shape crystal was picked out, quickly mounted using paratone oil (Infineum V8512) on a microloop and flash frozen under a continuous cold stream of nitrogen gas.

Crystal Parameters. $C_{108}H_{80}F_{36}N_{18}P_6$. Dark purple plate (0.116×0.098×0.057 mm). Triclinic, P$\bar{1}$, a=13.7572(11), b=19.6568(17), c=24.923(2) Å, α=112.045(7), β=103.053(7), γ=91.634(7), V=6037.5(9) Å$^3$, Z=2, T=100(2) K, pcalc=1.375 g cm$^{-3}$, μ=1.792 mm$^{-1}$. Of a total of 31109 reflections which were collected, 9216 were unique ($R_{int}$=0.0528). Final $R_1$ ($F^2>2\sigma F^2$)=0.1326 and $wR_2$=0.4126 (all data). CCDC deposition number 1828430.

Refinement Details. The two 1-(1-(ethylene)-1H-1,2,3-triazole-4-yl)butylene linkers of the TB$^{2(.+)}$ macrocycle within the structure of [3]C$^{6(.+)}$ were found to be disordered and were modeled over two positions with half-occupancy. The solvent-masking procedure, as implemented in Olex2, was used to remove the electronic contributions of heavily disordered solvent molecules from the refinement. As the exact solvent content is not known, only the atoms used in the refinement model are reported here in the formula. Total solvent accessible volume/cell=61.88 Å$^3$ [1.0%]. Three of the six PF$_6^-$ anions were modeled over two positions and their anisotropic displacement parameters were refined using SIMU and DELU restraints.[5]

On account of the poor diffraction power of the crystal (resolution of 1.11 Å) and the disorders of both the 1-(1-(ethylene)-1H-1,2,3-triazole-4-yl)butylene linkers and three of the PF$_6^-$ anions, the CheckCif gives 3 Å and 8 B alerts. All A alerts result from the poor scattering of the crystal while the B alerts are due to the disorders of the structure components. Stick representations of the X-ray crystal structure of [3]C.6PF$_6$ are shown in FIG. 4B-4D and space-filling representations of the superstructure are shown in FIG. 4F-4J.

e) r[5]C.24PF$_6$

Method. Single crystals of r[5]C.24PF$_6$ were grown by slow diffusion of iPr$_2$O vapor into a solution of r[5]C.24PF$_6$ in MeCN under ambient conditions at room temperature over the course of a week.

Crystal Parameters. $C_{248}H_{264}F_{132}N_{46}P_{22}$. Colorless block (0.444×0.179×0.173 mm). Triclinic, P$\bar{1}$, a=12.349(14), b=27.43(3), c=28.24(3), α=117.225(18), β=92.74(2), γ=100.084(19°), V=8285(17) Å$^3$, Z=1, T=100.0 K, μ(MoKα)=0.238 mm$^{-1}$, $\rho_{calc}$=1.419 g/cm$^3$, 72212 reflections measured (1.64°≤2Θ≤45.44°), 21338 unique ($R_{int}$=0.0781, $R_{sigma}$=0.0890) which were used in all calculations. The final $R_1$ was 0.1371 (I>2σ(I)) and $wR_2$ was 0.4050 (all data). CCDC deposition number 1844970.

Refinement Details. Two sets of CBPQT$^{4+}$ rings, as well as the bipyridinium units of the central ring (BTB$^{8+}$), in r[5]C$^{24+}$ were found to be crystallography equivalent with an inversion center at the centroid of the BTB$^{8+}$ ring. The 1-(1-(ethylene)-1H-1,2,3-triazole-4-yl)butylene linkers of the BTB$^{8+}$ ring were found to be disordered and were modeled over two positions with half-occupancy. The solvent-masking procedure, as implemented in Olex2,[2] was used to remove the electronic contributions of one PF$_6^-$ counterion and solvent molecules, which were found to be heavily disordered and could not be refined satisfactorily, from the refinement. As the exact solvent content is not known, only the atoms used in the refinement model are reported here in the formula. Total solvent accessible volume/cell=364.85 Å$^3$ [4.4%]. Three of the 12 PF$_6^-$ counter ions in the asymmetric unit were modeled over two positions and their anisotropic displacement parameters were refined using SIMU and DELU restraints.[5] Solid-state structures of r[5]C$^{24+}$ are shown in FIG. 6A-6C and space-filling representations of the superstructure of r[5]C.24PF$_6$ are shown in FIG. 6D-6E.

UV-Vis-NIR Absorption Spectroscopy

UV-Vis-NIR spectroscopy was performed as described in the methods. UV-Vis-NIR spectra of all radical intermediates during the synthesis of dodecacationic [3]catenane, [3]C$^{12+}$ (Scheme 1; FIG. 9) were obtained (data not shown). The radical species AV$^{(\cdot+)}$, HV$^{(\cdot+)}$, and CBPQT$^{2(\cdot+)}$ were obtained by treating their oxidized forms (HV$^{2+}$, AV$^{2+}$, and CBPQT$^{4+}$, respectively) either with copper powder for 1 h or with activated zinc dust for 20 min under inert atmosphere. The two [2]pseudorotaxanes [AV⊂CBPQT]$^{3(\cdot+)}$ and [HV⊂CBPQT]$^{3(\cdot+)}$ were prepared either by mixing their two corresponding radical cations (AV$^{(\cdot+)}$+CBPQT$^{2(\cdot+)}$ and HV$^{(\cdot+)}$+CBPQT$^{2(\cdot+)}$, respectively) in 1:1 ratio or by treating the corresponding oxidized components with copper powder/zinc dust under inert atmosphere. [3]C$^{6(\cdot+)}$ was obtained by treating the purified [3]C$^{12+}$ with copper powder for an hour or with zinc dust for 20 min under inert atmosphere. The concentration of all solutions used in these UV-Vis-NIR measurements is 0.05 mM in MeCN. The reduction was carried out inside a N$_2$-filled glove box while the UV-Vis-NIR measurements were performed outside the glovebox using an airtight cuvette.

Figure 3B:
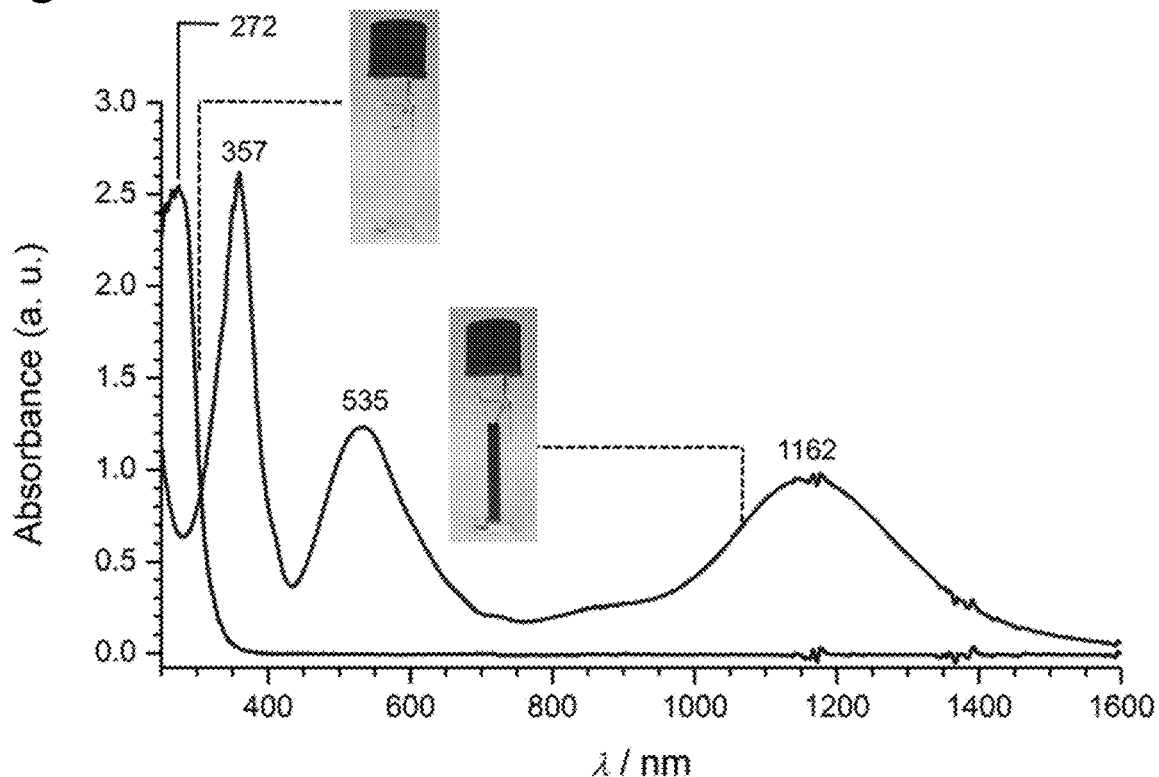
Figure 3D:
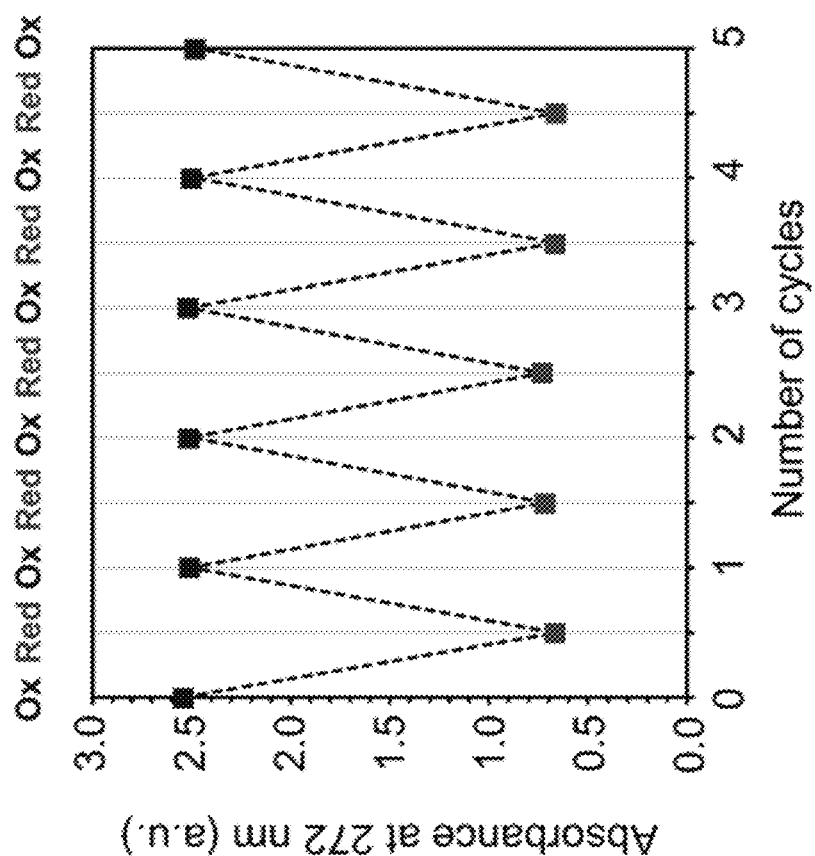
FIGS. 3C-3D. UV-Vis-NIR spectra during reversible switching between the fully oxidized $[3]C^{12+}$ and the reduced-state $[3]C^{6(.+)}$ catenanes using chemical stimuli. UV-Vis-NIR spectra of the two [3]catenane $[3]C^{12+}$ and $[3]C^{6(.+)}$ states.
Figure 3C:
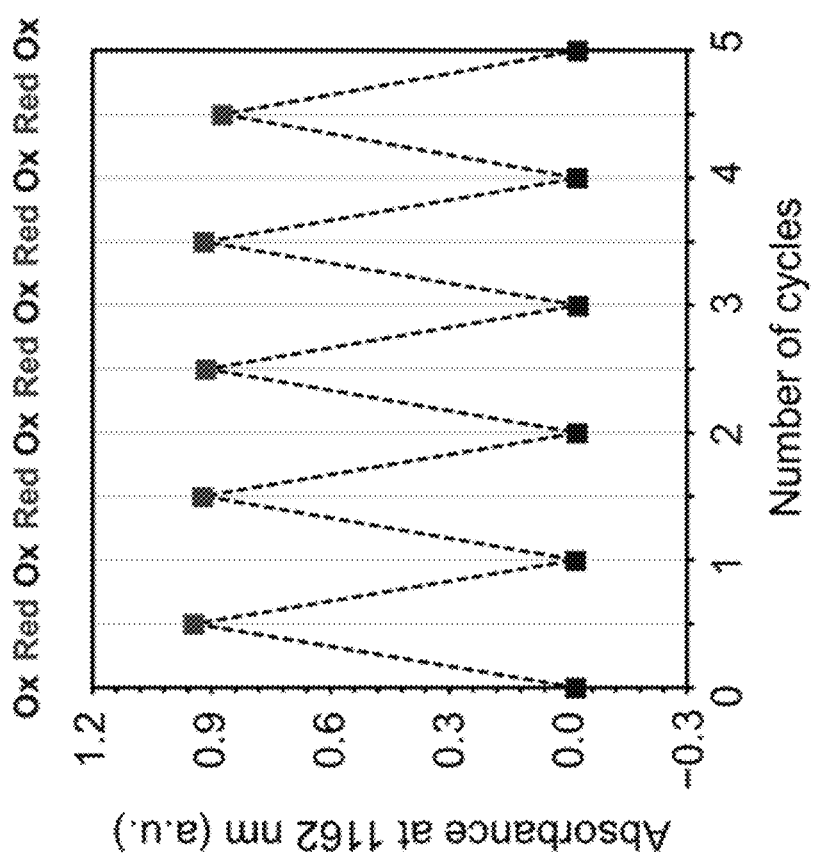
Figure 4A:
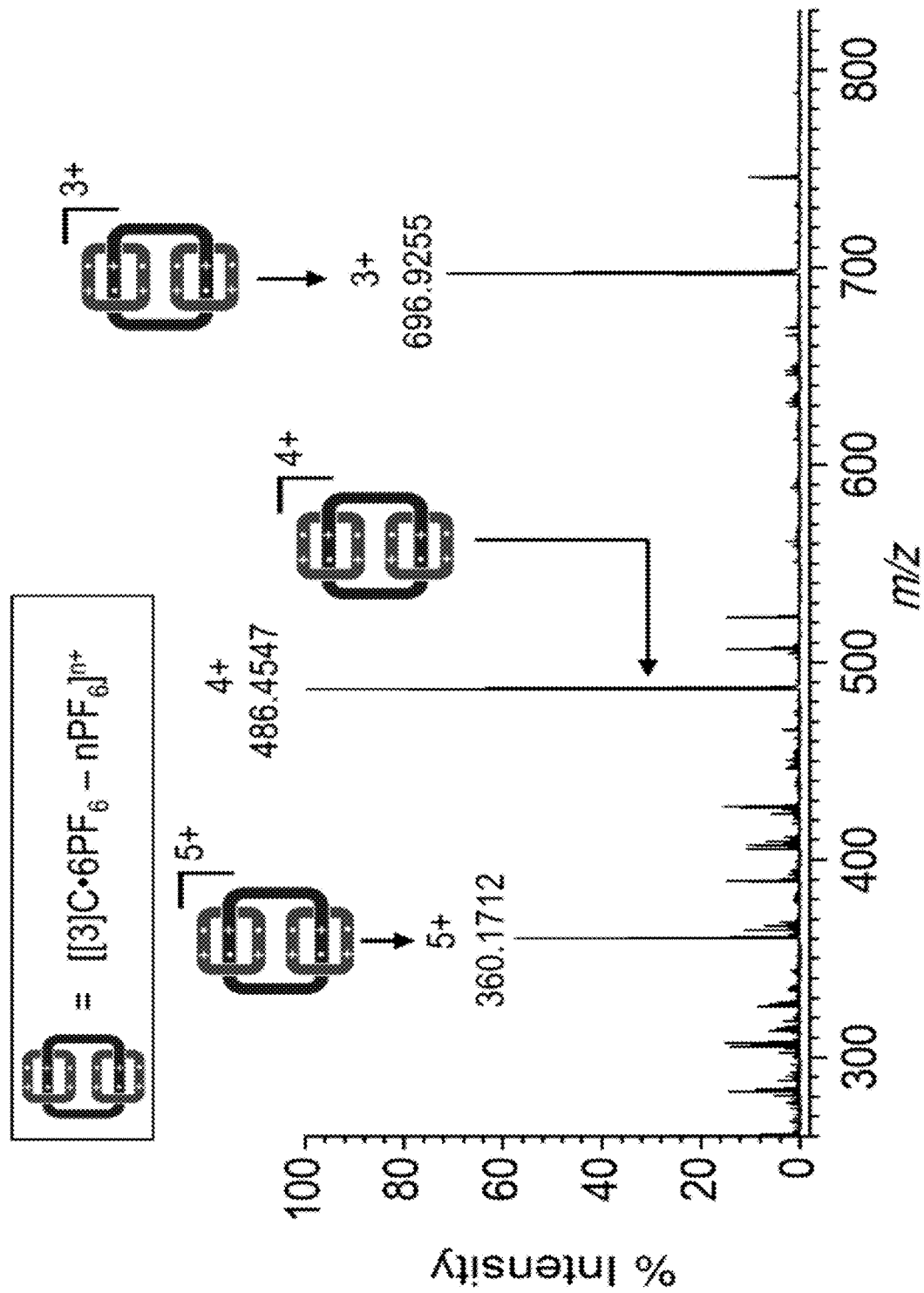
FIGS. 4AI-4AII. Mass spectrum of the hexaradical/hexacationic [3]catenane $[3]C^{6(.+)}$.
Figure 4G:
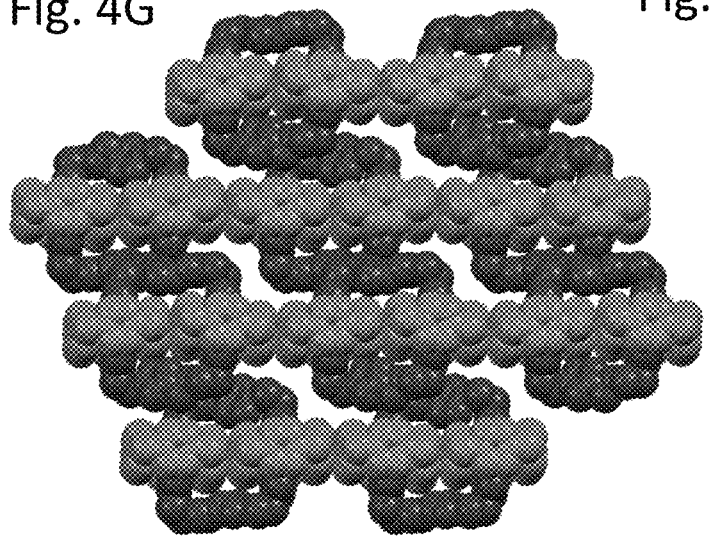
FIGS. 4G-4J. Space filling representations of the structure of the solid state structure of $[3]C.6PF_6$.
Figure 4I:
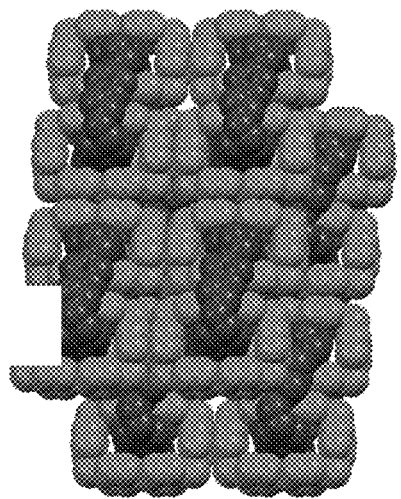
Figure 4H:
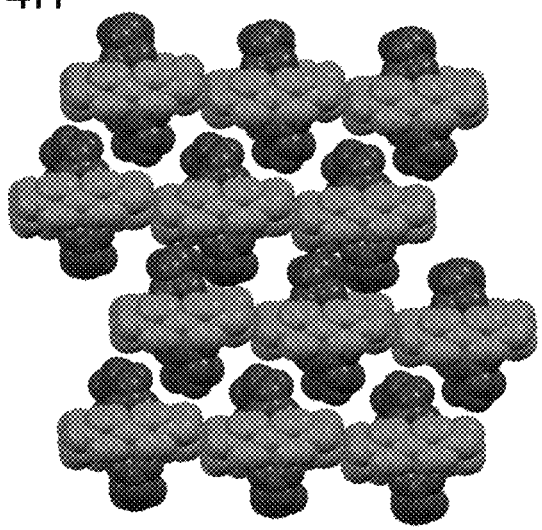
Figure 4J:
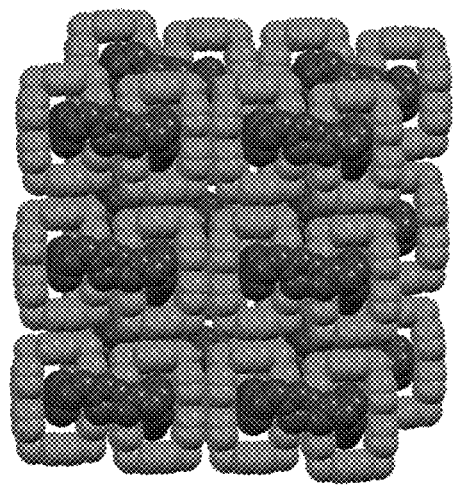

UV-Vis-NIR spectra were obtained during reversible switching between the fully oxidized [3]C$^{12+}$ and the reduced-state [3]C$^{6(\cdot+)}$ [3]catenanes using chemical stimuli. UV-Vis-NIR Spectra of the two [3]catenane [3]C$^{12+}$ and [3]C$^{6(\cdot+)}$ states are shown in FIG. 3B-3D The switching between the two states was repeated five times starting with [3]C$^{12+}$. In one cycle, a spectrum of the [3]C.12PF$_6$ solution (1.5 mL/0.03 mM in MeCN) was recorded before being treated with zinc dust for 20 min, filtered through a 0.2-µm filter and subjected to the UV-vis-NIR measurement for the resulting reduced [3]catenane. The re-oxidation of the [3]C$^{6(\cdot+)}$ back to [3]C$^{12+}$ was achieved by using NOPF$_6$ (which takes place in less than 3 s) to complete one cycle. Absorption intensities of [3]C$^{12+}$ (blue) and [3]C$^{6(\cdot+)}$ (purple) at 1162 nm wavelength showing the reversible switching between the two states during each cycle are shown in FIG. 3C, and absorption intensity of [3]C$^{12+}$ (blue) and [3]C$^{6(\cdot+)}$ (purple) at 272 nm recorded during each cycle are shown in FIG. 3D.

Figure 7A:
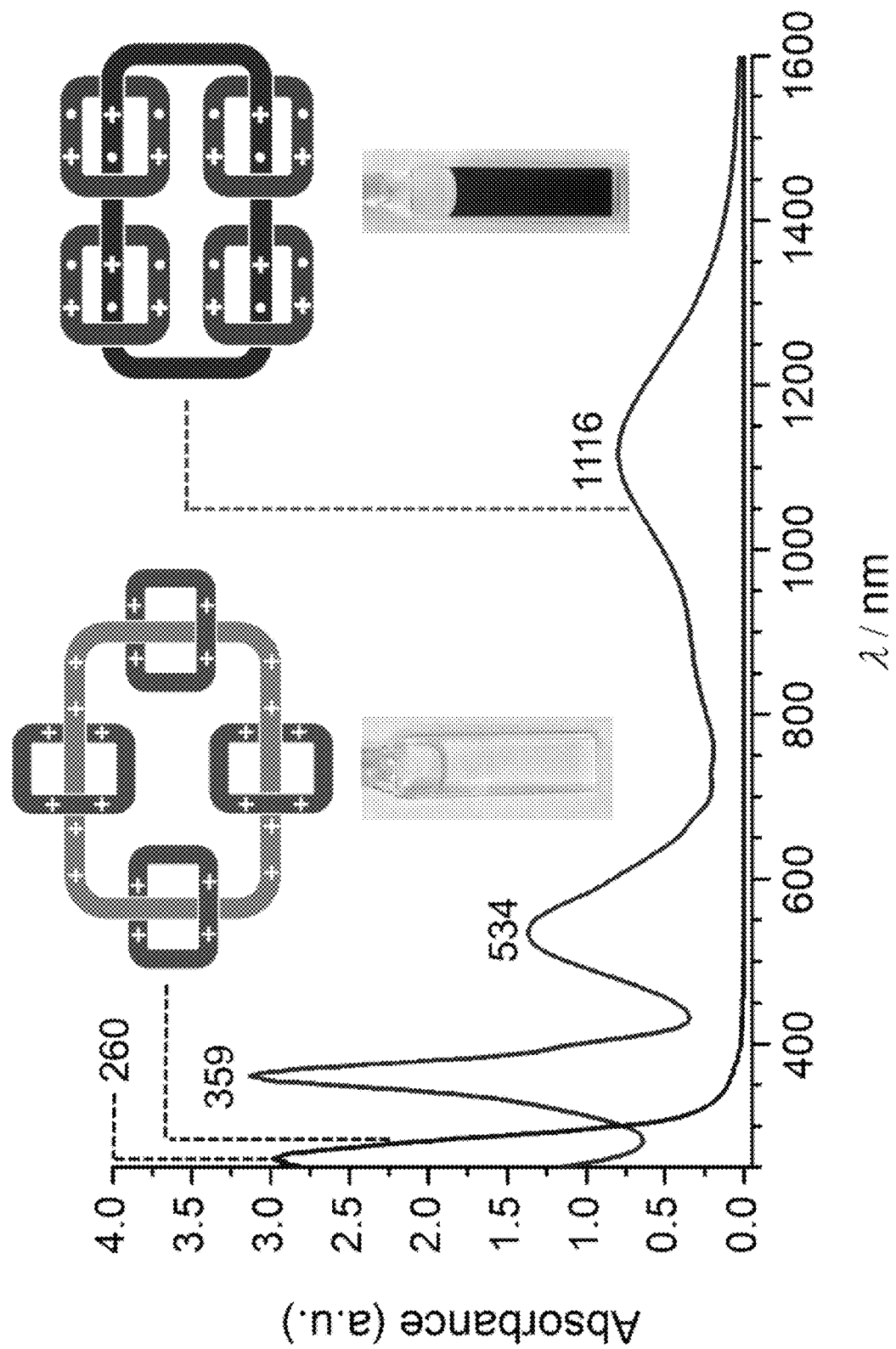
FIGS. 7A-7B. Redox switching behavior of $r[5]C^{24+}$.
Figure 7B:
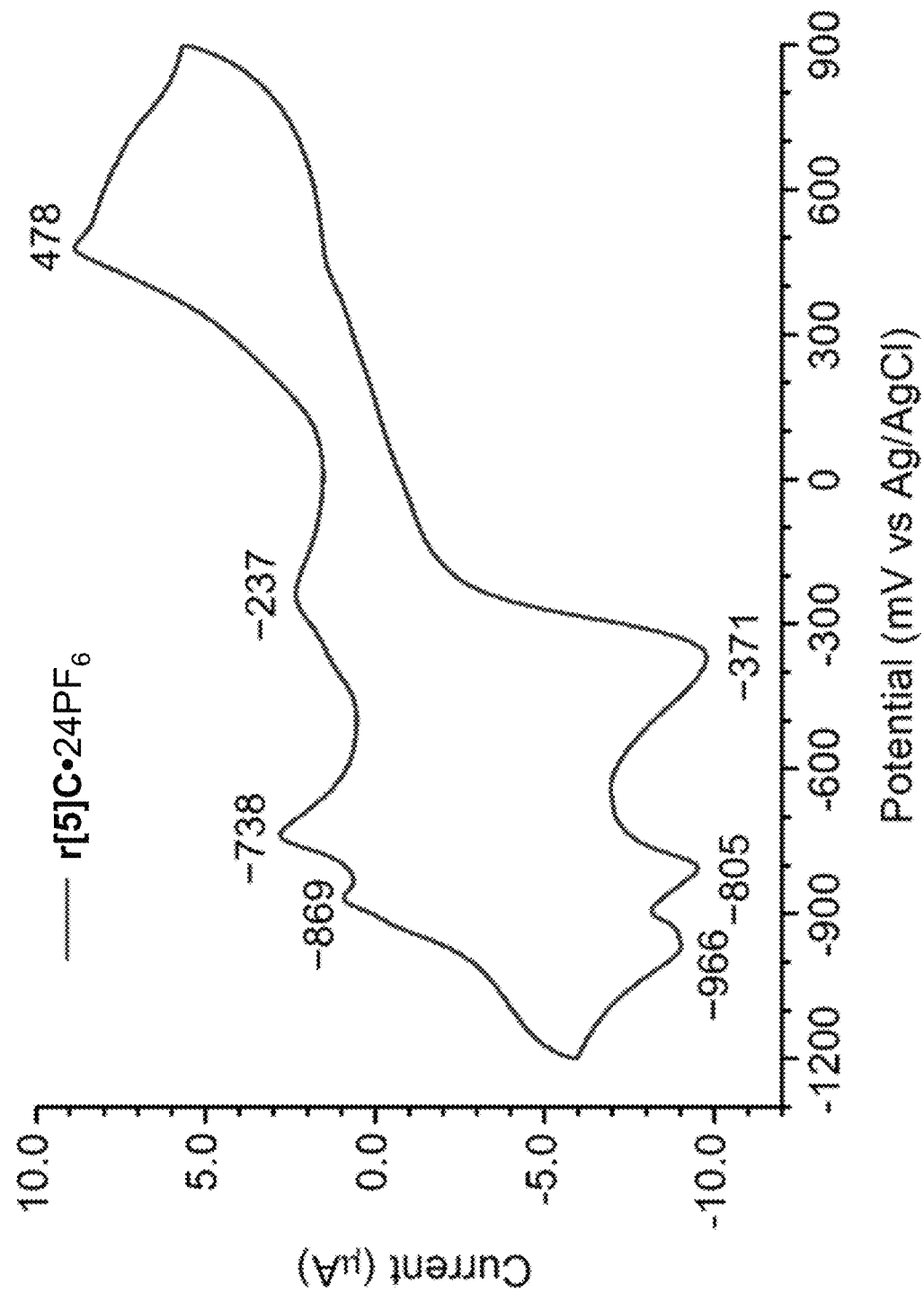
Figures 7C, 7D:
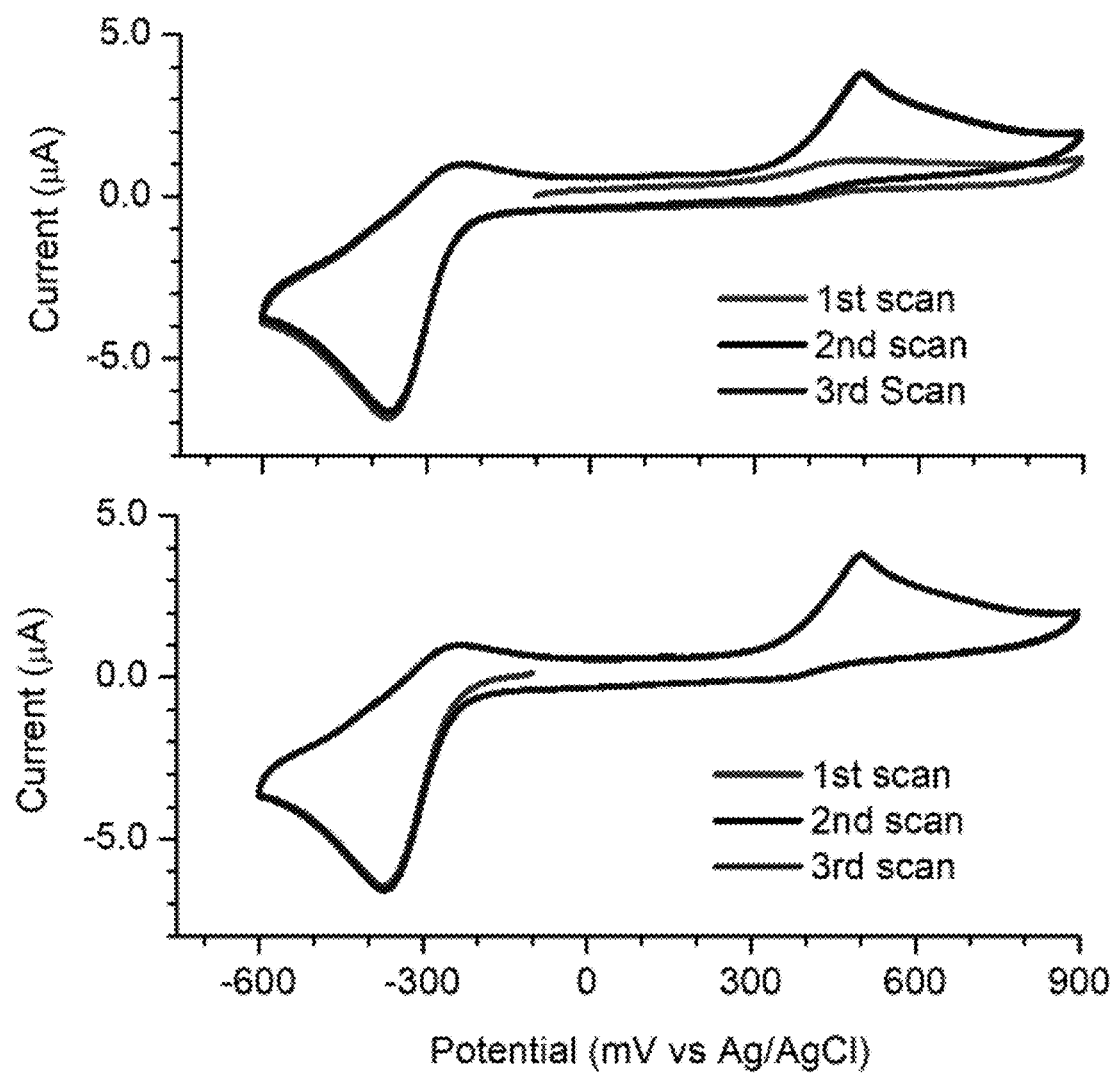
FIGS. 7C-7D. Cyclic voltammograms of $r[5]C.24PF_6$ in the −0.6 to +0.9 V potential window.

UV-Vis-NIR spectra were also obtained of radical intermediates form in the synthesis of r[5]C$^{24+}$, (data not shown), and of r[5]C$^{12(\cdot+)}$ and r[5]C$^{24+}$ generated by the reduction of r[5]C.24PF$_6$ with Zn dust, followed by a re-oxidation of the reduced state r[5]C$^{12(\cdot+)}$ by NOPF$_6$, respectively, shown in FIG. 7A.

REFERENCES

1. Yapici, N. B.; Mandalapu, S. R.; Chew, T.-L.; Khuon, S.; Bi, L. (2012). Determination of intracellular pH using sensitive, clickable fluorescent probes. Bioorg. Med. Chem. Lett. 22, 2440-2443.
2. Dolomanov, O. V.; Bourhis, L. J.; Gildea, R. J.; Howard, J. A. K.; Puschmann, H. (2009). OLEX2: a complete structure solution, refinement and analysis program. J. Appl. Crystallogr. 42, 339-341.
3. Sheldrick, G. (2015). SHELXT—Integrated space-group and crystal-structure determination. Acta Crystallogr. Sect. A 71, 3-8.
4. Sheldrick, G. (2008). A short history of SHELX. Acta Crystallogr. Sect. A 64, 112-122.
5. Spek, A. (2003). Single-crystal structure validation with the program PLATON. J. Appl. Crystallogr. 36, 7-13.
6. Sue, C.-H.; Basu, S.; Fahrenbach, A. C.; Shveyd, A. K.; Dey, S. K.; Botros, Y. Y.; Stoddart, J. F. (2010). Enabling tetracationic cyclophane production by trading templates. Chem. Sci. 1, 119-125.

We claim:

1. A cationic catenane comprising a central cationic ring and two or more radial cationic rings mechanically interlocked with the central cationic ring, wherein the central cationic ring comprises two or more viologen subunits and two reactive linkers and wherein the catenane comprises an equal number of radial cationic rings as viologen subunits.

2. The catenane of claim 1, wherein the central cationic ring comprises $$R^1 \underset{L^3-V-L^4}{\overset{L^1-V-L^2}{\diagup\diagdown}} R^2$$

wherein V is a viologen subunit, $R^1$ and $R^2$ are reactive linkers formed by a click reaction, and $L^1$, $L^2$, $L^3$, and $L^4$ are independently selected from an alkyl, an alkenyl, an aryl, an alkylaryl, a triazole, or an alkyltriazole or $$R^1 \underset{L^2-V-L^3-V-L^4}{\overset{L^1}{\diagup\diagdown}} R^2$$

wherein V is a viologen subunit, $R^1$ and $R^2$ are reactive linkers formed by a click reaction, and $L^1$, $L^2$, $L^3$, and $L^4$ are independently selected from an alkyl, an alkenyl, an aryl, an alkylaryl, a triazole, or an alkyltriazole.

3. The catenane of claim 2, wherein the catenane is a dodecacationic catenane (r[3]C$^{12+}$).

4. The catenane of claim 3, wherein each of the radial cationic rings comprise cyclobis(paraquat-p-phenylene) tetracation (CBPQT$^{4+}$).

5. The catenane of claim 2, wherein the catenane is a hexaradical/hexacationic catenane (r[3]C$^{6(\cdot+)}$).

6. The catenane of claim 5, wherein each of the radial cationic rings comprise cyclobis(paraquat-p-phenylene) bis-radical dication (CBPQT$^{2(\cdot+)}$).

7. The catenane of claim 1, wherein the central cationic ring comprises $$R^1 \underset{L^3-V-L^4-V-L^5}{\overset{L^1-V-L^2}{\diagup\diagdown}} R^2$$

wherein V is a viologen subunit, $R^1$ and $R^2$ are reactive linkers formed by a click reaction, and $L^1$, $L^2$, $L^3$, $L^4$, and $L^5$ are independently selected from an alkyl, an alkenyl, an aryl, an alkylaryl, a triazole, or an alkyltriazole.

8. The catenane of claim 7, wherein the catenane is an octodecacationic catenane (r[4]C$^{18+}$).

9. The catenane of claim 8, wherein each of the radial cationic rings comprise cyclobis(paraquat-p-phenylene) tetracation (CBPQT$^{4+}$).

10. The catenane of claim 7, wherein the catenane is a nonaradical/nonacationic catenane (r[4]C$^{9(·+)}$).

11. The catenane of claim 10, wherein each of the radial cationic rings comprise cyclobis(paraquat-p-phenylene) bisradical dication (CBPQT$^{2(·+)}$).

12. The catenane of claim 1, wherein the central cationic ring comprises

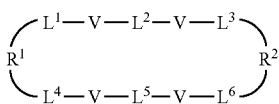

wherein V is a viologen subunit, R$^1$ and R$^2$ are reactive linkers formed by a click reaction, and L$^1$, L$^2$, L$^3$, L$^4$, L$^5$, and L$^6$ are independently selected from an alkyl, an alkenyl, an aryl, an alkylaryl, a triazole, or an alkyltriazole.

13. The catenane of claim 12, wherein the catenane is a tetracosacationic catenane (r[5]C$^{24+}$).

14. The catenane of claim 13, wherein each of the radial cationic rings comprise cyclobis(paraquat-p-phenylene) tetracation (CBPQT$^{4+}$).

15. The catenane of claim 12, wherein the catenane is a dodecaaradical/dodecacationic catenane (r[5]C$^{12(·+)}$).

16. The catenane of claim 15, wherein each of the radial cationic rings comprise cyclobis(paraquat-p-phenylene) bisradical dication (CBPQT$^{2(·+)}$).

17. A composition comprising the catenane of claim 1 and a counterion.

18. A crystalline composition comprising the catenane of claim 1.

19. A device comprising the catenane of any one of claim 1, wherein the device is a switch, transistor, memory device, electrochromic device, or redox-flow battery.

20. A method of forming a cationic catenane, the method comprising:
providing a pseudorotaxane, the pseudorotaxane comprising:
a threading component having a first terminal moiety, a second terminal moiety, and two or more radical/cation viologen subunits between the first terminal moiety and the second terminal moiety and
two or more diradical/dicationic rings threaded by the threading component,
wherein the pseudorotaxane comprises an equal number of diradical/dicationic rings as viologen subunits; and
contacting the first terminal moiety with the second terminal moiety to form a central cationic ring that mechanically interlocks the two or more diradical/dicationic rings, thereby forming the catenane,
wherein each of the radial cationic rings comprise cyclobis(paraquat-p-phenylene) bisradical dication (CBPQT$^{2(·+)}$) and/or wherein the threading component comprises two, three, or four viologen subunits.

* * * * *